United States Patent
Segers et al.

(10) Patent No.: US 10,456,451 B2
(45) Date of Patent: *Oct. 29, 2019

(54) PROTEASE-RESISTANT MUTANTS OF STROMAL CELL DERIVED FACTOR-1 IN THE REPAIR OF TISSUE DAMAGE

(71) Applicant: Mesoblast International Sàrl, Meyrin (CH)

(72) Inventors: Vincent Frans Maria Segers, Bornem (BE); Anthony Sandrasagra, Arlington, MA (US); Yan Qiu, Jamaica Plain, MA (US)

(73) Assignee: Mesoblast International Sàrl, Meyrin (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/054,456

(22) Filed: Feb. 26, 2016

(65) Prior Publication Data

US 2016/0375100 A1 Dec. 29, 2016

Related U.S. Application Data

(63) Continuation of application No. 13/029,891, filed on Feb. 17, 2011, now Pat. No. 9,308,277.

(60) Provisional application No. 61/308,090, filed on Feb. 25, 2010, provisional application No. 61/345,852, filed on May 18, 2010.

(51) Int. Cl.
| | |
|---|---|
| *A61K 38/19* | (2006.01) |
| *A61K 38/00* | (2006.01) |
| *C07K 14/52* | (2006.01) |
| *A61K 47/64* | (2017.01) |

(52) U.S. Cl.
CPC ............ *A61K 38/195* (2013.01); *A61K 47/64* (2017.08); *A61K 47/645* (2017.08); *C07K 14/522* (2013.01); *A61K 38/00* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 5,171,680 A | 12/1992 | Mullenbach et al. | |
| 5,563,048 A | 10/1996 | Honjo et al. | |
| 5,670,483 A | 9/1997 | Zhang et al. | |
| 5,756,084 A | 5/1998 | Honjo et al. | |
| 6,100,387 A | 8/2000 | Herrmann et al. | |
| 6,214,540 B1 | 4/2001 | DeVico et al. | |
| 6,221,856 B1 | 4/2001 | Traynor-Kaplan et al. | |
| 6,440,934 B1 | 8/2002 | Whitehouse | |
| 6,548,630 B1 | 4/2003 | Zhang et al. | |
| 6,852,508 B1 | 2/2005 | Herrmann et al. | |
| 6,875,738 B1 | 4/2005 | Clark-Lewis et al. | |
| 6,946,445 B1 | 9/2005 | Clark-Lewis et al. | |
| 7,354,899 B2 | 4/2008 | Clark-Lewis et al. | |
| 7,368,425 B2* | 5/2008 | Merzouk ................ | A61K 38/12 424/85.1 |
| 7,378,098 B2 | 5/2008 | Tudan et al. | |
| 7,435,718 B2 | 10/2008 | Tudan et al. | |
| 7,485,141 B2 | 2/2009 | Majercak et al. | |
| 7,527,946 B2 | 5/2009 | Whitty et al. | |
| 7,547,674 B2 | 6/2009 | Anversa et al. | |
| 7,662,392 B2 | 2/2010 | Itescu | |
| 7,696,309 B2 | 4/2010 | Lee et al. | |
| 7,999,067 B2 | 8/2011 | Lee et al. | |
| 8,414,924 B2 | 4/2013 | Oh et al. | |
| 8,496,931 B2* | 7/2013 | Pogue .................... | C07K 16/24 424/130.1 |
| 9,175,267 B2 | 11/2015 | Gronthos et al. | |
| 9,308,277 B2* | 4/2016 | Segers ................. | C07K 14/522 |
| 9,631,005 B2 | 4/2017 | Lee et al. | |
| 2002/0094327 A1 | 7/2002 | Petersen | |
| 2002/0107195 A1 | 8/2002 | Gupta | |
| 2002/0107196 A1 | 8/2002 | Gupta | |
| 2002/0111290 A1 | 8/2002 | Homey et al. | |
| 2002/0156023 A1 | 10/2002 | Walling et al. | |
| 2002/0165123 A1 | 11/2002 | Tudan et al. | |
| 2003/0199464 A1 | 10/2003 | Itescu | |
| 2003/0215792 A1 | 11/2003 | Muller et al. | |
| 2004/0037811 A1 | 2/2004 | Penn et al. | |
| 2004/0247564 A1 | 12/2004 | Itescu | |
| 2005/0020528 A1 | 1/2005 | Herrmann et al. | |
| 2005/0059584 A1 | 3/2005 | Merzouk et al. | |

(Continued)

FOREIGN PATENT DOCUMENTS

| | | |
|---|---|---|
| CN | 101553243 A | 10/2009 |
| JP | 2007-537752 A | 12/2007 |

(Continued)

OTHER PUBLICATIONS

Claims (May 3, 2017), U.S. Appl. No. 14/124,187.*
Claims (Oct. 13, 2016), U.S. Appl. No. 15/103,153.*
Claims (Feb. 16, 2017), U.S. Appl. No. 15/374,539.*
Askari et al., "Effect of stromal-cell-derived factor 1 on stem-cell homing and tissue regeneration in ischaemic cardiomyopathy," Lancet. 362(9385):697-703 (2003).
Badillo et al., "Lentiviral gene transfer of SDF-1alpha to wounds improves diabetic wound healing," J Surg Res. 143(1):35-42 (2007).
Bowie et al., "Deciphering the message in protein sequences: tolerance to amino acid subsitutions," Science. 247(4948):1306-10 (1990).

(Continued)

*Primary Examiner* — Elizabeth C. Kemmerer
(74) *Attorney, Agent, or Firm* — Clark & Elbing LLP

(57) ABSTRACT

The present invention features mutant stromal cell derived factor-1 (SDF-1) peptides that have been mutated to make them resistant to digestion by, for example, the proteases dipeptidyl peptidase IV (DPPIV), matrix metalloproteinase-2 (MMP-2), matrix metalloproteinase-9 (MMP-9), leukocyte elastase, cathepsin G, carboxypeptidase M, and carboxypeptidase N, but which retain chemoattractant activity.

21 Claims, 16 Drawing Sheets
(6 of 16 Drawing Sheet(s) Filed in Color)
Specification includes a Sequence Listing.

(56) References Cited

U.S. PATENT DOCUMENTS

| | | |
|---|---|---|
| 2005/0065064 A1 | 3/2005 | Lolis et al. |
| 2005/0142101 A1 | 6/2005 | Forssmann et al. |
| 2005/0271639 A1 | 12/2005 | Penn et al. |
| 2006/0088510 A1 | 4/2006 | Lee et al. |
| 2006/0110374 A1 | 5/2006 | Czeiger et al. |
| 2006/0148703 A1 | 7/2006 | Lee et al. |
| 2007/0060512 A1 | 3/2007 | Sadeghi et al. |
| 2007/0172811 A1 | 7/2007 | Srivastava et al. |
| 2007/0203062 A1 | 8/2007 | Ellis-Behnke et al. |
| 2007/0224171 A1 | 9/2007 | Penn et al. |
| 2007/0258943 A1 | 11/2007 | Penn et al. |
| 2008/0095758 A1 | 4/2008 | Lee et al. |
| 2008/0253996 A1 | 10/2008 | Boschert et al. |
| 2009/0029912 A1 | 1/2009 | Gronthos et al. |
| 2010/0166717 A1 | 7/2010 | Penn |
| 2010/0267612 A1 | 10/2010 | Tabata |
| 2010/0304477 A1 | 12/2010 | Buscher et al. |
| 2011/0014691 A1 | 1/2011 | Menasche et al. |
| 2011/0159099 A1 | 6/2011 | Yasuda et al. |
| 2011/0224139 A1 | 9/2011 | Segers et al. |
| 2011/0269685 A1 | 11/2011 | Lee et al. |
| 2012/0157381 A1 | 6/2012 | Spees |
| 2012/0165392 A1 | 6/2012 | Olson et al. |
| 2014/0199304 A1 | 7/2014 | Sandrasagra et al. |
| 2016/0303197 A1 | 10/2016 | Sandrasagra et al. |
| 2017/0101451 A1 | 4/2017 | Lee et al. |

FOREIGN PATENT DOCUMENTS

| | | |
|---|---|---|
| WO | WO-02/38172 A2 | 5/2002 |
| WO | WO-2004/017978 A1 | 3/2004 |
| WO | WO-2004/094465 A2 | 11/2004 |
| WO | WO-2005/116192 A2 | 12/2005 |
| WO | WO-2006/032075 A1 | 3/2006 |
| WO | WO-2006/047315 A2 | 5/2006 |
| WO | WO-2006/073889 A2 | 7/2006 |
| WO | WO-2006/074464 A2 | 7/2006 |
| WO | WO-2006/124013 A2 | 11/2006 |
| WO | WO-2007/079460 A2 | 7/2007 |
| WO | WO-2011/026041 A2 | 3/2011 |
| WO | WO-2011/106234 A1 | 9/2011 |
| WO | WO-2012/027170 A1 | 3/2012 |
| WO | WO-2012/170495 A1 | 12/2012 |
| WO | WO-2015/089396 A1 | 6/2015 |

OTHER PUBLICATIONS

Carr et al., "Efficacy of systemic administration of SDF-1 in a model of vascular insufficiency: support for an endothelium-dependent mechanism," Cardiovasc Res. 69(4):925-35 (2006).

Chang et al., "Regenerative therapy for stroke," Cell Transplant. 16(2):171-81 (2007).

Chen et al., "Site-specific labeling of cell surface proteins with biophysical probes using biotin ligase," Nat Methods. 2(2):99-104 (2005).

Cosset et al., "High-titer packaging cells producing recombinant retroviruses resistant to human serum," J Virol. 69(12):7430-6 (1995).

Crump et al., "Solution structure and basis for functional activity of stromal cell-derived factor-1; dissociation of CXCR4 activation from binding and inhibition of HIV-1," EMBO J. 16(23):6996-7007 (1997).

Cui et al., "Nitric oxide donor upregulation of stromal cell-derived factor-1/chemokine (CXC motif) receptor 4 enhances bone marrow stromal cell migration into ischemic brain after stroke," Stem Cells. 25(11):2777-85 (2007).

Davis et al., "Local myocardial insulin-like growth factor 1 (IGF-1) delivery with biotinylated peptide nanofibers improves cell therapy for myocardial infarction," Proc Natl Acad Sci U S A. 103(21):8155-60 (2006).

De La Luz Sierra et al., "Differential processing of stromal-derived factor-1alpha and stromal-derived factor-1beta explains functional diversity," Blood. 103(7):2452-9 (2004).

Di Rocco et al., "Enhanced healing of diabetic wounds by topical administration of adipose tissue-derived stromal cells overexpressing stromal-derived factor-1: biodistribution and engraftment analysis by bioluminescent imaging," Stem Cells Int. 2011:304562 (2010) (11 pages).

Elmadbouh et al., "Ex vivo delivered stromal cell-derived factor-1alpha promotes stem cell homing and induces angiomyogenesis in the infarcted myocardium," available in PMC Sep. 28, 2009, published in final edited form as: J Mol Cell Cardiol. 42(4):792-803 (2007).

Gallagher et al., "Diabetic impairments in NO-mediated endothelial progenitor cell mobilization and homing are reversed by hyperoxia and SDF-1 alpha," J Clin Invest. 117(5):1249-59 (2007).

Heveker et al., "Pharmacological properties of peptides derived from stromal cell-derived factor 1: study on human polymorphonuclear cells," Mol Pharmacol. 59(6):1418-1425 (2001).

Hiasa et al., "Gene transfer of stromal cell-derived factor-1alpha enhances ischemic vasculogenesis and angiogenesis via vascular endothelial growth factor/endothelial nitric oxide synthase-related pathway: next-generation chemokine therapy for therapeutic neovascularization," Circulation. 109(20):2454-61 (2004).

Hsieh et al., "Controlled delivery of PDGF-BB for myocardial protection using injectable self-assembling peptide nanofibers," J Clin Invest. 116(1):237-48 (2005).

Kanki et al., "Stromal cell-derived factor-1 retention and cardioprotection for ischemic myocardium," Circ Heart Fail. 4(4):509-18 (2011).

Koch et al., "Effect of catheter-based transendocardial delivery of stromal cell-derived factor 1alpha on left ventricular function and perfusion in a porcine model of myocardial infarction," Basic Res Cardiol. 101:1-9 (2005).

Kryczek et al., "Stroma-derived factor (SDF-1/CXCL12) and human tumor pathogenesis," Am J Physio Cell Physiol. 292(3):C987-95 (2007).

Lambeir et al., "Kinetic investigation of chemokine truncation by CD26/dipeptidyl peptidase IV reveals a striking selectivity within the chemokine family," J Biol Chem. 276(32):29839-45 (2001).

Lapidot et al., "How do stem cells find their way home?" Blood. 106(6):1901-10 (2005).

Loetscher et al., "N-terminal peptides of stromal cell-derived factor-1 with CXC chemokine receptor 4 agonist and antagonist activities," J Biol Chem. 273(35):22279-83 (1998).

McQuibban et al., "Matrix metalloproteinase activity inactivates the CXC chemokine stromal cell-derived factor-1," J Biol Chem. 276(47):43503-8 (2001).

Medical Technology 3-DM Inc. Products, Introduction, Puramatrix, http//www.puramatrix.com/pr01.html, Retrieved on Sep. 3, 2009 (1 page).

Mirshahi et al., "SDF-1 activity on microvascular endothelial cells: consequences on angiogenesis in in vitro and in vivo models," Thromb Res. 99(6):587-94 (2000).

Nagasawa et al., "Defects of B-cell lymphopoiesis and bone-marrow myelopoiesis in mice lacking the CXC chemokine PBSF/SDF-1," Nature. 382(6592):635-8 (1996).

Netzel-Arnett et al., "Comparative sequence specificities of human 72- and 92-kDa gelatinases (type IV collagenases) and PUMP (matrilysin)," Biochemistry. 32(25):6427-32 (1993).

Ngo et al., Computational Complexity, Protein Structure, and the Levinthal Paradox. The Protein Folding Problem and Tertiary Structure Prediction, Merz and Le Grand, 433, 492-495 (1994).

Ohab et al., "A neurovascular niche for neurogenesis after stroke," J Neurosci. 26(50):13007-16 (2006).

Ohnishi et al., "Crystal structure of recombinant native SDF-1alpha with additional mutagenesis studies: an attempt at a more comprehensive interpretation of accumulated structure-activity relationship data," J Interferon Cytokine Res. 20(8):691-700 (2000).

Penn et al., "Role of stem cell homing in myocardial regeneration," Int J Cardiol. 95(Suppl 1):S23-5 (2004).

Peterson et al., "Evolution of matrix metalloprotease and tissue inhibitor expression during heart failure progression in the infarcted rat," Cardiovasc Res. 46(2):307-15 (2000).

Petit et al., "The SDF-1-CXCR4 signaling pathway: a molecular hub modulating neo-angiogenesis," Trends in Immunol. 28(7):299-307 (2007).

(56) References Cited

OTHER PUBLICATIONS

Pillarisetti et al., "Cloning and relative expression analysis of rat stromal cell derived factor-1 (SDF-1)1: SDF-1 alpha mRNA is selectively induced in rat model of myocardial infarction," Inflammation. 25(5):293-300 (2001).
Rosenblum et al., "Prolyl peptidases: a serine protease subfamily with high potential for drug discovery," Curr Opin Chem Biol. 7(4):496-504 (2003).
Sasaki et al., "Stromal cell-derived factor-1alpha improves infarcted heart function through angiogenesis in mice," Pediatr Int. 49(6):966-71 (2007).
Saxena et al., "Stromal cell-derived factor-1alpha is cardioprotective after myocardial infarction," Circulation. 117(17):2224-31 (2008).
Schubert, "Measurement of oral tissue damage and musositis pain," http://painresearch.utah.edu/cancerpain/ch15.html, retrieved Nov. 4, 2011, (1-16).
Segers et al., "Local delivery of protease-resistant stromal cell derived factor-1 for stem cell recruitment after myocardial infarction," Circulation. 116(15):1683-92 (2007).
Segers et al., "Protease-resistant stromal cell-derived factor-1 for the treatment of experimental peripheral artery disease," Circulation. 123(12)1306-15 (2011).
Shioda et al., "Anti-HIV-1 and chemotactic activities of human stromal cell-derived factor 1alpha (SDF-1alpha) and SDF-1beta are abolished by CD26/dipeptidyl peptidase IV-mediated cleavage," Proc Natl Acad Sci U S A. 95(11):6331-6 (1998).
Tan et al., "Cloning and characterizing mutated human stromal cell-derived factor-1 (SDF-1): C-terminal alpha-helix of SDF-1alpha plays a critical role in CXCR4 activation and signaling, but not in CXCR4 binding affinity," Exp Hematol. 34(11):1553-62 (2006).
Valenzuela-Fernandez et al., "Leukocyte elastase negatively regulates Stromal cell-derived factor-1 (SDF-1)/CXCR4 binding and functions by amino-terminal processing of SDF-1 and CXCR4," J Biol Chem. 277(18)15677-89 (2002).
Wang et al., "Roles of chemokine CXCL12 and its receptors in ischemic stroke," Curr Drug Targets. 13(2):166-72 (2012).
Yamaguchi et al., "Stromal cell-derived factor-1 effects on ex vivo expanded endothelial progenitor cell recruitment for ischemic neovascularization," Circulation. 107(9):1322-8 (2003).
Yu et al., "Identification and expression of novel isoforms of human stromal cell-derived factor 1," Gene. 374:174-9 (2006).
Zahradka et al., "Activation of MMP-2 in response to vascular injury is mediated by phosphatidylinositol 3-kinase-dependent expression of MT1-MMP," Am J Physiol Heart Circ Physiol. 287(6):H2861-70 (2004).
Zhang et al., "Controlled release of stromal cell-derived factor-1 alpha in situ increases c-kit+ cell homing to the infarcted heart," Tissue Eng. 13(8):2063-71 (2007).
Zhong et al., "Small peptide analogs to stromal derived factor-1 enhance chemotactic migration of human and mouse hematopoietic cells," Exp Hematol. 32(5):470-5 (2004).
Zou et al., "Function of the chemokine receptor CXCR4 in haematopoiesis and in cerebellar development," Nature. 393(6685):595-9 (1998).
European Search Report for European Patent Application No. 12796309.8, dated Jan. 28, 2015 (7 pages).
Extended European Search Report for European Patent Application No. 13185216.2, dated Nov. 27, 2013 (13 pages).
Extended European Search Report for European Patent Application No. 07867257.3, dated Aug. 10, 2010 (11 pages).
International Search Report and Written Opinion for International Patent Application No. PCT/US2007/022394, dated Sep. 26, 2008 (14 pages).
International Search Report and Written Opinion for International Patent Application No. PCT/US11/25239, dated Aug. 1, 2011 (13 pages).
International Search Report and Written Opinion for International Patent Application No. PCT/US11/48097, dated Jan. 11, 2012 (17 pages).
International Search Report and Written Opinion for International Patent Application No. PCT/US2012/041054, dated Sep. 17, 2012 (14 pages).
International Search Report and Written Opinion for International Patent Application No. PCT/US2014/070010, dated Apr. 7, 2015 (14 pages).
Office Action for Chinese Application No. 201280037907.4, dated Nov. 3, 2014 (English Translation Included) (19 pages).
Zhang et al., "SDF-1 expression by mesenchymal stem cells results in trophic support of cardiac myocytes after myocardial infarction," FASEB J. 21(12):3197-207 (2007).
Extended European Search Report for European Patent Application No. 14869229.6, dated Apr. 20, 2017 (7 pages).
Search Report for Singaporean Patent Application No. 11201604793Y, dated Aug. 7, 2017 (3 pages).
Written Opinion for Singaporean Patent Application No. 11201604793Y, dated Aug. 10, 2017 (7 pages).
Office Action for U.S. Appl. No. 15/103,153, dated Jan. 16, 2018 (15 pages).
Office Action for U.S. Appl. No. 14/124,187, dated Mar. 8, 2018 (15 pages).
Ratajczak et al., "The pleiotropic effects of the SDF-1-CXCR4 axis in organogenesis, regeneration and tumorigenesis," Leukemia. 20(11):1915-1924 (2006).
Elmadbouh et al., "Ex-vivo delivered stromal cell-derived factor-1 alpha promotes stem cell homing and induces angiomyogenesis in the infarcted myocardium," available in PMC Sep. 28, 2009, published in final edited form as: J Mol Cell Cardiol 42(4):792-803 (2007) (19 pages).
Jin et al., "Stromal cell derived factor-1 enhances bone marrow mononuclear cell migration in mice with acute liver failure," World J Gastroenterol 15(21):2657-64 (2009).

* cited by examiner

Fig. 1A-1

SDF-1α (SEQ ID NO:52)
KPVSLSYRCPCRFFESHVARANVKHLKILNTPNCALQIVARLKNNNRQVCI
DPKLKWIQEYLEKALNK

SDF-1β (SEQ ID NO:63)
KPVSLSYRCPCRFFESHVARANVKHLKILNTPNCALQIVARLKNNNRQVCI
DPKLKWIQEYLEKALNKRFKM

SDF-1γ (SEQ ID NO:64)
KPVSLSYRCPCRFFESHVARANVKHLKILNTPNCALQIVARLKNNNRQVCI
DPKLKWIQEYLEKALNKGRREEKVGKKEKIGKKKRQKKRKAAQKRKN

Fig. 1A-2

SDF-1α (SEQ ID NO:86)
MNAKVVVVLVLVLTALCLSDGKPVSLSYRCPCRFFESHVARANVKHLKILNTPNCALQIVARLKNNNRQ
VCIDPKLKWIQEYLEKALNK

SDF-1β (SEQ ID NO:87)
MNAKVVVVLVLVLTALCLSDGKPVSLSYRCPCRFFESHVARANVKHLKILNTPNCALQIVARLKNNNRQ
VCIDPKLKWIQEYLEKALNKRFKM

SDF-1γ (SEQ ID NO:88)
MNAKVVVVLVLVLTALCLSDGKPVSLSYRCPCRFFESHVARANVKHLKILNTPNCALQIVARLKNNNRQ
VCIDPKLKWIQEYLEKALNKGRREEKVGKKEKIGKKKRQKKRKAAQKRKN

Fig. 1B

SDF-1α cDNA (SEQ ID NO:69)

```
GCCGCACTTTCACTTCCGTCAGCCGCATTGCCCGCCTCGGCTCGGCCCCGACCCGCTCGTCCGCCCGCCCGCCCGCCCG
CGCCATGAACGCCAAGGTCGTGGTCGTGCTGGTCCTCGTGCTGACCGCGCTCTGCCTCAGCGATGGGAAGCCCGTCAGCCTGAGCTAC
AGATGCCCATGCCGATTCTTCGAAAGCCATGTTGCCAGAGCCAACAAGTCAAGCATCTCAAAATTCTCAAACACTCAAACTGTGCCCTTC
AGATTGTAGCCCGGCTGAAGAACAACAGACAAGTGTGCATTGACCCGAAGCTAAAACTTGATTGGATTCAGGAGTACCTGGAGAAAGCTTT
AAACAAGTAAGCACACAGCCAAAAAGGACTTTCCGCTAGACCCACTCGAGGGGAACCATTGCATCCATGCCCTGTGCCTGTGATCGGGCTGCCAGCA
CGTGGGGAGGGGCCTTAATAGCATTTAGAGAAGAGAATTGTATTATCAACAGAGTAGTACTCAAGATCTGAATTGGCTTGTTGGAGCATCTCCTCGTCCCCTGGGAGTCTGGGC
TTTAGACCCTGCATTTCTAAGAAAGAGAATTGTATTATCAACAGAGTAGTACTCAAGATCTGAATTGGCTTGTTGGAGCATCTCCTCGTCCCCTGGGAGTCTGGGC
CATTCTCATTTTAAATCAACGAGTACTCAAGATCTGAATTGTATTATCAACAGAGTAGTACTCAAGATCTGAATTGGCTTGTTCTTCAGACACTGAGGCTCCCGCCAGCAGCGCCCCTCCCAAGAGG
ACAGTCAGGTGGCTTAACAGGGAGCTGGAAAAGTGTCCTTTCTTCAGACACTGAGGCTCCTTCAACCTGCCTTCAACCTGCCTCCTCTCTTCAACCTGCCTCCTCTCTTCAACCTGCCTCCTCTCTCAGTGATTGGCTCTGTG
AAGGCCTCTGTGTGCACTCAGATACCGGGACTGTGCTCAGAGACCCCTCTCAGAGACCCCTCGATCAGCCGCCGACCCCCTCGCGAAGAGGGGTGATTGCTGGGCTCGTGCCCTG
GCTCCCATGTAGAAGCCACTACTACTTGCTTCTCATTTCTGTAGCCTGATCAGCCGCCGACCCCCTCGCGAAGAGGGGTGATTGCTGGGCTCGTGCCCTG
CATCCCCTCCTCCCCAGGCCTGCCCCGCCCAAGCTCGGGCGCCTTACCCGCAAAAGACAAAGTCTTTACAGAAGTCTTTACAGAATCAAATGCAATTTAAATCTGAGGTTTCCGAAATCAGAAGCGAA
CTGGGGATGTGTAAATGGTCCCCCTGATTGTGTGCCTCTGAAGCCTCACTACTTGCCACTCACAGAAGGTCCTGGTGATATTGTAACTTTTTTGCAAGGCATTTTTTTATATATATTTTTGT
GAGTGACTGGGTTTGTGATAAACCATCATCTGCCACTCACAGAAGGTCCTGGTGATATTGTAACTTTTTTGCAAGGCATTTTTTTATATATATTTTTGT
AAAATCAGTAGTGAATAAACCATCATCTGCCACTCACAGAAGGTCCTGGTGATATTGTAACTTTTTTGCAAGGCATTTTTTTATATATATTTTTGT
TGACATTTCCATGCATAAATGCGATCCACAGAAGGTCCTGGTGATATTGTAACTTTTTTGCAAGGCATTTTTTTATATATATTTTTGT
GCACATTTTTTTACGTTTCTTTAGAAAACAAATGTATTTCAAAATATATTTAGTCGAACAATTCATATATTGAAGTGGAGCCA
TATGAAATGTCAGTAGTTTATACTTCTATTTTTCACTGTATTTTTCACTGTATCTGTACTAAAATGTATCAAATGTGACATTAGTCACTAGCAATAAATGTGATTGCA
GCTTTTCAATGTTAGCCACAGTGTATTTTTCACTGTATCTGTACTAAAATGTATCAAATGTGACATTAGTCACTAGCAATAAATGTGATTGCA
ATTGTTTCATGGTATAAACGTCCTACTGTATGTGGGAATTTATTTACCTGAAATAAAATTCATTAGTGTTAGTGATGGAGCTTAAAA
AAAA
```

Fig. 1C-1

SDF-1β cDNA (SEQ ID NO:70)

```
GCCGCACTTTCACTCTCCGTCAGCCGCATTGCCCGCTCGGCCGTCGCTCGTCCGCCCGCCCCGCCC
GCGCCATGAACGCCAAGGTCGTGGTGGTGCTGGTGCTCGTGCTCACCGCGCTCTGCCTCAGCGACGGGAAGCCCGTCAGCCTGAGCT
ACAGATGCCCATGCCGATTCTTCGAAGAACAACAAGACAAGTTGCCAGAGCATCTCAAGCGTCAAAATTCTCAACACTCCAAACTGTGCCC
TTCAGATTGTAGCCCGGCTGAAGAATGTGAAGATGTGTGAGAAGCCTGAGACGCCTTACAGAGTGCCTGAAACCAGTGTTAGGG
CTTTAAACAAGAGGTTCAAGAGGTCAGAGATGTGAGAGGCCCAGCATTGCCAAGGGCTTTGTTTTGCACATTTGCCATATTTTCACCA
AAGGGCCTGCCACAGCCTCCCTGCCAGGGCCATTGCCAAGGGGTTTGTTTTGATTATTCAGTTCACTGGCGACACGTAGCAGCTTAGACTA
TTTGATTATGTAGCAAAATACATGACATTTATTTTTCATTTAGTTTGATTATTCAGTTTGATTATTCAGCTTTGTATTCTCTGAG
AGGCCATTATTGTACTTGCCTTATTAGAGTGTCTTTCCACGGAGCCACTCCTCTGACTCAGGGCTCCTGGGTTTGTATTCTCTGAG
CTGTGCAGGTGGGAGACTGGGCTGAGGGAGCCTAGTGAAAGGCTTCTCTGTGGGATGGAATGGCTACCCTGAGCTGAGGCCAGTGTGAGGCCAGGG
GCCAGGACCAGTCAACCTGGGCAAAGCCCTCATCCTGGGCTCTGCCTCTTCTGGGAGGGCAGCCGTTCTGCTCATCATTGTAAACTGTGCACCAAGCAGGAAATGAAAAATGT
CTTCTCCATCCACATGGGGAGCCCGGTTCATCCCGAGCCAAAAGGACTCTGTCTTGTTGGAAATATTGTCCAATTCCTATGTTTTGTTCAAAGCCAG
TCCACGAGTGAGACTGTCTCCAAAAGACCACACTGTGCACATCTGTCTGTTGTTTGGAAATATTGTCCAATTCCTATGTTTTGTTCAAAGCCAG
CTTGTGTTACCTGACCAATGTCTTGATGCATGCATGTCTTGATGCATGCAGCCGCTGAGCGAGGATGCTCCTTGGCCCTTTGA
CGTCCTCCTCTGTGACCAATGTCTTGATGCATGCATGTCTTGATGCATGCAGCCGCTGAGCGAGGAGATGCTCCTTGGCCCTTTGA
GTGCAGTCCTGATCAGAGCCGGTGTGCACACTGCTTGGGGTGAACTACCTTGGTTCCCCCACTGATCACAAAAACATGGTGGTCATGTCCTCAAA
GAGCCCAAGCCCAGCCCAGCCCAGGGTTGACCCCCAGAGGATTGCTGCCCCATCAGTGTCTTCCCTCACATTGTTTTTGGTTTTTAAAACCCACAAAATAACCAAT
CTAGGGCCAAGCATGAAGATTCTTTCGCAGCACTGCTTCCAATTCACATCAACAAGCATTCACACTTCTTCACCAGAGACATTTCTCTAAGAGAACAATGCTATGTGAAGAGTA
CCTGGACACATGAAGATTCTTTCGCAGCACTGCTTCCAATTCACATCAACAAGCATTCACACTTCTTCACCAGAGACATTTCTCTAAGAGAACAATGCTATGTGAAGAGTA
GGCCCTCTCTGCTGTCTGCGTCACCTGCTTCGGGCCCTTCACCTGCTTCGGGCCCTTCACCTGCTTCCACCAGAGACATTTCTCTAAGAGAACAATGCTATGTGAAGAGTA
AGTCAACCTGCTGACATTGGAGTGTTCCCCTTCCCACTGAGGGCAGTCGAT (continued)
```

Fig. 1C-2

SDF-1β cDNA (SEQ ID NO:70; continued)

(continued)

```
AGAGCTGTATTAAGCCACTTAAAATGTTCACTTTTGACAAAGGCAAGCACTTGTGGGTTTTGTTTTGTTTTTCATTCAGTCTTACG
AATACTTTTGCCCTTTGATTAAAGACTCCAGTTAAAAAAATTTAATGAAGAAGTGGAAAACAAGGAAGTCAAAGCAAGGAAACT
ATGTAACATGTAGGAAGTAGGAAGTAAATTATAGTGAATTGTAACTGTCTTGAATTGTAACTGTTCTTGAATTTAATAATCTGTAGGGTAAT
TAGTAACATGTGTTAAGTATTTCATAAGTGGAGCTTCAAATTGAAAAATAGAGCCTGAGGGATCTTTACTAGTTATAAAGATACAGAACT
AACAAAAATTAAAATCCTCAATCCAGCTATGTTATATTGAAAAATAGAGCCTGAGGGATCTTTACTAGTTATAAAGATACAGAACT
CTTTCAAAACCTTTTGAAATTAACCTCTCACTATACCAGTATAATTGAGTTTTCAGTGGGCAGTCATTATCCAGTAATCCAAGAT
ATTTAAAAATCTGTCACGTAGACATGGATGTACCTGCCCCCAATCCATGGAGAAAATAGATAAGAGTAGAAACTGCAG
ATGACCCTAAATCTTGACTACAGTCAGGAAAAGGAATCATTTCTATTCTCCCATGGAGAAAATAGATAAGAGTAGAAACTGCAG
GGAAAATTATTTGCATAACAATTCCTCTACTAACAATCAGTCCTTCGAATCTCTTTTGCTTTCGAACTGCTAGTCAAGTGCGTCCACGAGCTGTTT
GTCTTCCATTTGCAAGGGAAAAGTCTCCCATCTGTCCCTCCCGGGACCCTGTGCTGCCCTCGACACTCTCCTGGCTCCCGTAACCTCTTCAGAGGCC
ACTAGGGATCCCCATCTGTCGTATCAGGAGACCCAGAGAAGGGGCCAGGGCCAGAGATACCAGCGAGATAGCAGAGAAAGGTTGCAGCCTGTCGTTGTGGAGCACTCTGCTTGTTATTAGAGAT
CTCGCTGCCAGCTCTGTATCAGGAGATGAGGGCTGACACCTGTGAATAGCAGAGAAGGTGCACCTCCCCAACCTTAGATGTTCTAAGTC
GTTTGTGCTGTGGTGTCCCCTCGTCCAGGGGACTGAGAGGGGCTGAATAGCAGAGAAGGTGTATCGTCTGATGAGAATTGAGTGCTCTGATCCTCCCTGACTCATTCTGAAG
TACCTCCTGAGAAAAAGGTTCCGCTTGGACCCTTTTCCAGACCCTTTCCAGCTGATGGTGTGATCGTCTGATGAGAATTGAGTGCTCTGATCCTCCCTGACTCATTCTGAAG
TTTCCAGGTGCTACACCCTTTTCCAGCTGATGGTGTGATCGTCTGATGAGAATTGAGTGCTCTGATCCTCCCTGACTCATTCTGAAG
CTTTCCCAGGTGCTACACCCTTTTCCAGGGAATATTCCCTAGAACTTCCAAATGATGATTCAGTGTTAAATGTGATGAATATCTGTATTGATGAAATTTGTTATTT
GAGCCCCATTCCTGGAAATATTCCCTAGAACTTCCAAATGATGATTCAGTGTTAAATGTGATGAATATCTGTATTGATGAAATTTGTTATTT
TGCAACCTCGCTGACTCTCAGTCTCTGAGCAGTCTGAAATGTCCAGGAGAAGGCCAATTCCTATACGCAGCGTGCTTTAAAAATAAATAAGAAACAACTCTT
CATCTCCCAGATAATGTGAAAATGGTCCAGGAGAAGGCCAATGAAAAAATGTATATGCACTTATATAATTTCCTAATAAAGTTCTGTACTCAA
TGAGAAACAACAATTTCTACTTTGAAGTCATACCAATGAAAAAATGTATATGCACTTATATAATTTCCTAATAAAGTTCTGTACTCAA
ATGTAGCCACCAA
```

Fig. 1D

SDF-1γ cDNA (SEQ ID NO:71)

GCCGCACTTTCACTCTCCGTCAGCCGCATTGCCCGCCCCGACCCGGCCCCGCTCCGCCCCGCCCCGCC
CGGCCATGAACGCCAAGGTCGTGGTCGTGCTGGTCCTCGTGCTGACCGCGCTCTGCCTCAGCGATGGG
CTACAGATGCCCATGCCCGATTCTTGAAAGCCATGTTGCCAGAGCCAACGTCAAGCATTCTCAAACTCTGTG
CCCTTCAGATTGTAGCCCGGCTGAAGAACAAGTGCATTGACCCCGAAGCTAAAGAGATCAACCCGAAGCTAAAGAAGCAACAGAGGTGACAGCGACAGCAGCATAACAAGC
AAAGCTTTAAACAAGGGGCGCAGAAGAAGAAAGCAAAAGAAAAAGAAAAGATAGGGAAAAAGAAGAAGAAGAAAAGC
TGCCCAGAAAAGGAAAAACTAGTTATCTGCCACCTCGAGATGGACCACAGTTCACTTGCTCTCGGCGCTTTGTAAATTGCTCGAT
CCTCCTCC

Figs. 2A-2D
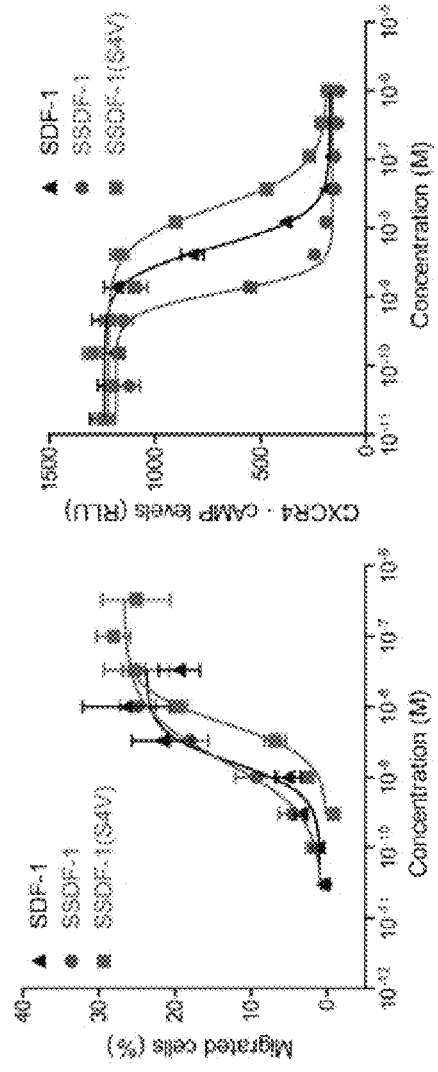
Fig. 2A
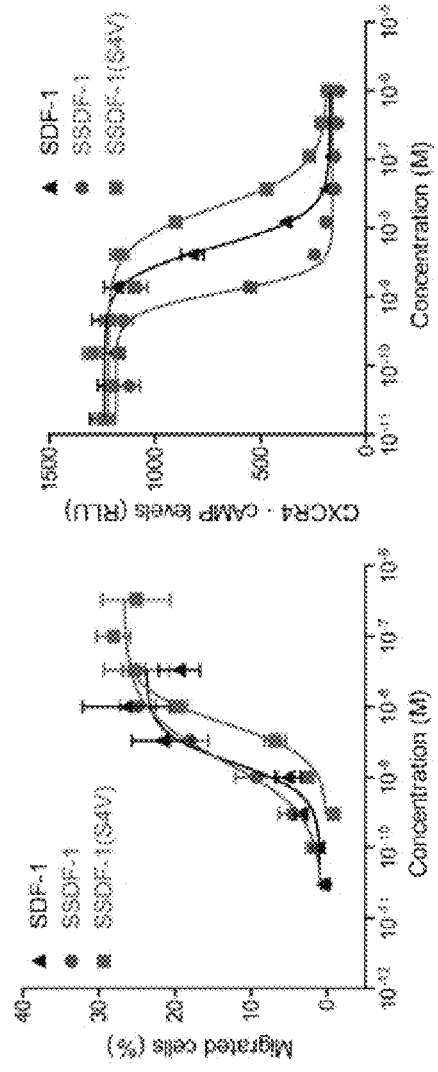
Fig. 2B
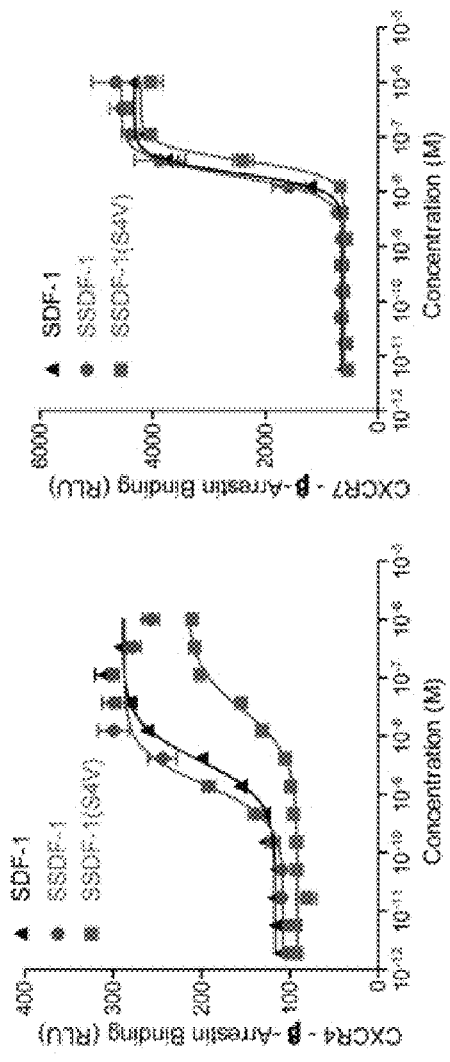
Fig. 2C
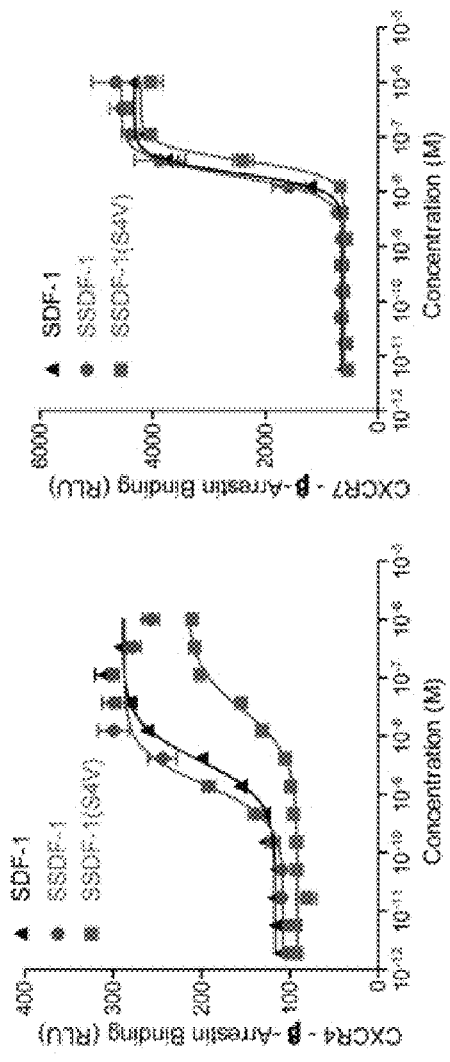
Fig. 2D Figs. 3A-3D
Fig. 3A
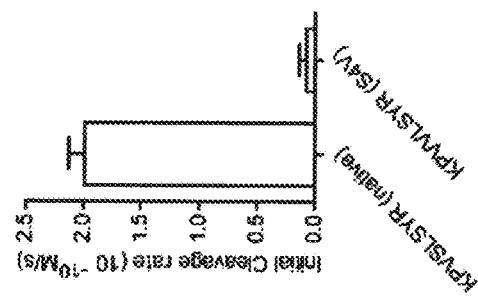
Fig. 3B
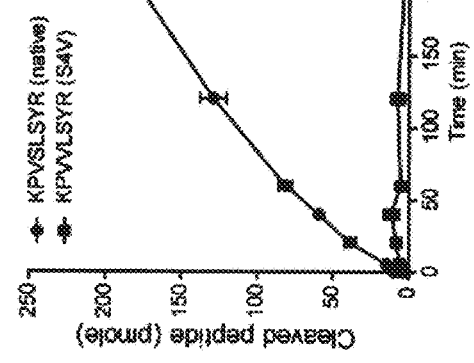
Fig. 3C
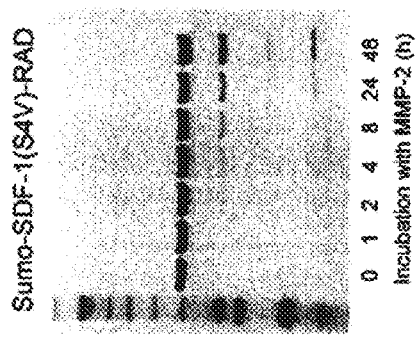
Fig. 3D
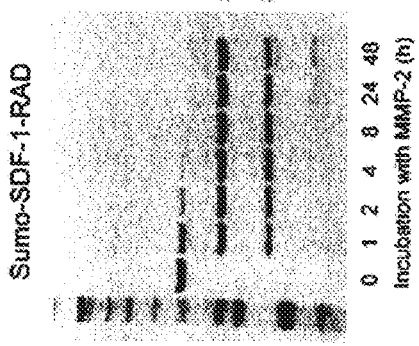

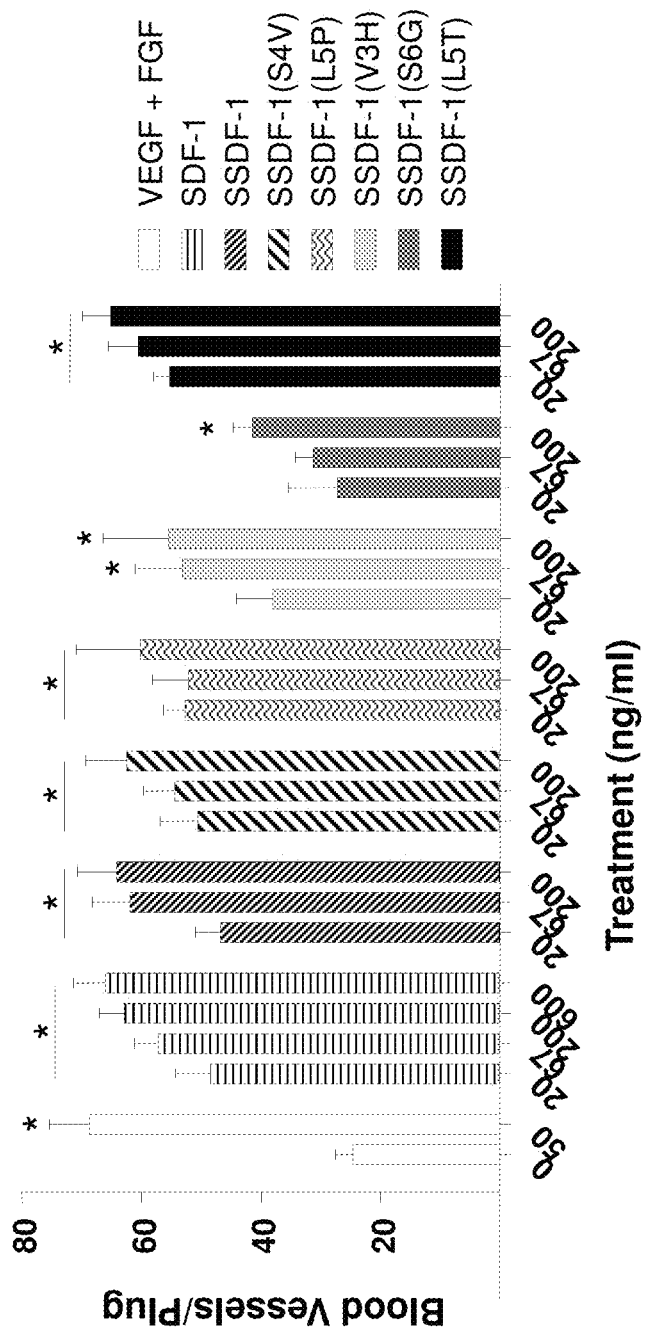

Figs. 7A-7C
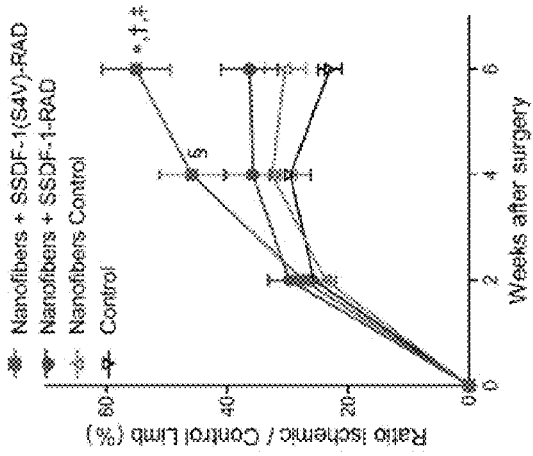
Fig. 7B
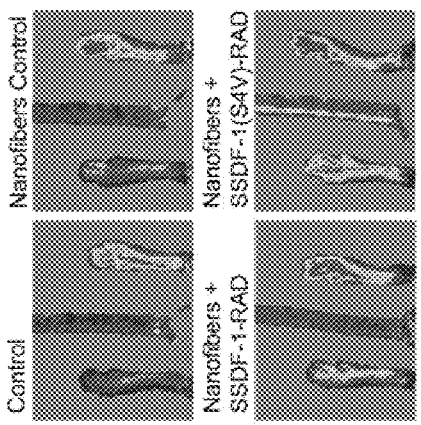
Fig. 7A
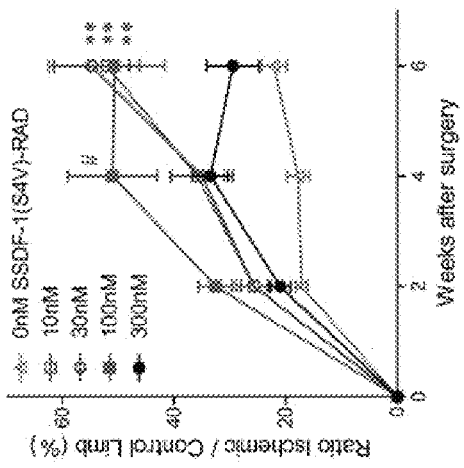
Fig. 7C

FIG. 9A

Initial cleavage rates of FRET-peptides by MMP-2

|   | V3 Mean | SEM | N | S4 Mean | SEM | N | L5 Mean | SEM | N | S6 Mean | SEM | N |
|---|---|---|---|---|---|---|---|---|---|---|---|---|
| A | 412.9 | 19.9 | 4 | 146.3 | 3.8 | 4 | 46.6 | 5.7 | 4 | 54.6 | 3.3 | 4 |
| C | *0.0* | 0.0 | 4 | *0.0* | 0.0 | 4 | *0.0* | 0.0 | 4 | *0.0* | 0.0 | 4 |
| D | *6.7* | 2.5 | 4 | 36.2 | 2.5 | 4 | *-4.7* | 2.1 | 4 | *7.1* | 3.8 | 4 |
| E | 12.9 | 0.8 | 4 | 54.2 | 3.8 | 4 | *-4.1* | 1.4 | 4 | 97.3 | 10.8 | 4 |
| F | 39.1 | 3.8 | 4 | *5.9* | 8.2 | 4 | 23.1 | 4.9 | 4 | 87.9 | 10.0 | 3 |
| G | 57.7 | 6.0 | 4 | 130.9 | 34.3 | 4 | 10.9 | 1.4 | 4 | 23.4 | 3.3 | 4 |
| H | 111.2 | 3.8 | 4 | 34.2 | 6.6 | 4 | *7.3* | 1.9 | 4 | 108.5 | 4.0 | 4 |
| I | 74.4 | 5.0 | 4 | *-3.7* | 6.7 | 4 | 34.1 | 5.4 | 4 | 141.1 | 8.6 | 4 |
| K | 103.3 | 2.1 | 4 | 12.5 | 2.1 | 4 | *4.8* | 2.6 | 4 | 89.7 | 5.6 | 4 |
| L | 174.3 | 6.6 | 4 | 16.0 | 3.9 | 4 | 100.0 | 0.0 | 4 | 64.7 | 1.5 | 4 |
| M | 87.8 | 5.0 | 4 | 30.0 | 4.3 | 4 | 54.1 | 3.8 | 4 | 108.0 | 16.0 | 4 |
| N | 48.5 | 4.5 | 4 | 203.9 | 10.1 | 4 | 10.3 | 1.8 | 4 | 65.1 | 3.7 | 4 |
| P | 12.6 | 2.2 | 4 | 322.8 | 6.1 | 4 | *-1.6* | 2.0 | 4 | 19.7 | 1.7 | 4 |
| Q | 174.5 | 5.5 | 4 | 40.0 | 0.4 | 4 | 41.0 | 3.3 | 4 | 61.1 | 5.7 | 3 |
| R | 167.4 | 9.0 | 4 | 19.3 | 3.0 | 4 | 20.5 | 1.6 | 4 | 106.8 | 17.6 | 3 |
| S | 248.2 | 12.7 | 4 | 100.0 | 0.0 | 4 | 26.9 | 7.2 | 4 | 100.0 | 0.0 | 4 |
| T | 45.7 | 2.4 | 4 | *3.5* | 2.2 | 4 | *1.5* | 2.3 | 4 | 109.9 | 11.0 | 4 |
| V | 100.0 | 0.0 | 4 | *3.3* | 2.8 | 4 | *0.0* | 0.0 | 4 | 262.5 | 21.5 | 4 |
| W | 46.1 | 6.3 | 4 | 36.3 | 2.9 | 4 | 12.6 | 4.8 | 4 | 90.3 | 6.5 | 4 |
| Y | 45.5 | 4.4 | 4 | 17.9 | 1.6 | 4 | 45.1 | 1.5 | 4 | 137.5 | 5.5 | 4 |

FIG. 9B

Initial cleavage rates of FRET-peptides by leukocyte elastase

|   | V3 Mean | SEM | N | S4 Mean | SEM | N | L5 Mean | SEM | N | S6 Mean | SEM | N |
|---|---|---|---|---|---|---|---|---|---|---|---|---|
| A | 17.4 | 0.4 | 4 | 41.6 | 1.1 | 4 | 59.4 | 1.4 | 4 | 75.5 | 1.1 | 4 |
| C | 70.4 | 12.2 | 4 | 93.3 | 1.8 | 4 | 107.7 | 9.2 | 4 | 86.6 | 2.2 | 4 |
| D | 4.0 | 1.0 | 4 | 10.9 | 0.6 | 4 | 5.0 | 0.9 | 4 | 67.1 | 1.7 | 4 |
| E | 1.9 | 1.3 | 4 | 14.8 | 1.9 | 4 | 4.0 | 0.2 | 4 | 90.2 | 2.2 | 4 |
| F | 3.7 | 0.6 | 4 | 34.9 | 3.2 | 4 | 79.2 | 2.4 | 4 | 128.6 | 0.5 | 4 |
| G | 0.6 | 0.3 | 4 | 27.8 | 0.6 | 4 | 36.2 | 1.2 | 4 | 63.3 | 1.1 | 4 |
| H | 3.6 | 0.5 | 4 | 53.6 | 0.8 | 4 | 30.4 | 1.1 | 4 | 127.8 | 3.1 | 4 |
| I | 126.6 | 3.6 | 4 | 40.7 | 4.4 | 4 | 150.5 | 3.3 | 4 | 101.5 | 1.0 | 4 |
| K | 1.9 | 0.2 | 4 | 52.6 | 1.5 | 4 | 10.0 | 0.8 | 4 | 76.6 | 1.6 | 4 |
| L | 5.4 | 0.9 | 4 | 27.1 | 2.0 | 4 | 100.0 | 0.0 | 4 | 96.8 | 0.2 | 4 |
| M | 4.2 | 0.9 | 4 | 113.7 | 5.1 | 4 | 106.5 | 3.2 | 4 | 88.3 | 1.7 | 4 |
| N | 1.4 | 0.6 | 4 | 50.3 | 0.5 | 4 | 22.2 | 1.0 | 4 | 101.1 | 1.4 | 4 |
| P | -1.6 | 0.2 | 4 | 6.7 | 0.7 | 4 | 2.4 | 0.6 | 4 | 114.1 | 1.1 | 4 |
| Q | 3.0 | 0.3 | 4 | 33.1 | 1.3 | 4 | 11.9 | 0.4 | 4 | 97.2 | 2.7 | 4 |
| R | 2.5 | 0.4 | 4 | 122.3 | 3.8 | 4 | 22.3 | 0.4 | 4 | 98.9 | 2.8 | 4 |
| S | 3.2 | 0.4 | 4 | 100.0 | 0.0 | 4 | 24.9 | 1.0 | 4 | 100.0 | 0.0 | 4 |
| T | 16.6 | 0.8 | 4 | 50.3 | 1.3 | 4 | 82.2 | 2.0 | 4 | 118.3 | 24.4 | 4 |
| V | 100.0 | 0.0 | 4 | 41.9 | 2.5 | 4 | 165.0 | 5.3 | 4 | 130.3 | 1.1 | 4 |
| W | 1.3 | 0.6 | 4 | 81.6 | 1.3 | 4 | 80.4 | 1.6 | 4 | 106.4 | 1.5 | 4 |
| Y | 1.6 | 0.5 | 4 | 51.0 | 3.4 | 4 | 134.1 | 5.1 | 4 | 145.4 | 2.5 | 4 |

FIG. 9C

Initial cleavage rates of FRET-peptides by cathepsin G

|   | V3 Mean | SEM | N | S4 Mean | SEM | N | L5 Mean | SEM | N | S6 Mean | SEM | N |
|---|---|---|---|---|---|---|---|---|---|---|---|---|
| A | *1.9* | 1.1 | 4 | 271.9 | 4.5 | 4 | 29.6 | 5.6 | 4 | 80.4 | 11.4 | 4 |
| C | 8.5 | 10.9 | 4 | 169.7 | 13.9 | 4 | -43.7 | 15.3 | 4 | 13.6 | 10.5 | 4 |
| D | 11.7 | 1.4 | 4 | 19.2 | 4.2 | 4 | -4.0 | 3.2 | 4 | 10.2 | 4.7 | 4 |
| E | 58.9 | 1.8 | 4 | 111.2 | 11.9 | 4 | *1.4* | 2.9 | 4 | 52.6 | 3.6 | 4 |
| F | 571.6 | 9.1 | 4 | 93.3 | 9.6 | 4 | 512.0 | 13.7 | 4 | 53.9 | 2.7 | 4 |
| G | 10.8 | 3.7 | 4 | 87.6 | 2.4 | 4 | 37.1 | 2.9 | 4 | *0.8* | 2.0 | 4 |
| H | 49.1 | 4.2 | 4 | 40.3 | 6.3 | 4 | *3.0* | 6.7 | 4 | 32.4 | 2.0 | 4 |
| I | 140.8 | 15.4 | 4 | 103.8 | 15.1 | 4 | 48.3 | 11.9 | 4 | 67.9 | 11.3 | 4 |
| K | 495.3 | 12.0 | 4 | 75.2 | 5.8 | 4 | 132.9 | 4.4 | 4 | 16.9 | 3.7 | 4 |
| L | 269.5 | 4.4 | 4 | 348.5 | 30.9 | 4 | 100.0 | 0.0 | 4 | 58.5 | 3.4 | 4 |
| M | 226.7 | 3.5 | 4 | 387.1 | 18.6 | 4 | 81.7 | 3.6 | 4 | 95.9 | 5.1 | 4 |
| N | 41.3 | 8.7 | 4 | 19.2 | 4.2 | 4 | *3.3* | 2.2 | 4 | 40.7 | 5.4 | 4 |
| P | *-6.0* | 5.0 | 4 | 439.4 | 2.8 | 4 | *-7.9* | 3.4 | 4 | *9.1* | 5.2 | 4 |
| Q | 20.3 | 4.8 | 4 | 102.2 | 5.2 | 4 | 18.7 | 5.3 | 4 | 28.3 | 3.2 | 4 |
| R | 39.7 | 6.6 | 4 | 46.5 | 11.8 | 4 | *-0.6* | 1.1 | 4 | 15.0 | 4.1 | 4 |
| S | 18.9 | 3.1 | 4 | 100.0 | 0.0 | 4 | *6.0* | 3.0 | 4 | 100.0 | 0.0 | 4 |
| T | 38.4 | 2.2 | 4 | 369.8 | 13.2 | 4 | *9.1* | 3.4 | 4 | 38.3 | 6.2 | 4 |
| V | 100.0 | 0.0 | 4 | 367.4 | 22.8 | 4 | 10.8 | 7.9 | 4 | 66.5 | 7.6 | 4 |
| W | 79.4 | 6.6 | 4 | 72.4 | 7.9 | 4 | 49.0 | 11.5 | 4 | 33.8 | 7.6 | 4 |
| Y | 412.2 | 10.0 | 4 | 112.9 | 15.9 | 4 | 496.8 | 29.3 | 4 | 33.5 | 5.9 | 4 |

US 10,456,451 B2

```
                         SEQUENCE LISTING

<160> NUMBER OF SEQ ID NOS: 91

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ala Lys Ala Lys Ala Glu Ala Glu Ala Lys Ala Lys Ala Glu Ala Glu
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Lys Ala Glu Ala Lys Ala Glu Ala Lys Ala Glu Ala Lys Ala Glu
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Ala Lys Ala Glu Ala Lys Ala Glu Ala Lys Ala Glu Ala Lys Ala
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Ala Glu Ala Lys Ala Glu Ala Lys Ala Glu Ala Lys Ala Glu Ala
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5
```

Ala Glu Ala Lys Ala Glu Ala Lys Ala Glu Ala Lys Ala Glu Ala Lys
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Asp Ala Asp Ala Arg Ala Arg Ala Asp Ala Asp Ala Arg Ala Arg
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Arg Ala Asp Ala Arg Ala Asp Ala Arg Ala Asp Ala Arg Ala Asp
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Ala Arg Ala Asp Ala Arg Ala Asp Ala Arg Ala Asp Ala Arg Ala
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ala Asp Ala Arg Ala Asp Ala Arg Ala Asp Ala Arg Ala Asp Ala
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Asp Ala Arg Ala Asp Ala Arg Ala Asp Ala Arg Ala Asp Ala Arg
1               5                   10                  15

<210> SEQ ID NO 11
<211> LENGTH: 16
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 11

Ala Arg Ala Asp Ala Lys Ala Glu Ala Arg Ala Asp Ala Lys Ala Glu
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Lys Ala Glu Ala Arg Ala Asp Ala Lys Ala Glu Ala Arg Ala Asp
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Arg Ala Lys Ala Asp Ala Glu Ala Arg Ala Lys Ala Asp Ala Glu
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Lys Ala Arg Ala Glu Ala Asp Ala Lys Ala Arg Ala Asp Ala Glu
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Gln Ala Gln Ala Gln Ala Gln Ala Gln Ala Gln Ala Gln Ala Gln
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Gln Val Gln Val Gln Val Gln Val Gln Val Gln Val Gln Val Gln
1               5                   10                  15

-continued

```
<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Gln Tyr Gln Tyr Gln Tyr Gln Tyr Gln Tyr Gln Tyr Gln Tyr Gln
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

His Gln His Gln His Gln His Gln His Gln His Gln His Gln His Gln
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Asn Ala Asn Ala Asn Ala Asn Ala Asn Ala Asn Ala Asn Ala Asn
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Val Asn Val Asn Val Asn Val Asn Val Asn Val Asn Val Asn Val Asn
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Tyr Asn Tyr Asn Tyr Asn Tyr Asn Tyr Asn Tyr Asn Tyr Asn Tyr Asn
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22
```

His Asn His Asn His Asn His Asn His Asn His Asn His Asn His Asn
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Asn Ala Gln Ala Asn Ala Gln Ala Asn Ala Gln Ala Asn Ala Gln
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Gln Ala Asn Ala Gln Ala Asn Ala Gln Ala Asn Ala Gln Ala Asn
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Val Asn Val Gln Val Asn Val Gln Val Asn Val Gln Val Asn Val Gln
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Val Gln Val Asn Val Gln Val Asn Val Gln Val Asn Val Gln Val Asn
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Tyr Asn Tyr Gln Tyr Asn Tyr Gln Tyr Asn Tyr Gln Tyr Asn Tyr Gln
1               5                   10                  15

<210> SEQ ID NO 28
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 28

Tyr Gln Tyr Asn Tyr Gln Tyr Asn Tyr Gln Tyr Asn Tyr Gln Tyr Asn
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

His Asn His Gln His Asn His Gln His Asn His Gln His Asn His Gln
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

His Gln His Asn His Gln His Asn His Gln His Asn His Gln His Asn
1               5                   10                  15

<210> SEQ ID NO 31
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Lys Ala Gln Ala Asp Ala Lys Ala Gln Ala Asp Ala Lys Ala Gln
1               5                   10                  15

Ala Asp

<210> SEQ ID NO 32
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Val Lys Val Gln Val Asp Val Lys Val Gln Val Asp Val Lys Val Gln
1               5                   10                  15

Val Asp

<210> SEQ ID NO 33
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33
```

-continued

Tyr Lys Tyr Gln Tyr Asp Tyr Lys Tyr Gln Tyr Asp Tyr Lys Tyr Gln
1               5                   10                  15

Tyr Asp

<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

His Lys His Gln His Asp His Lys His Gln His Asp His Lys His Gln
1               5                   10                  15

His Asp

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Ala Arg Ala Asp Ala Asp Ala Arg Ala Arg Ala Asp Ala Asp Ala
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ala Asp Ala Arg Gly Asp Ala Arg Ala Asp Ala Arg Gly Asp Ala
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ala Glu Ala Arg Ala Glu Ala Arg Ala Glu Ala Arg Ala Glu Ala
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Ala Asp Ala Lys Ala Asp Ala Lys Ala Asp Ala Lys Ala Asp Ala
1               5                   10                  15

```
<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Glu Ala Glu Ala His Ala His Ala Glu Ala Glu Ala His Ala His
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Phe Glu Phe Glu Phe Lys Phe Lys Phe Glu Phe Glu Phe Lys Phe Lys
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Leu Glu Leu Glu Leu Lys Leu Lys Leu Glu Leu Glu Leu Lys Leu Lys
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ala Glu Ala Glu Ala Lys Ala Lys Ala Glu Ala Glu Ala Lys Ala Lys
1               5                   10                  15

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Ala Glu Ala Glu Ala Glu Ala Glu Ala Lys Ala Lys
1               5                   10

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44
```

```
Lys Ala Lys Ala Lys Ala Lys Ala Glu Ala Glu Ala Glu Ala Glu Ala
1               5                   10                  15
```

<210> SEQ ID NO 45
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Ala Glu Ala Glu Ala Glu Ala Glu Ala Lys Ala Lys Ala Lys Ala Lys
1               5                   10                  15
```

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Arg Ala Arg Ala Arg Ala Arg Ala Asp Ala Asp Ala Asp Ala Asp Ala
1               5                   10                  15
```

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

```
Ala Asp Ala Asp Ala Asp Ala Asp Ala Arg Ala Arg Ala Arg Ala Arg
1               5                   10                  15
```

<210> SEQ ID NO 48
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

```
Asp Ala Asp Ala Asp Ala Asp Ala Arg Ala Arg Ala Arg Ala Arg Ala
1               5                   10                  15
```

<210> SEQ ID NO 49
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

```
His Glu His Glu His Lys His Lys His Glu His Glu His Lys His Lys
1               5                   10                  15
```

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Val Glu Val Glu Val Glu Val Glu Val Glu Val Glu Val Glu Val Glu
1               5                   10                  15

Val Glu Val Glu
            20

<210> SEQ ID NO 51
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Phe Arg Phe Arg Phe Arg Phe Arg Phe Arg Phe Arg Phe Arg Phe
1               5                   10                  15

Arg Phe Arg Phe
            20

<210> SEQ ID NO 52
<211> LENGTH: 68
<212> TYPE: PRT
<213> ORGANISM: Homo sapiens

<400> SEQUENCE: 52

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 53
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (4)..(4)
<223> OTHER INFORMATION: Ser or Val
<220> FEATURE:
<221> NAME/KEY: MOD_RES
<222> LOCATION: (5)..(5)
<223> OTHER INFORMATION: Leu, Pro, Thr or Val
<220> FEATURE:
<221> NAME/KEY: MOD_RES
<222> LOCATION: (6)..(6)
<223> OTHER INFORMATION: Any amino acid

<400> SEQUENCE: 53

Lys Pro Xaa Xaa Xaa Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
        50                  55                  60

Ala Leu Asn Lys
65

<210> SEQ ID NO 54
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Lys Pro His Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
        50                  55                  60

Ala Leu Asn Lys
65

<210> SEQ ID NO 55
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Lys Pro Cys Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
        50                  55                  60

Ala Leu Asn Lys
65

<210> SEQ ID NO 56
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Lys Pro Val Ser Thr Ser Tyr Arg Cys Pro Cys Arg Phe Phe Glu Ser

```
                1               5                   10                  15
His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gly Gly Gly Gly Gly Gly
1               5

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Ile Val Gly Pro Leu
1               5

<210> SEQ ID NO 59
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Pro Val Gly Leu Ile Gly
1               5

<210> SEQ ID NO 60
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Lys Pro Val Ser Val Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
    50                  55                  60
```

```
Ala Leu Asn Lys
65

<210> SEQ ID NO 61
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Lys Pro Val Ser Leu Cys Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 62
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Lys Pro Val Ser Leu Gly Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 63
<211> LENGTH: 72
<212> TYPE: PRT
<213> ORGANISM: Homo sapiens

<400> SEQUENCE: 63

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Arg Phe Lys Met
65                  70
```

<210> SEQ ID NO 64
<211> LENGTH: 98
<212> TYPE: PRT
<213> ORGANISM: Homo sapiens

<400> SEQUENCE: 64

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
        50                  55                  60

Ala Leu Asn Lys Gly Arg Arg Glu Glu Lys Val Gly Lys Lys Glu Lys
65                  70                  75                  80

Ile Gly Lys Lys Lys Arg Gln Lys Lys Arg Lys Ala Ala Gln Lys Arg
                85                  90                  95

Lys Asn

<210> SEQ ID NO 65
<211> LENGTH: 68
<212> TYPE: PRT
<213> ORGANISM: Homo sapiens

<400> SEQUENCE: 65

Lys Pro Val Val Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
        50                  55                  60

Ala Leu Asn Lys
65

<210> SEQ ID NO 66
<211> LENGTH: 68
<212> TYPE: PRT
<213> ORGANISM: Homo sapiens

<400> SEQUENCE: 66

Lys Pro Val Ser Pro Ser Tyr Arg Cys Pro Cys Arg Phe Phe Glu Ser
1               5                   10                  15

His Val Ala Arg Ala Asn Val Lys His Leu Lys Ile Leu Asn Thr Pro
                20                  25                  30

Asn Cys Ala Leu Gln Ile Val Ala Arg Leu Lys Asn Asn Asn Arg Gln
            35                  40                  45

Val Cys Ile Asp Pro Lys Leu Lys Trp Ile Gln Glu Tyr Leu Glu Lys
        50                  55                  60

Ala Leu Asn Lys
65

<210> SEQ ID NO 67
<211> LENGTH: 68
<212> TYPE: PRT
<213> ORGANISM: Homo sapiens

<400> SEQUENCE: 67

Lys Pro Val Val Pro Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 68
<211> LENGTH: 68
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (6)..(6)
<223> OTHER INFORMATION: Any amino acid

<400> SEQUENCE: 68

Lys Pro Xaa Ser Leu Xaa Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys
65

<210> SEQ ID NO 69
<211> LENGTH: 1940
<212> TYPE: DNA
<213> ORGANISM: Homo sapiens

<400> SEQUENCE: 69
gccgcacttt cactctccgt cagccgcatt gcccgctcgg cgtccggccc ccgacccgcg      60
ctcgtccgcc cgcccgcccg cccgcccgcg ccatgaacgc caaggtcgtg gtcgtgctgg     120
tcctcgtgct gaccgcgctc tgcctcagcg acggaagcc cgtcagcctg agctacagat     180
gcccatgccg attcttcgaa agccatgttg ccagagccaa cgtcaagcat ctcaaaattc     240
tcaacactcc aaactgtgcc cttcagattg tagcccggct gaagaacaac aacagacaag     300
tgtgcattga cccgaagcta aagtggattc aggagtacct ggagaaagct ttaaacaagt     360
aagcacaaca gccaaaaagg actttccgct agacccactc gaggaaaact aaaaccttgt     420
gagagatgaa agggcaaaga cgtggggag ggggccttaa ccatgaggac caggtgtgtg     480
tgtggggtgg gcacattgat ctgggatcgg gcctgaggtt tgccagcatt agaccctgc     540 atttatagca tacggtatga tattgcagct tatattcatc catgccctgt acctgtgcac     600

| | | |
|---|---|---|
| gttggaactt ttattactgg ggttttttcta agaaagaaat tgtattatca acagcatttt | 660 |
| caagcagtta gttccttcat gatcatcaca atcatcatca ttctcattct cattttttaa | 720 |
| atcaacgagt acttcaagat ctgaatttgg cttgtttgga gcatctcctc tgctcccctg | 780 |
| gggagtctgg gcacagtcag gtggtggctt aacagggagc tggaaaaagt gtcctttctt | 840 |
| cagacactga ggctcccgca gcagcgcccc tcccaagagg aaggcctctg tggcactcag | 900 |
| ataccgactg gggctgggcg ccgccactgc cttcacctcc tctttcaacc tcagtgattg | 960 |
| gctctgtggg ctccatgtag aagccactat tactgggact gtgctcagag acccctctcc | 1020 |
| cagctattcc tactctctcc ccgactccga gagcatgctt aatcttgctt ctgcttctca | 1080 |
| tttctgtagc ctgatcagcg ccgcaccagc cgggaagagg gtgattgctg gggctcgtgc | 1140 |
| cctgcatccc tctcctccca gggcctgccc acagctcgg gccctctgtg agatccgtct | 1200 |
| ttggcctcct ccagaatgga gctggccctc tcctggggat gtgtaatggt ccccctgctt | 1260 |
| acccgcaaaa gacaagtctt tacagaatca atgcaattt taaatctgag agctcgcttt | 1320 |
| gagtgactgg gttttgtgat tgcctctgaa gcctatgtat gccatggagg cactaacaaa | 1380 |
| ctctgaggtt tccgaaatca gaagcgaaaa aatcagtgaa taaaccatca tcttgccact | 1440 |
| accccctcct gaagccacag cagggtttca ggttccaatc agaactgttg gcaaggtgac | 1500 |
| atttccatgc ataaatgcga tccacagaag gtcctggtgg tatttgtaac ttttgcaag | 1560 |
| gcatttttt atatatattt ttgtgcacat tttttttac gtttctttag aaaacaaatg | 1620 |
| tatttcaaaa tatatttata gtcgaacaat tcatatattt gaagtggagc catatgaatg | 1680 |
| tcagtagttt atacttctct attatctcaa actactggca atttgtaaag aaatatatat | 1740 |
| gatatataaa tgtgattgca gcttttcaat gttagccaca gtgtattttt tcacttgtac | 1800 |
| taaaattgta tcaaatgtga cattatatgc actagcaata aatgctaat tgtttcatgg | 1860 |
| tataaacgtc ctactgtatg tgggaattta tttacctgaa ataaaattca ttagttgtta | 1920 |
| gtgatggagc ttaaaaaaaa | 1940 |

<210> SEQ ID NO 70
<211> LENGTH: 3545
<212> TYPE: DNA
<213> ORGANISM: Homo sapiens

<400> SEQUENCE: 70

| | | |
|---|---|---|
| gccgcacttt cactctccgt cagccgcatt gcccgctcgg cgtccggccc ccgacccgcg | 60 |
| ctcgtccgcc cgcccgcccg cccgcccgcg ccatgaacgc caaggtcgtg gtcgtgctgg | 120 |
| tcctcgtgct gaccgcgctc tgcctcagcg acggaagcc cgtcagcctg agctacagat | 180 |
| gcccatgccg attcttcgaa agccatgttc cagagccaa cgtcaagcat ctcaaaattc | 240 |
| tcaacactcc aaactgtgcc cttcagattg tagcccggct gaagaacaac aacagacaag | 300 |
| tgtgcattga cccgaagcta aagtggattc aggagtacct ggagaaagct ttaaacaaga | 360 |
| ggttcaagat gtgagagggt cagacgcctg aggaacccttt acagtaggag cccagctctg | 420 |
| aaaccagtgt tagggaaggg cctgccacag cctcccctgc cagggcaggg cccaggcat | 480 |
| tgccaagggc tttgttttgc acactttgcc atatttcac catttgatta tgtagcaaaa | 540 |
| tacatgacat ttattttca tttagtttga ttattcagtg tcactggcga cacgtagcag | 600 |
| cttagactaa ggccattatt gtacttgcct tattagagtg tctttccacg gagccactcc | 660 |
| tctgactcag ggctcctggg ttttgtattc tctgagctgt gcaggtgggg agactgggct | 720 |
| gagggagcct ggccccatgg tcagccctag ggtggagagc caccaagagg gacgcctggg | 780 |

```
ggtgccagga ccagtcaacc tgggcaaagc ctagtgaagg cttctctctg tgggatggga    840
tggtggaggg ccacatggga ggctcacccc cttctccatc cacatgggag ccgggtctgc    900
ctcttctggg agggcagcag ggctaccctg agctgaggca gcagtgtgag gccagggcag    960
agtgagaccc agccctcatc ccgagcacct ccacatcctc cacgttctgc tcatcattct   1020
ctgtctcatc catcatcatg tgtgtccacg actgtctcca tggccccgca aaaggactct   1080
caggaccaaa gctttcatgt aaactgtgca ccaagcagga aatgaaaatg tcttgtgtta   1140
cctgaaaaca ctgtgcacat ctgtgtcttg tttggaatat tgtccattgt ccaatcctat   1200 gttttttgttc aaagccagcg tcctcctctg tgaccaatgt cttgatgcat gcactgttcc   1260
ccctgtgcag ccgctgagcg aggagatgct ccttgggccc tttgagtgca gtcctgatca   1320
gagccgtggt cctttggggt gaactacctt ggttccccca ctgatcacaa aaacatggtg   1380
ggtccatggg cagagcccaa gggaattcgg tgtgcaccag ggttgacccc agaggattgc   1440
tgccccatca gtgctccctc acatgtcagt accttcaaac tagggccaag cccagcactg   1500
cttgaggaaa acaagcattc acaacttgtt tttggttttt aaacccagt ccacaaaata    1560 accaatcctg gacatgaaga ttcttttccca attcacatct aacctcatct tcttcaccat   1620
ttggcaatgc catcatctcc tgccttcctc ctgggccctc tctgctctgc gtgtcacctg   1680
tgcttcgggc ccttcccaca ggacatttct ctaagagaac aatgtgctat gtgaagagta   1740
agtcaacctg cctgacattt ggagtgttcc ccttccactg agggcagtcg atagagctgt   1800
attaagccac ttaaaatgtt cacttttgac aaaggcaagc acttgtgggt ttttgttttg   1860
tttttcattc agtcttacga atacttttgc cctttgatta aagactccag ttaaaaaaaa   1920
ttttaatgaa gaaagtggaa acaaggaag tcaaagcaag gaaactatgt aacatgtagg    1980
aagtaggaag taaattatag tgatgtaatc ttgaattgta actgttcttg aatttaataa   2040
tctgtagggt aattagtaac atgtgttaag tattttcata agtatttcaa attggagctt   2100
catggcagaa ggcaaaccca tcaacaaaaa ttgtccctta aacaaaaatt aaaatcctca   2160
atccagctat gttatattga aaaaatagag cctgagggat ctttactagt tataaagata   2220
cagaactctt tcaaaacctt tgaaattaa cctctcacta taccagtata attgagtttt    2280
cagtggggca gtcattatcc aggtaatcca agatatttta aaatctgtca cgtagaactt   2340
ggatgtacct gccccaatc catgaaccaa gaccattgaa ttcttggttg aggaaacaaa    2400 catgaccta aatcttgact acagtcagga aaggaatcat ttctatttct cctccatggg   2460
agaaaataga taagagtaga aactgcaggg aaaattattt gcataacaat tcctctacta   2520
acaatcagct ccttcctgga gactgcccag ctaaagcaat atgcatttaa atacagtctt   2580
ccatttgcaa gggaaaagtc tcttgtaatc cgaatctctt tttgctttcg aactgctagt   2640
caagtgcgtc cacgagctgt ttactaggga tccctcatct gtccctccgg gacctggtgc   2700
tgcctctacc tgacactccc ttgggctccc tgtaacctct tcagaggccc tcgctgccag   2760
ctctgtatca ggacccagag gaagggcca gaggctcgtt gactggctgt gtgttgggat    2820
tgagtctgtg ccacgtgttt gtgctgtggt gtgtccccct ctgtccaggc actgagatac   2880
cagcgaggag gctccagagg gcactctgct tgttattaga gattacctcc tgagaaaaaa   2940
ggttccgctt ggagcagagg ggctgaatag cagaaggttg cacctccccc aaccttagat   3000
gttctaagtc tttccattgg atctcattgg acccttccat ggtgtgatcg tctgactggt   3060
gttatcaccg tgggctccct gactgggagt tgatcgcctt tcccaggtgc tacacccttt   3120
```

```
tccagctgga tgagaatttg agtgctctga tccctctaca gagcttccct gactcattct    3180
gaaggagccc cattcctggg aaatattccc tagaaacttc caaatcccct aagcagacca    3240
ctgataaaac catgtagaaa atttgttatt ttgcaacctc gctggactct cagtctctga    3300
gcagtgaatg attcagtgtt aaatgtgatg aatactgtat tttgtattgt ttcaattgca    3360
tctcccagat aatgtgaaaa tggtccagga gaaggccaat tcctatacgc agcgtgcttt    3420
aaaaaataaa taagaaacaa ctctttgaga acaacaatt tctactttga agtcatacca    3480
atgaaaaaat gtatatgcac ttataatttt cctaataaag ttctgtactc aaatgtagcc    3540
accaa                                                               3545
```

<210> SEQ ID NO 71
<211> LENGTH: 524
<212> TYPE: DNA
<213> ORGANISM: Homo sapiens

<400> SEQUENCE: 71

```
gccgcacttt cactctccgt cagccgcatt gcccgctcgg cgtccggccc ccgacccgcg     60
ctcgtccgcc cgcccgcccg cccgcccgcg ccatgaacgc caaggtcgtg gtcgtgctgg    120
tcctcgtgct gaccgcgctc tgcctcagcg acgggaagcc cgtcagcctg agctacagat    180
gcccatgccg attcttcgaa agccatgttg ccagagccaa cgtcaagcat ctcaaaattc    240
tcaacactcc aaactgtgcc cttcagattg tagcccggct gaagaacaac aacagacaag    300
tgtgcattga cccgaagcta agtggattc aggagtacct ggagaaagct ttaaacaagg    360
ggcgcagaga agaaaagtg gggaaaaaag aaaagatagg aaaaaagaag cgacagaaga    420
agagaaaggc tgcccagaaa aggaaaaact agttatctgc cacctcgaga tggaccacag    480
ttcacttgct ctcggcgctt tgtaaatttg ctcgatcctc ctcc                     524
```

<210> SEQ ID NO 72
<211> LENGTH: 276
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72

```
agcaagccgg tcagcctgag ctaccgttgc ccatgccgtt tcttcgaaag ccatgttgcc     60
cgcgccaacg tcaagcatct caaaattctc aacactccaa actgtgccct tcagattgta    120
gcccgtctga gaacaacaa ccgccaagtg tgcattgacc cgaagctgaa gtggattcag    180
gagtacctgg agaaagcttt aaacaaggga ggcggggag gtgggcgtgc cgacgctcgc    240
gcagatgcgc gtgccgacgc tcgggcagat gcgtga                              276
```

<210> SEQ ID NO 73
<211> LENGTH: 91
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 73

```
Ser Lys Pro Val Ser Leu Ser Tyr Arg Cys Pro Cys Arg Phe Phe Glu
1               5                   10                  15

Ser His Val Ala Arg Ala Asn Val Lys His Leu Lys Ile Leu Asn Thr
            20                  25                  30
```

Pro Asn Cys Ala Leu Gln Ile Val Ala Arg Leu Lys Asn Asn Asn Arg
         35                  40                  45

Gln Val Cys Ile Asp Pro Lys Leu Lys Trp Ile Gln Glu Tyr Leu Glu
 50                  55                  60

Lys Ala Leu Asn Lys Gly Gly Gly Gly Gly Arg Ala Asp Ala Arg
 65                  70                  75                  80

Ala Asp Ala Arg Ala Asp Ala Arg Ala Asp Ala
             85                  90

<210> SEQ ID NO 74
<211> LENGTH: 276
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
agcaagccgg tcgtcctgag ctaccgttgc ccatgccgtt tcttcgaaag ccatgttgcc    60
cgcgccaacg tcaagcatct caaaattctc aacactccaa actgtgccct tcagattgta   120
gcccgtctga gaacaacaa ccgccaagtg tgcattgacc cgaagctgaa gtggattcag    180
gagtacctgg agaaagcttt aaacaaggga ggcggggag gtgggcgtgc cgacgctcgc    240
gcagatgcgc gtgccgacgc tcgggcagat gcgtga                            276

<210> SEQ ID NO 75
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Ser Lys Pro Val Val Leu Ser Tyr Arg Cys Pro Cys Arg Phe Phe Glu
 1               5                  10                  15

Ser His Val Ala Arg Ala Asn Val Lys His Leu Lys Ile Leu Asn Thr
             20                  25                  30

Pro Asn Cys Ala Leu Gln Ile Val Ala Arg Leu Lys Asn Asn Asn Arg
         35                  40                  45

Gln Val Cys Ile Asp Pro Lys Leu Lys Trp Ile Gln Glu Tyr Leu Glu
 50                  55                  60

Lys Ala Leu Asn Lys Gly Gly Gly Gly Gly Arg Ala Asp Ala Arg
 65                  70                  75                  80

Ala Asp Ala Arg Ala Asp Ala Arg Ala Asp Ala
             85                  90

<210> SEQ ID NO 76
<211> LENGTH: 207
<212> TYPE: DNA
<213> ORGANISM: Homo sapiens

<400> SEQUENCE: 76
aagcccgtca gcctgagcta cagatgccca tgccgattct cgaaagcca tgttgccaga    60 gccaacgtca gcatctcaa aattctcaac actccaaact gtgcccttca gattgtagcc   120
cggctgaaga caacaacag acaagtgtgc attgacccga agctaaagtg gattcaggag   180
tacctggaga aagctttaaa caagtga                                      207

<210> SEQ ID NO 77
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
aagccggtca gcctgagcta ccgttgccca tgccgtttct tcgaaagcca tgttgcccgc      60
gccaacgtca agcatctcaa aattctcaac actccaaact gtgcccttca gattgtagcc     120
cgtctgaaga acaacaaccg ccaagtgtgc attgacccga agctgaagtg gattcaggag     180
tacctggaga aagcttttaaa caagtga                                        207

<210> SEQ ID NO 78
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
agcaagccgg tcagcctgag ctaccgttgc ccatgccgtt tcttcgaaag ccatgttgcc      60
cgcgccaacg tcaagcatct caaaattctc aacactccaa actgtgccct tcagattgta     120
gcccgtctga agaacaacaa ccgccaagtg tgcattgacc cgaagctgaa gtggattcag     180
gagtacctgg agaaagcttt aaacaagtga                                      210

<210> SEQ ID NO 79
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79
aagccggtcg tcctgagcta ccgttgccca tgccgtttct tcgaaagcca tgttgcccgc      60
gccaacgtca agcatctcaa aattctcaac actccaaact gtgcccttca gattgtagcc     120
cgtctgaaga acaacaaccg ccaagtgtgc attgacccga agctgaagtg gattcaggag     180
tacctggaga aagcttttaaa caagtga                                        207

<210> SEQ ID NO 80
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80
agcaagccgg tcgtcctgag ctaccgttgc ccatgccgtt tcttcgaaag ccatgttgcc      60
cgcgccaacg tcaagcatct caaaattctc aacactccaa actgtgccct tcagattgta     120
gcccgtctga agaacaacaa ccgccaagtg tgcattgacc cgaagctgaa gtggattcag     180
gagtacctgg agaaagcttt aaacaagtga                                      210

<210> SEQ ID NO 81
<211> LENGTH: 48

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
cgtgccgacg ctcgcgcaga tgcgcgtgcc gacgctcggg cagatgcg                    48

<210> SEQ ID NO 82
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
cgtgcccgtg ccgacgccga cgcccgtgcc cgtgccgacg ccgacgcc                    48

<210> SEQ ID NO 83
<211> LENGTH: 306
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83
```

Ser Lys Pro Val Val Leu Ser Tyr Arg Cys Pro Cys Arg Phe Phe Glu
1               5                   10                  15

Ser His Val Ala Arg Ala Asn Val Lys His Leu Lys Ile Leu Asn Thr
            20                  25                  30

Pro Asn Cys Ala Leu Gln Ile Val Ala Arg Leu Lys Asn Asn Asn Arg
        35                  40                  45

Gln Val Cys Ile Asp Pro Lys Leu Lys Trp Ile Gln Glu Tyr Leu Glu
    50                  55                  60

Lys Ala Leu Asn Lys Gly Gly Gly Ser Val Asp Lys Thr His Thr
65                  70                  75                  80

Cys Pro Pro Cys Pro Ala Pro Glu Leu Leu Gly Gly Pro Ser Val Phe
                85                  90                  95

Leu Phe Pro Pro Lys Pro Lys Asp Thr Leu Met Glu Thr Ile Ser Arg
            100                 105                 110

Thr Pro Glu Val Thr Cys Val Val Asp Val Ser His Glu Asp Pro
        115                 120                 125

Glu Val Lys Phe Asn Trp Tyr Val Asp Gly Val Glu Val His Asn Ala
    130                 135                 140

Lys Thr Lys Pro Arg Glu Glu Gln Tyr Asn Ser Thr Tyr Arg Val Val
145                 150                 155                 160

Ser Val Leu Thr Val Leu His Gln Asp Trp Leu Asn Gly Lys Glu Tyr
                165                 170                 175

Lys Cys Lys Val Ser Asn Lys Ala Leu Pro Ala Pro Ile Glu Lys Thr
            180                 185                 190

Ile Ser Lys Ala Lys Gly Gln Pro Arg Glu Pro Gln Val Tyr Thr Leu
        195                 200                 205

Pro Pro Ser Arg Asp Glu Leu Thr Lys Asn Gln Val Ser Leu Thr Cys
    210                 215                 220

Leu Val Lys Gly Phe Tyr Pro Ser Asp Ile Ala Val Glu Trp Glu Ser
225                 230                 235                 240

```
Asn Gly Gln Pro Glu Asn Asn Tyr Lys Thr Thr Pro Pro Val Leu Asp
                245                 250                 255

Ser Asp Gly Ser Phe Phe Leu Tyr Ser Lys Leu Thr Val Asp Lys Ser
            260                 265                 270

Arg Trp Gln Gln Gly Asn Val Phe Ser Cys Ser Val Met Glu Thr His
        275                 280                 285

Glu Ala Leu His Asn His Tyr Thr Gln Lys Ser Leu Ser Leu Ser Pro
    290                 295                 300

Gly Lys
305

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Gly Gly Gly Ser
1               5

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Phe Lys Met
1

<210> SEQ ID NO 86
<211> LENGTH: 89
<212> TYPE: PRT
<213> ORGANISM: Homo sapiens

<400> SEQUENCE: 86

Met Asn Ala Lys Val Val Val Leu Val Leu Val Leu Thr Ala Leu
1               5                   10                  15

Cys Leu Ser Asp Gly Lys Pro Val Ser Leu Ser Tyr Arg Cys Pro Cys
                20                  25                  30

Arg Phe Phe Glu Ser His Val Ala Arg Ala Asn Val Lys His Leu Lys
            35                  40                  45

Ile Leu Asn Thr Pro Asn Cys Ala Leu Gln Ile Val Ala Arg Leu Lys
        50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys
                85

<210> SEQ ID NO 87
<211> LENGTH: 93
<212> TYPE: PRT
<213> ORGANISM: Homo sapiens

<400> SEQUENCE: 87

Met Asn Ala Lys Val Val Val Leu Val Leu Val Leu Thr Ala Leu
1               5                   10                  15
```

```
Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Arg Phe Lys Met
                85                  90

<210> SEQ ID NO 88
<211> LENGTH: 119
<212> TYPE: PRT
<213> ORGANISM: Homo sapiens

<400> SEQUENCE: 88

Met Asn Ala Lys Val Val Val Val Leu Val Leu Val Leu Thr Ala Leu
1               5                   10                  15

Cys Leu Ser Asp Gly Lys Pro Val Ser Leu Ser Tyr Arg Cys Pro Cys
            20                  25                  30

Arg Phe Phe Glu Ser His Val Ala Arg Ala Asn Val Lys His Leu Lys
        35                  40                  45

Ile Leu Asn Thr Pro Asn Cys Ala Leu Gln Ile Val Ala Arg Leu Lys
    50                  55                  60

Asn Asn Asn Arg Gln Val Cys Ile Asp Pro Lys Leu Lys Trp Ile Gln
65                  70                  75                  80

Glu Tyr Leu Glu Lys Ala Leu Asn Lys Gly Arg Arg Glu Glu Lys Val
                85                  90                  95

Gly Lys Lys Glu Lys Ile Gly Lys Lys Lys Arg Gln Lys Lys Arg Lys
            100                 105                 110

Ala Ala Gln Lys Arg Lys Asn
            115

<210> SEQ ID NO 89
<211> LENGTH: 8
<212> TYPE: PRT
<213> ORGANISM: Homo sapiens

<400> SEQUENCE: 89

Lys Pro Val Ser Leu Ser Tyr Arg
1               5

<210> SEQ ID NO 90
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx

<400> SEQUENCE: 90

Xaa Arg Ala Arg Ala Asp Ala Asp Ala Arg Ala Arg Ala Asp Ala Asp
1               5                   10                  15

Ala
```

```
<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Lys Pro Val Val Leu Ser Tyr Arg
1               5
```

PROTEASE-RESISTANT MUTANTS OF STROMAL CELL DERIVED FACTOR-1 IN THE REPAIR OF TISSUE DAMAGE

CROSS-REFERENCE TO RELATED APPLICATIONS

This application claims the benefit of the filing date of U.S. provisional application No. 61/308,090, filed Feb. 25, 2010, and 61/345,852, filed May 18, 2010, each of which is herein incorporated by reference.

SEQUENCE LISTING

The instant application contains a Sequence Listing which has been submitted in ASCII format via EFS-Web and is hereby incorporated by reference in its entirety. Said ASCII copy, created on Aug. 5, 2016, is named "50591 004004 Sequence Listing.txt" and is 46,633 bytes in size.

BACKGROUND OF THE INVENTION

In general, the invention relates to protease-resistant mutants of stromal cell derived factor-1 (SDF-1).

DF-1 (also known as CXCL12) is a 68 amino acid member of the chemokine family that is a chemoattractant for resting T-lymphocytes, monocytes, and CD34+ stem cells. SDF-1 is produced in multiple forms: SDF-1α (CXCL12a), SDF-1β (CXCL12b), and SDF-1γ, which are the result of differential mRNA splicing. The sequences of SDF-1α and SDF-1β are essentially the same, except that SDF-1β is extended by four amino acids (Arg-Phe-Lys-Met (SEQ ID NO: 85)) at the C-terminus. The first three exons of SDF-1γ are identical to those of SDF-1α and SDF-1β. The fourth exon of SDF-1γ is located 3200 base-pairs downstream from the third exon on the SDF-1 locus and lies between the third exon and the fourth exon of SDF-1β. SDF-1 is initially made with a signal peptide (21 amino acids in length) that is cleaved to make the active peptide.

SDF-1 plays a key-role in the homing of hematopoietic stem cells to bone marrow during embryonic development and after stem cell transplantation. In addition to its role in stem cell homing, SDF-1 is also important in cardiogenesis and vasculogenesis. SDF-1-deficient mice die perinatally and have defects in cardiac ventricular septal formation, bone marrow hematopoiesis, and organ-specific vasculogenesis. It has also been reported that abnormally low levels of SDF-1 are at least partially responsible for impaired wound healing associated with diabetic patients and that impairment can be reversed by the administration of SDF-1 at the site of tissue damage.

In the normal adult heart, SDF-1 is expressed constitutively, but expression is upregulated within days after myocardial infarction. It has been shown previously that SDF-1 expression increased eight weeks after myocardial infarction by intramyocardial transplantation of stably transfected cardiac fibroblasts overexpressing SDF-1, in combination with G-CSF therapy. This procedure was associated with higher numbers of bone marrow stem cells (c-Kit or CD34+) and endothelial cells in the heart and resulted in an increase of vascular density and an improvement of left ventricular function. These studies suggest that the insufficiency of the naturally-occurring myocardial repair process may be, in part, due to inadequate SDF-1 availability. Hence, the delivery of SDF-1 in a controlled manner after myocardial infarction may attract more progenitor cells and thereby promote tissue repair.

There exists a need in the art for methods and compositions that promote wound healing and tissue repair.

SUMMARY OF THE INVENTION

The present invention is directed to stromal cell derived factor-1 (SDF-1) peptides that have been mutated in a manner that preserves their ability to function as chemoattractants, but renders them resistant to inactivation by proteases, particularly matrix metalloproteinase-2 (MMP-2), matrix metalloproteinase-9 (MMP-9), dipeptidyl peptidase IV (DPPIV/CD26), leukocyte elastase, cathepsin G, carboxypeptidase M, and carboxypeptidase N. Such peptides may be useful in the treatment of, for example, peripheral vascular disease (PVD; also known as peripheral artery disease (PAD) or peripheral artery occlusive disease (PAOD)); myocardial infarction; ulcers in the gastrointestinal tract or elsewhere; wounds resulting from accident, surgery, or disease; tissue damage; or cardiac tissue damaged as a result of myocardial infarction or other cardiovascular event. The peptides of the present invention may also be useful in treating or reducing the likelihood of tissue damage caused by wounds, ulcers, or lesions in diabetic patients.

Accordingly, in one aspect, the invention features an isolated mutant form of SDF-1 peptide (mSDF-1) or $X_p$-mSDF-1, wherein mSDF-1 is a peptide that includes the amino acid sequence of at least amino acids 1-8 of SEQ ID NO:53 and which may be extended at the C-terminus by all or any portion of the remaining amino acid sequence of SEQ ID NO:53. SEQ ID NO:53 has the following amino acid sequence:

K P $X_3$ $X_4$ $X_5$ $X_6$ Y R C P C R F F E S H V A R A N V K H L K I L N T P N C A L Q I V A R L K N N N R Q V C I D P K L K W I Q E Y L E K A L N K, wherein $X_3$ is any amino acid;
$X_4$ is serine or valine;
$X_5$ is leucine, proline, threonine, or valine; and
$X_6$ is any amino acid residue.

Excluded from the invention of the first aspect are peptides with an amino acid sequence of at least amino acids 1-8 of SEQ ID NO:52 or SEQ ID NOs:65-67.

The isolated mSDF-1 or $X_p$-mSDF-1 peptide of the first aspect may include SDF(V3H) (SEQ ID NO:54), SDF(V3C) (SEQ ID NO:55), SDF(L5T) (SEQ ID NO:56), SDF(L5V) (SEQ ID NO:60), SDF(S6C) (SEQ ID NO:61), or SDF (S6G) (SEQ ID NO:62).

In a second aspect, the invention features an isolated mSDF-1 or $X_p$-mSDF-1 peptide, wherein SDF-1 includes the amino acid sequence of at least amino acids 1-8 of SEQ ID NO:68 and may be extended at the C-terminus by all or any portion of the remaining sequence of SEQ ID NO:68. SEQ ID NO:68 has the following amino acid sequence:

K P $X_3$ S L $X_6$ Y R C P C R F F E S H V A R A N V K H L K I L N T P N C A L Q I V A R L K N N N R Q V C I D P K L K W I Q E Y L E K A L N K, wherein $X_3$ and $X_6$ are any amino acid.

Excluded from the invention of the second aspect are peptides with an amino acid sequence of at least amino acids 1-8 of SEQ ID NO:52.

In one embodiment of the second aspect, $X_3$ is valine and $X_6$ is any amino acid residue. In another embodiment of the second aspect, $X_3$ is any amino acid residue and $X_6$ is serine.

Peptides of the first or second aspect that have been mutated by the addition of amino acids at the N-terminus are abbreviated $X_p$-mSDF-1, where X is a proteinogenic amino acid(s) (e.g., serine) or a protease protective organic group and p is any integer from 1 to 4 (e.g., 1). In each embodiment of the first and second aspects, mSDF-1 maintains chemoattractant activity for T cells and is inactivated by MMP-2, MMP-9, leukocyte elastase, and/or cathepsin G at a rate that is at least 50% less than the rate of inactivation of native SDF-1, and $X_p$-mSDF-1 maintains chemoattractant activity for T cells, is inactivated by DPPIV at a rate that is at least 50% less than the rate at which native SDF-1 is inactivated, and is inactivated by MMP-2, MMP-9, leukocyte elastase, and/or cathepsin G at a rate that is at least 50% less than the rate of inactivation of native SDF-1.

In a third aspect, the invention features an isolated SDF-1-$Y_z$, $X_p$-SDF-1-$Y_z$ mSDF-1-$Y_z$ or $X_p$-mSDF-1-$Y_z$ peptide, wherein mSDF-1 includes the amino acid sequence of SEQ ID NO:65, SEQ ID NO:66, or SEQ ID NO:67, wherein a) $X_p$ is a proteinogenic amino acid(s) or a protease protective organic group and p is any integer from 1 to 4; and b) $Y_z$ is a proteinogenic amino acid(s) and z is any integer from 1 to 4.

In each embodiment of the third aspect, mSDF-1-$Y_z$ maintains chemoattractant activity for T cells and is inactivated by MMP-2, MMP-9, leukocyte elastase, cathepsin G, carboxypeptidase M, and/or carboxypeptidase N at a rate that is at least 50% less than the rate of inactivation of native SDF-1, and $X_p$-mSDF-1-$Y_z$ maintains chemoattractant activity for T cells, is inactivated by DPPIV at a rate that is at least 50% less than the rate at which native SDF-1 is inactivated, and is inactivated by MMP-2, MMP-9, leukocyte elastase, cathepsin G, carboxypeptidase M, and/or carboxypeptidase N at a rate that is at least 50% less than the rate of inactivation of native SDF-1. In certain embodiments of the third aspect, X is a serine and p is 1 when the isolated mSDF-1-$Y_z$ peptide is $X_p$-mSDF-1-$Y_z$. In some embodiments, Y is a serine and z is 1.

In one embodiment, the invention features an isolated mSDF-1-$Y_z$ or $X_p$-mSDF-1-$Y_z$ peptide, wherein SDF-1 includes the amino acid sequence of SEQ ID NO:65, SEQ ID NO:66, or SEQ ID NO:67. The SDF-1 peptide of this aspect may also include SDF(V3H) (SEQ ID NO:54), SDF (V3C) (SEQ ID NO:55), SDF(L5T) (SEQ ID NO:56), SDF(L5V) (SEQ ID NO:60), SDF(S6C) (SEQ ID NO:61), or SDF(S6G) (SEQ ID NO:62). In addition, C-terminal modifications may be made to any of the mSDF-1 peptides described herein.

In a fourth aspect, the invention features a fusion protein having the formula: A-(L)$_n$-(R)$_q$, wherein: A is isolated mSDF-1, $X_p$-mSDF-1, mSDF-1-$Y_z$, or $X_p$-mSDF-1-$Y_z$ peptide; n is an integer from 0-3; q is an integer from 1-3; L is a linker sequence of 3-9 amino acids; and R is a self-assembling peptide having the amino acid sequence of any one of the sequences selected from SEQ ID NOs:1-51, described herein. An exemplary fusion protein of the present invention includes mSDF-1 peptide or $X_p$-mSDF-1 peptide and has the amino acid sequence of any one of SEQ ID NOs:53-56, 60-62, and 68. In certain embodiments, the linker of the fusion protein is GGGGGG (SEQ ID NO:57); GIVGPL (SEQ ID NO:58), or PVGLIG (SEQ ID NO:59) and n=1. In some embodiments, the self-assembling peptide of the fusion protein is RARADADARARADADA (SEQ ID NO:35) and q=1. In other embodiments, the self-assembling peptide of the fusion protein is RADARADARADARADA (SEQ ID NO:9) and q=1.

In a fifth aspect, the invention features a fusion protein that includes an Fc peptide attached to an isolated SDF-1, $X_p$-SDF-1, mSDF-1, $X_p$-mSDF-1, mSDF-1-$Y_z$, or $X_p$-mSDF-1-$Y_z$ peptide of the invention, wherein the fusion protein has the formula: A-(L)$_n$-Fc. Here, A is an isolated mSDF-1, $X_p$-mSDF-1, mSDF-1-$Y_z$, or $X_p$-mSDF-1-$Y_z$ peptide; n is an integer from 0-3; L is a linker sequence of 3-9 amino acids; and Fc is an Fc peptide from an Fc region of an immunoglobulin (e.g., human IgG1). In certain embodiments, A is either mSDF-1 peptide or $X_p$-mSDF-1 peptide and includes the amino acid sequence of any one of SEQ ID NOs:53-56, 60-62, 65-67, and 68. In some embodiments, L is GGGGS (SEQ ID NO:84).

In a sixth aspect, the invention features a nucleic acid that includes a nucleotide sequence encoding an isolated mutant SDF-1 peptide or fusion peptide of any of the above aspects. Exemplary nucleotide sequences include, for example, the nucleic acid of SEQ ID NO:72 or the nucleic acid of SEQ ID NO:74.

In a seventh aspect, the invention features a biologically compatible peptide membrane that includes one or more self-assembling peptide(s) having an amino acid sequence selected from any one of SEQ ID NOs: 1-51, wherein between 0.1-10% of the one or more self-assembling peptide(s) are bound to isolated mSDF-1, $X_p$-mSDF-1, mSDF-1-$Y_z$, or $X_p$-mSDF-1-$Y_z$ peptide. In certain embodiments of the seventh aspect, isolated mSDF-1, $X_p$-mSDF-1, mSDF-1-$Y_z$, or $X_p$-mSDF-1-$Y_z$ peptide is bound to a self-assembling peptide by a biotin/avidin linkage, or the mutant SDF-1 peptides may be covalently bound to a self-assembling peptide by a peptide bond. In any embodiment of the seventh aspect, a spacer can separate the isolated mSDF-1, $X_p$-mSDF-1, mSDF-1-$Y_z$, or $X_p$-mSDF-1-$Y_z$ peptide from one or more self-assembling peptide(s) by at least 14 angstroms and no more than 250 angstroms.

In an eighth aspect, the invention features a method of treating or ameliorating tissue damage resulting from a disease or condition in a subject in need of treatment or amelioration. The method includes administering to damaged tissue of a subject an isolated mSDF-1, $X_p$-mSDF-1, mSDF-1-$Y_z$, $X_p$-mSDF-1-$Y_z$, or A-(L)$_n$-Fc peptide, as described herein, in an amount sufficient to treat or ameliorate tissue damage. In some embodiments, the peptide is attached to a biologically compatible membrane or is attached to a self-assembling peptide that forms a biologically compatible membrane after administration to damaged tissue of the subject.

The disease or condition may be stroke, limb ischemia, tissue damage due to trauma, myocardial infarction, peripheral vascular disease, peripheral artery disease, or diabetic ulcers. In some embodiments, a subject is being treated for damage to cardiac tissue.

Administration of the peptide may be through injection or implantation into, for example, cardiac tissue (e.g., myocardium) of a subject. In some embodiments, administration may be through intra-arterial or intra-coronary injection.

By "an amount sufficient" is meant the amount of a therapeutic agent (e.g., a protease-resistant SDF-1 peptide), alone or in combination with another therapeutic regimen, required to treat or ameliorate a disorder or condition in a clinically relevant manner. A sufficient amount of a therapeutic agent used to practice the present invention for therapeutic treatment of, e.g., tissue damage varies depending upon the manner of administration, age, and general health of the subject. Ultimately, the medical practitioner prescribing such treatment will decide the appropriate amount and dosage regimen.

By "fragment" is meant a portion of a nucleic acid or polypeptide that contains at least, e.g., 10%, 20%, 30%, 40%, 50%, 60%, 70%, 80%, 90%, 95%, or more of the entire length of the nucleic acid or polypeptide. A nucleic acid fragment may contain, e.g., 10, 20, 30, 40, 50, 60, 70, 80, 90, 100, or 200 or more nucleotides, up to the full length of the nucleic acid. A polypeptide fragment may contain, e.g., 10, 20, 30, 40, 50, or 60 or more amino acids, up to the full length of the polypeptide. Fragments can be modified as described herein and as known in the art.

By "operably linked" is meant genetic elements that are joined in a manner that enables them to carry out their normal functions. For example, a sequence encoding a peptide is operably linked to a promoter when its transcription is under the control of the promoter and the transcript produced is correctly translated into the peptide.

By "pharmaceutically acceptable carrier" is meant a carrier that is physiologically acceptable to the treated subject while retaining the therapeutic properties of the composition with which it is administered. One exemplary pharmaceutically acceptable carrier substance is physiological saline. Other physiologically acceptable carriers and their formulations are known to one skilled in the art and are described, for example, in Remington's Pharmaceutical Sciences (20$^{th}$ edition, ed. A. Gennaro, 2000, Lippincott, Williams & Wilkins, Philadelphia, Pa.).

By "promoting wound healing" or "promoting tissue repair" is meant augmenting, improving, increasing, or inducing closure, healing, or repair of a wound or damaged tissue. The wound or tissue damage may be the result of any disorder or condition (e.g., disease, injury, or surgery) and may be found in any location in the subject (e.g., an internal or wound). For example, the wound or tissue damage may be the result of a cardiovascular condition such as, e.g., myocardial infarction. Alternatively, the wound or tissue damage may be the result of peripheral vascular disease.

By "protein," "polypeptide," "polypeptide fragment," or "peptide" is meant any chain of two or more amino acid residues, regardless of posttranslational modification (e.g., glycosylation or phosphorylation), constituting all or part of a naturally occurring polypeptide or peptide or constituting a non-naturally occurring polypeptide or peptide. A polypeptide or peptide may be said to be "isolated" or "substantially pure" when physical, mechanical, or chemical methods have been employed to remove the polypeptide from cellular constituents. An "isolated peptide," "substantially pure polypeptide," or "substantially pure and isolated polypeptide" is typically considered removed from cellular constituents and substantially pure when it is at least 60% by weight free from the proteins and naturally occurring organic molecules with which it is naturally associated. The polypeptide may be at least 75%, 80%, 85%, 90%, 95%, or 99% by weight pure. A substantially pure polypeptide may be obtained by standard techniques, for example, by extraction from a natural source (e.g., cell lines or biological fluids), by expression of a recombinant nucleic acid encoding the polypeptide, or by chemically synthesizing the polypeptide. Purity can be measured by any appropriate method, e.g., by column chromatography, polyacrylamide gel electrophoresis, or HPLC analysis. Alternatively, a polypeptide is considered isolated if it has been altered by human intervention, placed in a location that is not its natural site, or if it is introduced into one or more cells.

The peptides and polypeptides of the invention, as defined above, include all "mimetic" and "peptidomimetic" forms. The terms "mimetic" and "peptidomimetic" refer to a synthetic chemical compound that has substantially the same structural and/or functional characteristics of the peptides or polypeptides of the invention. The mimetic can be either entirely composed of synthetic, non-natural analogs of amino acids or may be a chimeric molecule of natural amino acids and non-natural analogs of amino acids. The mimetic can also incorporate any amount of conservative substitutions, as long as such substitutions do not substantially alter the mimetic's structure or activity.

By "preventing" or "reducing the likelihood of" is meant reducing the severity, the frequency, and/or the duration of a disease or disorder (e.g., myocardial infarction or peripheral vascular disease) or the symptoms thereof. For example, reducing the likelihood of or preventing tissue damage is synonymous with prophylaxis or the chronic treatment of tissue damage.

By "protease protective organic group" is meant an organic group, other than a proteinogenic amino acid, that, when added to the N-terminal amino acid of SDF-1 or a mutated form of SDF-1 (mSDF-1), results in a modified peptide that maintains at least, for example, 10, 15, 20, 25, 30, 40, 50, 60, 70, 80, 90, 95, 99, or 100% of the chemoattractant activity of unmodified SDF-1 (as determined by, e.g., assays of Jurkat T cell migration, described herein) and that is inactivated by an enzyme (e.g., DPPIV) at a rate of less than, for example, 50, 45, 40, 35, 30, 25, 20, 15, 10, 5, or 1% of the rate of inactivation of unmodified SDF-1.

By "protease resistant" is meant a peptide or polypeptide that contains one or more modifications in its primary sequence of amino acids compared to a native or wild-type peptide or polypeptide (e.g., native or wild-type SDF-1) and exhibits increased resistance to proteolysis compared to the native or wild-type peptide or polypeptide without the one or more amino acid modifications. By "increased protease resistance" is meant an increase as assessed by in vitro or in vivo assays, including those exemplified herein, as compared to the peptide or polypeptide absent the amino acid sequence changes. Increased resistance to proteases can be assessed by testing for activity or expression following exposure to particular proteases (e.g., MMP-2, MMP-9, DPPIV, leukocyte elastase, cathepsin G, carboxypeptidase M, or carboxypeptidase N) using assays such as, for example, Jurkat T-lymphocyte migration assays, CXCR-4-cAMP receptor activation assays, and CXCR4- or CXCR7-β-arrestin assays. Typically, the increase in protease resistance is at least about 1%, 2%, 3%, 4%, 5%, 6%, 7%, 8%, 9%, 10%, 20%, 30%, 40%, 50%, 60%, 70%, 80%, 90%, 91%, 92%, 93%, 94%, 95%, 96%, 97%, 98%, 99%, 100%, 200%, 300%, 400%, 500%, or more compared to the same peptide or polypeptide, absent the changes in amino acid sequence that confer the resistance.

By "proteinogenic" is meant that the amino acids of a polypeptide or peptide are the L-isomers of: alanine (A); arginine (R); asparagine (N); aspartic acid (D); cysteine (C); glutamic acid (E); glutamine (Q); glycine (G); histidine (H); isoleucine (I); leucine (L); lysine (K); methionine (M); phenylalanine (F); proline (P); serine (S); threonine (T); tryptophan (W); tyrosine (Y); or valine (V).

By "SDF" or "SDF-1" is meant a stromal cell derived factor peptide which can include the sequence of SEQ ID NO:52 or any of the multiple forms of SDF (e.g., SDF-1α (CXCL12a), SDF-1β (CXCL12b), and SDF-γ, produced by alternate splicing of the same gene). SDF-1β includes an additional four amino acid residues at the C-terminus of SDF-1α, Arg-Phe-Lys-Met (SEQ ID NO: 85). The first three exons of SDF-1γ are identical to those of SDF-1α and SDF-1β. The fourth exon of SDF-1γ is located 3200 basepairs downstream from the third exon on the SDF-1 locus and lies between the third exon and the fourth exon of SDF-1β. Although SEQ ID NO:52 shows the sequence of SDF-1α, this sequence may be extended at the C-terminus to include additional amino acid residues. The invention includes mutations of SDF-1α, SDF-1β (SEQ ID NO: 63), and SDF-γ (SEQ ID NO: 64). For the purposes of the present invention, the term "SDF" or "SDF-1" refers to the active form of the peptide, i.e., after cleavage of the signal peptide.

By "mSDF-1," "mSDF," or "SDF(NqN')" (where N is the one letter designation of the amino acid originally present, q is its position from the N-terminus of the peptide, and N' is the amino acid that has replaced N) is meant a mutant SDF-1 peptide. Peptides that have been mutated by the addition of amino acids (e.g., one or more amino acids) at the N-terminus are abbreviated "$X_p$-R," where X is a proteinogenic amino acid or protease protective organic group, p is an integer, and R is the peptide prior to extension (e.g., SDF-1 or mSDF-1). For example, "SSDF-1" or "S-mSDF-1" is an SDF-1 or mSDF-1 molecule, respectively, with a serine residue added at the N-terminus. Peptides that have been mutated by the addition of amino acids (e.g., one or more amino acids) at the C-terminus are abbreviated "R-$Y_z$," where Y is a proteinogenic amino acid or protease protective organic group, z is an integer, and R is the peptide prior to extension (e.g., SDF-1, mSDF-1, or $X_p$-mSDF-1). Unless otherwise indicated, all pharmaceutically acceptable forms of peptides may be used, including all pharmaceutically acceptable salts.

By "subject" is meant a mammal, including, but not limited to, a human and non-human mammal, such as a bovine, equine, canine, ovine, or feline.

By "sustained release" or "controlled release" is meant that the therapeutically active component is released from the formulation at a controlled rate such that therapeutically beneficial levels (but below toxic levels) of the component are maintained over an extended period of time ranging from, e.g., about 12 hours to about 4 weeks (e.g., 12 hours, 24 hours, 48 hours, 1 week, 2 weeks, 3 weeks, or 4 weeks), thus providing, for example, a 12-hour to a 4-week dosage form.

By "treating" or "ameliorating" is meant administering a pharmaceutical composition for therapeutic purposes or administering treatment to a subject already suffering from a disorder to improve the subject's condition. By "treating a disorder" or "ameliorating a disorder" is meant that the disorder and the symptoms associated with the disorder are, e.g., alleviated, reduced, cured, or placed in a state of remission. As compared with an equivalent untreated control, such amelioration or degree of treatment is at least 5%, 10%, 20%, 30%, 40%, 50%, 60%, 70%, 80%, 90%, 95%, 99%, or 100%, as measured by any standard technique.

Other features and advantages of the invention will be apparent from the detailed description and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-1D show the cDNA sequences and amino acid sequences of SDF-1α, SDF-1β, and SDF-1γ. FIG. 1A-I is a listing of the amino acid sequences of SDF-1α (SEQ ID NO:52), SDF-1β (SEQ ID NO:63), and SDF-1γ (SEQ ID NO:64) after removal of the signal peptide (amino acids 1-21). FIG. 1A-2 is a listing of the amino acid sequences of SDF-1a (SEQ ID NO:86), SDF-1β (SEQ ID NO:87), and SDF-1γ (SEQ ID NO:88), including the signal peptide. FIG. 1B is the cDNA sequence of SDF-1a (SEQ ID NO:69; NCBI Reference Sequence: NM_199168). FIG. 1C (−1 and −2) is the cDNA sequence of SDF-1β (SEQ ID NO:70; NCBI Reference Sequence: NM_000609). FIG. 1D is the cDNA sequence of SDF-1γ (SEQ ID NO:71; NCBI Reference Sequence: NM_001033886). For the cDNA sequences, the sequence coding for the final protein without signal peptide is underlined.

FIGS. 2A-2D are graphs showing that SSDF-1(S4V) has similar receptor specificity to SDF-1. FIG. 2A is a graph showing migration of Jurkat cells induced by SDF-1 variants (n>8). FIG. 2B is a graph showing that SDF-1 variants decrease cAMP levels by activation of CXCR4 and Gαi (RLU=relative luminescence units) (n=4). FIG. 2C is a graph showing that SDF-1 variants induce binding of β-arrestin to CXCR4 (n=3). FIG. 2D is a graph showing that SDF-1 variants induce binding of β-arrestin to CXCR7 (n=3).

FIGS. 3A-3D are graphs and electrophoretic gels showing that SSDF-1 (S4V) is resistant to MMP-2 cleavage. FIG. 3A is a graph of the fluorescence measurements taken at different time points after the addition of MMP-2 (n=4). FRET-based peptides were synthesized with the first 8 amino acids of SDF-1 (SEQ ID NO: 89) or SDF-1(S4V) (SEQ ID NO: 91). FIG. 3B is a bar graph showing the initial cleavage rate of the N-terminal 8 amino acid peptides of SDF-1 (SEQ ID NO: 89) and SDF-1(S4V) (SEQ ID NO: 91), calculated 60 minutes after the addition of MMP-2. FIGS. 3C and 3D are electrophoretic gels showing that a larger fraction of Sumo-SDF-1-RAD (FIG. 3C) is cleaved in 1 hour than Sumo-SDF-1 (S4V)-RAD (FIG. 3D) in 48 hours. Sumo-SDF-1-RAD and Sumo-SDF-1 (S4V)-RAD were incubated with MMP-2, and the reaction was stopped at different time points.

FIG. 5 is a bar graph showing the results of a Matrigel™ plug assay. The assay quantifies new vessel formation with different SDF-1 variants in vivo at different dosages.

FIG. 6A is a graph showing the release of fluorescently labeled RAD from a nanofiber gel. 100 nM of FITC-labeled self-assembling peptides (FITC-RAD) were dissolved in PBS or mixed with a hydrogel of 1% nanofibers. Nanofibers were incubated in fresh PBS for time periods of 15 minutes, and cumulative release of fluorescence was measured. The curve of FITC-RAD+PBS indicates free diffusion in the employed system. FIG. 6B is a graph showing the release of fluorescently labeled SSDF-1 or SSDF-1-RAD from a nanofiber gel. 100 nM of Alexa-labeled SSDF-1, Alexa-labeled SSDF-1-RAD fusion protein, or Alexa 488 alone (as a small-molecule control) were mixed with a 1% nanofiber hydrogel. Cumulative release of fluorescence was measured by assessing the fluorescence remaining in the gel over the course of 24 hours. 78% of the SSDF-1-RAD fusion protein was still in the nanofiber gel after 24 hours. FIG. 6C is a micrograph showing tissue samples taken from mouse ischemic hindlimbs injected with nanofiber hydrogels containing biotinylated self-assembling peptides (1% of total peptides). Tissues were harvested at different time points and nanofibers were detected with Alexa-fluor-labeled streptavidin (green). Red=dystrophin; blue=DAPI. FIG. 6D is a graph plotting the total surface of the hydrogels as a function of time (n=5 per group).

FIGS. 7A-7C are images and graphs showing that protease-resistant SSDF-1(S4V) increases blood flow in a mouse hindlimb ischemia model. FIG. 7A is a set of representative images of the study in FIG. 7B. Blood flow in ischemic limb was normalized to blood flow in normal limb. FIG. 7B is a graph showing that nanofibers+SSDF-1(S4V)-RAD increased blood flow significantly over control animals at 4 and 6 weeks (n=10). FIG. 7C is a graph showing blood flow after different dosages of SSDF-1(S4V)-RAD were injected in the ischemic hindlimb (n=10). All groups included nanofibers. In FIGS. 7B and 7C, *=p<0.001 vs. control, †=p<0.01 vs. nanofibers; ‡=p<0.05 vs. nanofibers+SSDF-1-RAD; §=p<0.05 vs. control; #=p<0.001 vs. 0 nM; and **=p<0.01 vs. 0 nM.

FIG. 8A is a set of representative images of ischemic hindlimbs. Green=smooth muscle actin; red=isolectin. FIG. 8B is a bar graph showing the arteriolar vessel density in hindlimb of mice treated with different dosages of SSDF-1(S4V)-RAD. Per mouse, a total surface of 28 mm$^2$ was measured. Scale bar=100 μm (n>6 for each group).

FIGS. 9A-9C are tables showing the initial cleavage rates of a FRET-based peptide library. In brief, peptides containing the first 8 amino acids of SDF-1 (KPVSLSYR) and all possible single amino acid mutations at position 3, 4, 5, or 6 (spanning the MMP-2 cleavage site) were synthesized, as described in Example 1. All peptides were synthesized with a fluorescent 7-methoxycoumarin-3-carboxylic acid (MCA) residue at the N-terminus and a quencher lysine-dinitrophenol (Dpn) residue at the C-terminus. Peptides (10 μM) were incubated with activated MMP-2 (FIG. 9A), leukocyte elastase (FIG. 9B), or cathepsin G (FIG. 9C). Peptide cleavage rates were determined by FRET and were normalized to the cleavage rate of peptides containing the first 8 amino acids of SDF-1 (100%). Column headers show the site of the mutation(s) and the row title shows the mutated amino acid in that position. Mutations with an initial cleavage rate of less than 10% are indicated in italics and mutations with an initial cleavage rate between 10% and 20% of SDF-1 analogue are indicated in grey shading.

DETAILED DESCRIPTION

Figure 4:
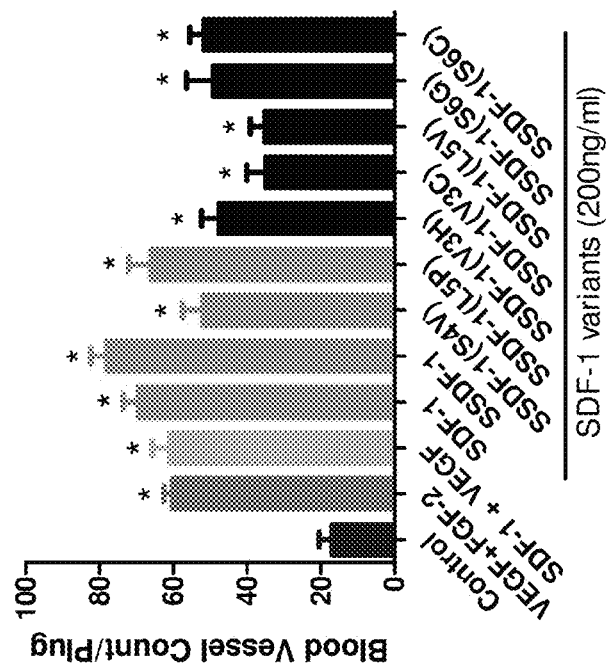
FIG. 4 is a bar graph showing the results of a Matrigel™ plug assay. The assay quantifies new vessel formation with different SDF-1 variants in vivo. The control group includes Matrigel™ only in the assay. The positive control includes VEGF and FGF-2 in the assay. Black bars represent newly made mutants of SDF-1. (*=P<0.05 compared to the control.)

The present invention is based upon the concept that the recovery of damaged tissue, e.g., damaged cardiac tissue, is promoted by exposing the tissue to SDF-1 that has been mutated to increase resistance to enzymatic cleavage (e.g., cleavage by MMP-2, MMP-9, DPPIV, leukocyte elastase, cathepsin G, carboxypeptidase M, or carboxypeptidase N). Such peptides may be delivered as isolated peptides, with or without a pharmaceutically acceptable carrier, or by means of a membrane formed by spontaneously assembling peptides (see, e.g., U.S. Pat. Nos. 5,670,483 and 6,548,630). Methods of attaching factors to membranes and the use of the membranes in delivering therapeutic agents to, for example, cardiac tissue have also been described (see, e.g., U.S. Patent Application Publication Nos. 2006/0148703 and 2006/0088510). The same procedures for making and using membranes may be applied to the present invention.

SDF-1 and Protease-Resistant Mutants

SDF-1 is a small cytokine belonging to the chemokine family that is officially designated chemokine (C-X-C motif) ligand 12 (CXCL12). SDF-1 is produced in multiple forms, SDF-1α (CXCL12a), SDF-1β (CXCL12b), and SDF-1γ, by alternate splicing of the same gene.

Unmutated SDF-1α has the following sequence:

```
                                        (SEQ ID NO: 52)
K P V S L S Y R C P C R F F E S H V A R A N V K H

L K I L N T P N C A L Q I V A R L K N N N R Q V C

I D P K L K W I Q E Y L E K A L N K
```

The SDF-1 peptides of the present invention include SDF-1 peptides with mutations to render the peptides resistant to, for example, matrix metalloproteinase-2 (MMP-2), matrix metalloproteinase-9 (MMP-9), dipeptidyl peptidase IV (DPPIV), leukocyte elastase, cathepsin G, carboxypeptidase M, or carboxypeptidase N.

The peptides of the invention include mutant forms of SDF-1 (mSDF-1), which are characterized by a change in the third, fourth, fifth, and/or sixth amino acid residue from the N-terminus of unmutated SDF-1, and have at least amino acids 1-8 of the following sequence:

```
                                        (SEQ ID NO: 53)
K P X3 X4 X5 X6 Y R C P C R F F E S H V A R A N V K

H L K I L N T P N C A L Q I V A R L K N N N R Q V

C I D P K L K W I Q E Y L E K A L N K,
``` wherein
   $X_3$ is any amino acid residue;
   $X_4$ is serine or valine;
   $X_5$ is leucine, proline, threonine, or valine; and
   $X_6$ is any amino acid residue.

Excluded from the present invention are SDF-1 peptides that include the amino acid sequence of at least amino acids 1-8 of unmutated SDF-1 (SEQ ID NO:52) or SEQ ID NOs:65-67, defined as follows.

```
                                        (SEQ ID NO: 65)
K P V V L S Y R C P C R F F E S H V A R A N V K H

L K I L N T P N C A L Q I V A R L K N N N R Q V C

I D P K L K W I Q E Y L E K A L N K (SEQ ID NO: 66)
K P V S P S Y R C P C R F F E S H V A R A N V K H

L K I L N T P N C A L Q I V A R L K N N N R Q V C

I D P K L K W I Q E Y L E K A L N K (SEQ ID NO: 67)
K P V V P S Y R C P C R F F E S H V A R A N V K H

L K I L N T P N C A L Q I V A R L K N N N R Q V C

I D P K L K W I Q E Y L E K A L N K
```

In certain embodiments, the amino acid residue at position $X_3$ of SEQ ID NO:53 is not isoleucine, e.g., when all other residues are wild-type amino acid residues. In other embodiments, the amino acid residue at position $X_5$ of SEQ ID NO:53 is not a tryptophan or a glutamic acid amino acid residue, e.g., when all other residues are wild-type amino acid residues.

The peptides of the invention may include mSDF-1 peptides with a mutation at the third and/or sixth amino acid residue from the N-terminus of unmutated SDF-1 and have the sequence:

(SEQ ID NO: 68)
K P $X_3$ S L $X_6$ Y R C P C R F F E S H V A R A N V K H

L K I L N T P N C A L Q I V A R L K N N N R Q V C

I D P K L K W I Q E Y L E K A L N K, wherein $X_3$ and $X_6$ are any amino acid.

In certain embodiments, $X_3$ of SEQ ID NO:68 is any amino acid residue and $X_6$ of SEQ ID NO:68 is serine. In other embodiments, $X_3$ of SEQ ID NO:68 is valine and $X_6$ of SEQ ID NO:68 is any amino acid residue.

In certain embodiments, the amino acid residue at position $X_3$ of SEQ ID NO:68 is not isoleucine.

For example, the mSDF-1 peptide may include a Val→His (SEQ ID NO:54) or Val→Cys (SEQ ID NO:55) mutation at the third amino acid position.

(SEQ ID NO: 54)
K P H S L S Y R C P C R F F E S H V A R A N V K H

L K I L N T P N C A L Q I V A R L K N N N R Q V C

I D P K L K W I Q E Y L E K A L N K (SEQ ID NO: 55)
K P C S L S Y R C P C R F F E S H V A R A N V K H

L K I L N T P N C A L Q I V A R L K N N N R Q V C

I D P K L K W I Q E Y L E K A L N K

In other embodiments, the mSDF-1 peptide may include a Leu→Thr (SEQ ID NO:56) or Leu→Val (SEQ ID NO:60) mutation at the fifth amino acid position. In certain embodiments, the fifth amino acid is not proline.

(SEQ ID NO: 56)
K P V S T S Y R C P C R F F E S H V A R A N V K H

L K I L N T P N C A L Q I V A R L K N N N R Q V C

I D P K L K W I Q E Y L E K A L N K (SEQ ID NO: 60)
K P V S V S Y R C P C R F F E S H V A R A N V K H

L K I L N T P N C A L Q I V A R L K N N N R Q V C

I D P K L K W I Q E Y L E K A L N K

In other embodiments, the mSDF-1 peptide may include a Ser→Cys (SEQ ID NO:61) or Ser→Gly (SEQ ID NO:62) mutation at the sixth amino acid position.

(SEQ ID NO: 61)
K P V S L C Y R C P C R F F E S H V A R A N V K H

L K I L N T P N C A L Q I V A R L K N N N R Q V C

I D P K L K W I Q E Y L E K A L N K (SEQ ID NO: 62)
K P V S L G Y R C P C R F F E S H V A R A N V K H

L K I L N T P N C A L Q I V A R L K N N N R Q V C

I D P K L K W I Q E Y L E K A L N K

The peptides of the invention also encompass any combination of the mutations described herein. For example, the mSDF-1 peptides may include a Val→Cys mutation at the third amino acid position of SEQ ID NO:53 and a Ser→Cys mutation at the sixth amino acid position of SEQ ID NO:53.

Mutations made to the SDF-1 peptides to confer protease resistance may also include, for example, the addition of a moiety (e.g., a proteinogenic amino acid or protease protective organic group) to the N-terminus of, e.g., the mSDF-1 peptides (described above), yielding $X_p$-mSDF-1. For example, X may be: $R^1$—$(CH_2)_d$—, where d is an integer from 0-3, and $R^1$ is selected from: hydrogen (with the caveat that when $R^1$ is hydrogen, d must be at least 1); a branched or straight $C_1$-$C_3$ alkyl; a straight or branched $C_2$-$C_3$ alkenyl; a halogen, $CF_3$; —$CONR^5R^4$; —$COOR^5$; —$COR^5$; —$(CH_2)_qNR^5R^4$; —$(CH_2)_qSOR^5$; —$(CH_2)_qSO_2R^5$, —$(CH_2)_qSO_2NR^5R_4$; and $OR^5$, where $R^4$ and $R^5$ are each independently hydrogen or a straight or branched $C_1$-$C_3$ alkyl. In instances where an organic group is used for X, p should be 1. X may also represent a proteinogenic amino acid, wherein, for example, 1-10 (e.g., 1-9, 1-8, 1-7, 1-6, 1-5, 1-4, 1-3, 1-2, or 1) amino acid(s) is/are added to the N-terminus of SDF-1 (e.g., mSDF-1), and one or more of these added amino acids may be substituted with a protease protective organic group. For example, a proteinogenic amino acid (e.g., serine) or protease protective organic group may be added to the N-terminus of SDF-1 (e.g., mSDF-1) to confer, for example, resistance to DPPIV cleavage without substantially changing the chemoattractant activity or resistance to other proteases (e.g., MMP-2).

Mutations made to the SDF-1 peptides to confer protease resistance may also include, for example, the addition of a moiety (e.g., a proteinogenic amino acid) to the C-terminus of, e.g., the mSDF-1 peptides (described above), yielding mSDF-1-$Y_z$ or $X_p$-mSDF-1-$Y_z$. Y may represent a proteinogenic amino acid, wherein, for example, 1-10 (e.g., 1-9, 1-8, 1-7, 1-6, 1-5, 1-4, 1-3, 1-2, or 1) amino acid(s) is/are added to the C-terminus of SDF-1 (e.g., mSDF-1 or $X_p$-mSDF-1). For example, a proteinogenic amino acid (e.g., serine) may be added to the C-terminus of SDF-1, mSDF-1, or $X_p$-mSDF-1 to confer, for example, resistance to carboxypeptidase M or carboxypeptidase N cleavage without substantially changing the chemoattractant activity or resistance to other proteases (e.g., MMP-2). In one embodiment, the invention features an isolated mSDF-1-$Y_z$ or $X_p$-mSDF-1-$Y_z$ peptide, wherein SDF-1 includes the amino acid sequence of SEQ ID NO:65, SEQ ID NO:66, or SEQ ID NO:67. However, C-terminal modifications may be made to any of the SDF-1 peptides described herein.

The mutated SDF-1 peptides of the invention retain their ability to act as chemoattractants, but are resistant to enzymatic (e.g., proteolytic) digestion. The mSDF-1 peptides maintain chemoattractant activity with a sensitivity (as determined by, e.g., the effective concentration needed to obtain 50% of maximal response in the assays of Jurkat T cell migration, as described herein) of at least, for example, 10, 15, 20, 25, 30, 40, 50, 60, 70, 80, 90, 95, 99, or 100% of the sensitivity of unmutated SDF-1. Loss of chemoattractant activity may be due to cleavage by, for example, MMP-2, MMP-9, leukocyte elastase, DPPIV, cathepsin G, carboxypeptidase M, or carboxypeptidase N. The rate of inactivation of mSDF-1 may be less than, for example, 50, 45, 40, 35, 30, 25, 20, 15, 10, 5, or 1% of the rate of inactivation of SDF-1.

The mutated SDF-1 peptides may be resistant to cleavage by, for example, MMP-2, MMP-9, DPPIV, leukocyte elastase, cathepsin G, carboxypeptidase M, or carboxypeptidase N. Thus, they are ideally suited for use at sites such as, e.g., damaged tissue (e.g., damaged cardiac tissue), where proteolytic enzymes are present at high concentrations, or delivery to the site via the blood or plasma. Accordingly, mutated SDF-1 peptides are suitable for intravenous, intra-arterial, and/or intracoronary administration due to the improved stability of such peptides. In addition, an MMP-2 cleavage site can, if desired, be placed in linker regions joining the SDF-1 peptides to self-assembling peptides, described herein. This will allow for the protease-resistant SDF-1 peptides to be released from an implanted or injected membrane, also described herein, over time.

Protease-resistant SDF-1 peptides of the present invention may include amino acids or sequences modified either by natural processes, such as posttranslational processing, or by chemical modification using techniques known in the art. Modifications may occur anywhere in a polypeptide, including the polypeptide backbone, the amino acid side-chains, and the amino- or carboxy-terminus. The same type of modification may be present in the same or varying degrees at several sites in a given polypeptide, and a polypeptide may contain more than one type of modification. Modifications include, e.g., PEGylation, acetylation, acylation, addition of acetomidomethyl (Acm) group, ADP-ribosylation, alkylation, amidation, biotinylation, carbamoylation, carboxyethylation, esterification, covalent attachment to fiavin, covalent attachment to a heme moiety, covalent attachment of a nucleotide or nucleotide derivative, covalent attachment of drug, covalent attachment of a marker (e.g., a fluorescent or radioactive marker), covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins (e.g., arginylation), and ubiquitination. Posttranslational modifications also include the addition of polymers to stabilize the peptide or to improve pharmacokinetics or pharmacodynamics.

Fusion Proteins and Self-Assembling Peptides

The invention also encompasses fusion proteins in which any of the mSDF-1 or $X_p$-mSDF-1 sequences described herein are linked to either self-assembling peptides capable of forming a biologically compatible membrane or the Fc region of IgG. Fusion proteins are formed either by joining the C-terminal end of a protease-resistant SDF-1 peptide directly to either the N-terminal end of a self-assembling peptide or the Fc region of IgG, or the two peptides can be joined by a linker sequence. Thus, the invention includes fusion proteins of the formula: $A\text{-}(L)_n\text{-}(R)_q$, wherein n is an integer from 0-3, q is an integer from 1-3, A is one of the protease-resistant SDF-1 peptides (i.e., mSDF-1, $X_p$-mSDF-1, mSDF-1-$Y_z$, or $X_p$-mSDF-1-$Y_z$), L is a linker sequence 3-9 amino acids long, and R is a self-assembling peptide.

Linker sequences may include, for example, GGGGGG (abbreviated as "6G," SEQ ID NO:57), GIVGPL (SEQ ID NO:58), and PVGLIG (SEQ ID NO:59). The lattermost represents an MMP-2 cleavage site (MCS). GIVGPL (SEQ ID NO:58) represents a scrambled version of MCS and is abbreviated as SCR. The SCR sequence also undergoes MMP-2 cleavage, although at a slower rate than MCS.

The self-assembling peptide may be, for example, one of the following peptides:

AKAKAEAEAKAKAEAE; (SEQ ID NO: 1)
AKAEAKAEAKAEAKAE; (SEQ ID NO: 2)
EAKAEAKAEAKAEAKA; (SEQ ID NO: 3)
KAEAKAEAKAEAKAEA; (SEQ ID NO: 4)
AEAKAEAKAEAKAEAK; (SEQ ID NO: 5)
ADADARARADADARAR; (SEQ ID NO: 6)
ARADARADARADARAD; (SEQ ID NO: 7)
DARADARADARADARA; (SEQ ID NO: 8)
RADARADARADARADA; (SEQ ID NO: 9)
ADARADARADARADAR; (SEQ ID NO: 10)
ARADAKAEARADAKAE; (SEQ ID NO: 11)
AKAEARADAKAEARAD; (SEQ ID NO: 12)
ARAKADAEARAKADAE; (SEQ ID NO: 13)
AKARAEADAKARADAE; (SEQ ID NO: 14)
AQAQAQAQAQAQAQAQ; (SEQ ID NO: 15)
VQVQVQVQVQVQVQVQ; (SEQ ID NO: 16)
YQYQYQYQYQYQYQYQ; (SEQ ID NO: 17)
HQHQHQHQHQHQHQHQ; (SEQ ID NO: 18)
ANANANANANANANAN; (SEQ ID NO: 19)
VNVNVNVNVNVNVNVN; (SEQ ID NO: 20)
YNYNYNYNYNYNYNYN; (SEQ ID NO: 21)
HNHNHNHNHNHNHNHN; (SEQ ID NO: 22)
ANAQANAQANAQANAQ; (SEQ ID NO: 23)
AQANAQANAQANAQAN; (SEQ ID NO: 24)
VNVQVNVQVNVQVNVQ; (SEQ ID NO: 25)
VQVNVQVNVQVNVQVN; (SEQ ID NO: 26)
YNYQYNYQYNYQYNYQ; (SEQ ID NO: 27)
YQYNYQYNYQYNYQYN; (SEQ ID NO: 28)

-continued

HNHQHNHQHNHQHNHQ; (SEQ ID NO: 29)

HQHNHQHNHQHNHQHN; (SEQ ID NO: 30)

AKAQADAKAQADAKAQAD; (SEQ ID NO: 31)

VKVQVDVKVQVDVKVQVD; (SEQ ID NO: 32)

YKYQYDYKYQYDYKYQYD; (SEQ ID NO: 33)

HKHQHDHKHQHDHKHQHD; (SEQ ID NO: 34)

RARADADARARADADA; (SEQ ID NO: 35)

RADARGDARADARGDA; (SEQ ID NO: 36)

RAEARAEARAEARAEA; (SEQ ID NO: 37)

KADAKADAKADAKADA; (SEQ ID NO: 38)

AEAEAHAHAEAEAHAH; (SEQ ID NO: 39)

FEFEFKFKFEFEFKFK; (SEQ ID NO: 40)

LELELKLKLELELKLK; (SEQ ID NO: 41)

AEAEAKAKAEAEAKAK; (SEQ ID NO: 42)

AEAEAEAEAKAK; (SEQ ID NO: 43)

KAKAKAKAEAEAEAEA; (SEQ ID NO: 44)

AEAEAEAEAKAKAKAK; (SEQ ID NO: 45)

RARARARADADADADA; (SEQ ID NO: 46)

ADADADADARARARAR; (SEQ ID NO: 47)

DADADADARARARARA; (SEQ ID NO: 48)

HEHEHKHKHEHEHKHK; (SEQ ID NO: 49)

VEVEVEVEVEVEVEVEVE; (SEQ ID NO: 50)
and

RFRFRFRFRFRFRFRFRFRF. (SEQ ID NO: 51)

Exemplary fusion peptides include the self-assembling peptides RADARADARADARADA (SEQ ID NO:9) and RARADADARARADADA (SEQ ID NO:35), wherein q=1, and the protease-resistant SDF-1 peptide SDF(S6C) or $X_p$-SDF(S6C), wherein p=1. When joined together, the resulting fusion proteins are, for convenience, abbreviated as SDF(S6C)-RAD or $X_p$-SDF(S6C)-RAD. Exemplary fusion proteins containing linker sequences include SDF(S6C)-6G-RAD ("6G" disclosed as SEQ ID NO: 57); $X_p$-SDF(S6C)-6G-RAD ("6G" disclosed as SEQ ID NO: 57); SDF(S6C)-MCS-RAD; $X_p$-SDF(S6C)-MCS-RAD; SDF(S6C)-SCR-RAD; and $X_p$-SDF(S6C)-SCR-RAD, wherein p=1.

The peptides used for self-assembly should be between, for example, at least 12 amino acids residues and 200 amino acid residues in length (e.g., between 12-24 amino acid residues in length) and contain alternating hydrophobic and hydrophilic amino acids. Peptides longer than about 200 amino acids may be less soluble and have decreased membrane stability.

The self-assembling peptides may be complementary. This means that the amino acids on one peptide are capable of forming ionic bonds or hydrogen bonds with the amino acids on another peptide. Ionic bonds may form between acidic and basic amino acid side chains. Ionic bonds may also form between an acidic residue on one peptide and a basic residue on another. Hydrophilic basic amino acids include Lys, Arg, His, and Orn. Hydrophilic acidic amino acids include Glu and Asp. Amino acids that form hydrogen bonds are Asn and Gln. Hydrophobic amino acids that may be incorporated into peptides include Ala, Val, Ile, Met, Phe, Tyr, Trp, Ser, Thr, and Gly.

Self-assembling peptides may also be structurally compatible. This means that they maintain an essentially constant distance between one another when they bind. Interpeptide distance can be calculated for each ionized or hydrogen bonding pair by taking the sum of the number of unbranched atoms on the side chains of each amino acid in the pair. For example, lysine has five unbranched atoms and glutamic acid has four unbranched atoms on their side chains. An interaction between these two residues on different peptides would result in an interpeptide distance of nine atoms. In a peptide containing only repeating units of EAK, all of the ion pairs would involve lysine and glutamate and, therefore, a constant interpeptide distance would be maintained. Thus, these peptides would be structurally complementary.

Peptides in which the variation in interpeptide distance varies by more than one atom (about 3-4 Å) will not form gels properly. For example, if two bound peptides have ion pairs with a nine-atom spacing and other ion pairs with a seven-atom spacing, the requirement of structural complementarity would not have been met. A full discussion of complementarity and structural compatibility may be found in, for example, U.S. Pat. Nos. 5,670,483 and 6,548,630.

The invention also encompasses fusion proteins in which any of the SDF-1, mSDF-1, $X_p$-mSDF-1, mSDF-1-$Y_z$, or $X_p$-mSDF-1-$Y_z$ peptide sequences described herein are linked to the Fc region of IgG (e.g., human IgG1). Alternatively, the Fc region may be derived from IgA, IgM, IgE, or IgD of humans or other animals, including swine, mice, rabbits, hamsters, goats, rats, and guinea pigs. The Fc region of IgG includes the CH2 and CH3 domains of the IgG heavy chain and the hinge region. The hinge serves as a flexible spacer between the two parts of the Fc fusion protein, allowing each part of the molecule to function independently. The Fc region used in the present invention can be prepared in, for example, monomeric and dimeric form.

An exemplary Fc fusion peptide is SSDF-1(S4V)-Fc with the following amino acid sequence. The GGGGS linker (SEQ ID NO: 84) is indicated in bold and the Fc peptide is underlined.

(SEQ ID NO: 83)
S K P V V L S Y R C P C R F F E S H V A R A N V K

H L K I L N T P N C A L Q I V A R L K N N N R Q V

C I D P K L K W I Q E Y L E K A L N K G G G G S <u>V</u>

-continued

D K T H T C P P C P A P E L L G G P S V F L F P P

K P K D T L Met I S R T P E V T C V V V D V S H E

D P E V K F N W Y V D G V E V H N A K T K P R E E

Q Y N S T Y R V V S V L T V L H Q D W L N G K E Y

K C K V S N K A L P A P I E K T I S K A K G Q P R

E P Q V Y T L P P S R D E L T K N Q V S L T C L V

K G F Y P S D I A V E W E S N G Q P E N N Y K T T

P P V L D S D G S F F L Y S K L T V D K S R W Q Q

G N V F S C S V Met H E A L H N H Y T Q K S L S L

SPGK

Other non-limiting examples of Fc fusion peptides include, e.g., SDF-1 (S4V)-Fc, SDF-1-Fc, and SSDF-1-Fc.

Binding of SDF-1 to Self-Assembling Peptides

Several strategies may be used for attaching protease-resistant SDF-1 to self-assembling peptides. Exemplary strategies are described as follows.

One strategy is non-covalent binding, which has previously been shown to be effective in delivering PDGF-BB, a growth factor, to tissues (Hsieh et al., *J. Clin. Invest.* 116: 237-248 (2006)).

A second attachment strategy is the biotin-sandwich method (Davis et al., *Proc. Natl. Acad. Sci. USA* 103: 8155-8160 (2006)) in which a protease-resistant SDF-1 is biotinylated and bound to biotinylated peptides using tetravalent streptavidin as a linker. To accomplish this, the protease-resistant SDF-1 may be coupled to a 15 amino acid sequence of an acceptor peptide for biotinylation (referred to as AP; Chen et al., *Nat. Methods* 2: 99-104 (2005)). Because the active site of SDF-1 is situated near the amino-terminus, fusion proteins can be made by incorporating the extra sequences at the C-terminus. The acceptor peptide sequence allows site-specific biotinylation by the *E. coli* enzyme biotin ligase (BirA; Chen et al., *Nat. Methods* 2: 99-104 (2005)). Many commercial kits are available for biotinylating proteins. However, many of these kits biotinylate lysine residues in a nonspecific manner, and this may reduce mSDF-1 activity, as it has been shown that the N-terminal lysine of SDF-1 is crucial for receptor binding and activity (Crump et al., *EMBO J.* 16: 6996-7007 (1997)). Biotinylated self-assembling peptides are made, for example, by MIT Biopolymers Laboratory and, when mixed in a 1-to-100 ratio with native self-assembling peptides, self-assembly of nanofibers should not be disturbed (Davis et al., *Proc. Natl. Acad. Sci. USA* 103: 8155-8160 (2006)).

A third targeting strategy is direct incorporation of protease-resistant SDF-1 peptides into self-assembling nanofibers by construction of a fusion protein of mutated SDF-1 with a self-assembling peptide. For example, mSDF-1 may be coupled (e.g., chemically or recombinantly) to the 16 amino acid sequence of SEQ ID NO:9 or SEQ ID NO:35. This "RAD" portion of the fusion protein will incorporate into the nanofiber scaffold while assembling.

Formation of Membranes

The invention also features biologically compatible membranes formed from self-assembling peptides, as described in U.S. Pat. Nos. 7,429,567 and 7,399,831, which have, for example, mSDF-1 or Xp-mSDF-1 peptides attached. As used herein, the term "biologically compatible" indicates that the membranes are non-toxic and can be implanted or injected into a subject without triggering an immune response. Between 0.1% and 10% (e.g., between 0.5-5%) of the peptides that assemble into the membrane are bound to a mutant SDF-1. Binding may be either, e.g., covalent or noncovalent. Noncovalent binding occurs when protease-resistant SDF-1 peptides are trapped in the membrane matrix and/or when protease-resistant SDF-1 peptides are bound to self-assembling peptides in the membrane by biotin-avidin or biotin-streptavidin linkages. The membranes may, optionally, have other therapeutic agents (e.g., PDGF, interleukin-8, IGF-1, HGF, neuregulin, periostin, VEGF, or FGF) attached.

The use of the biotin-avidin linkage is well known in the art, and standard methodology can be used for attaching protease-resistant SDF-1 peptides to self-assembling peptides either before or after membrane formation. Specific methodology for using biotin-avidin in connection with self-assembling membranes has been described in, for example, U.S. Pat. No. 7,399,831. To prevent steric interference between the biotin-avidin groups and protease-resistant peptides, a spacer may be included between the biotin-avidin group and protease-resistant peptide. The spacer can take the form of, for example, between 1-15 (e.g., 1-10) fatty acids or, for example, between 1-15 (e.g., 1-10) amino acids and separates the protease-resistant SDF-1 peptide from the self-assembling peptide by, for example, at least an additional 12 Å and by no more than an additional 250 Å. Methodologies for incorporating spacers of this type are well known in the art.

Protease-resistant SDF-1 peptides may also be joined to a self-assembling peptide that is part of the membrane by a peptide bond, i.e., the protease-resistant SDF-1 may be part of a fusion protein in which it is joined to a self-assembling peptide either directly or via an intervening linker amino acid sequence. Any of the fusion proteins described herein may be used. The membranes are made from the fusion proteins or from the self-assembling peptides by taking advantage of the inability of the fusion proteins or self-assembling peptides described herein to congregate in water. Instead, the fusion proteins or self-assembling peptides assemble into a membrane in the presence of a low concentration of, for example, monovalent metal cations (e.g., $Li^+$, $Na^+$, $K^+$, or $Cs^+$). For example, fusion proteins may be made under conditions in which self-assembly does not occur and then exposed to conditions that promote membrane formation, e.g., low monovalent metal cation concentration. The end result is a matrix which can be, for example, implanted into a subject and which will maintain a high concentration of SDF-1 biological activity at the site of implantation. Alternatively, the fusion proteins can be incorporated into an injectable pharmaceutical composition at a concentration of monovalent cation that is too low to induce self-assembly and can then be administered to a subject to induce membrane formation in vivo.

Membranes may be formed from either a homogeneous mixture of peptides or a heterogeneous mixture of peptides. The term "homogeneous," in this context, means peptides that are identical. "Heterogeneous" indicates peptides that bind to one another, but which are structurally different. Regardless of whether homogenous or heterogeneous peptides are used, the requirements with respect to the arrangement of amino acids, length, complementarity, and structural compatibility apply. In addition, the carboxyl and amino groups of the terminal residues of peptides can either be protected or not protected using standard groups and standard methods known in the art.

The self-assembling peptides and fusion proteins described herein may not form membranes in water, but may instead assemble in the presence of a low concentration of monovalent metal cation. The order of effectiveness of these cations is $Li^+>Na^+>K^+>Cs^+$ (see, e.g., U.S. Pat. No. 6,548, 630). The concentration of monovalent metal cation may be, for example, between 5 mM and 5M (e.g., 5 mM, 10 mM, 50 mM, 100 mM, 200 mM, 300 mM, 400 mM, 500 mM, 600 mM, 700 mM, 800 mM, 900 mM, 1M, 2M, 3M, 4M, or 5M). The anion associated with the monovalent cation is not critical to the invention and can be, for example, acetate, chloride, sulfate, or phosphate.

The initial concentration of self-assembling peptide will influence the final size and thickness of the membranes formed. In general, the higher the peptide concentration, the higher the extent of membrane formation. Formation can take place at peptide concentrations as low as 0.5 mM or 1 mg/ml. However, membranes are preferably formed at higher initial peptide concentrations, e.g., 10 mg/ml, to promote better handling characteristics. Peptides may be added to a salt solution (rather than adding salt to a peptide solution) to form membranes of the present invention. During membrane formation, the pH may be maintained below 12, and temperatures may be generally in the range of, for example, 4-90° C.

An exemplary membrane matrix that may be used in the compositions and methods described herein is PuraMatrix™ (BD Biosciences).

Membrane formation may be observed by simple visual inspection and this can be aided, if desired, with stains such as Congo Red. The integrity of membranes can also be observed microscopically, with or without stain.

Membranes with protease-resistant SDF-1 attached may be, for example, injected or implanted at or near the site of damaged tissue (e.g., cardiac tissue), wounds (e.g., accidental wounds, surgical wounds, or wounds resulting from a disease), or ulcers of a subject in need of treatment. The membranes should be large enough to prevent the protease-resistant SDF-1 from being washed away by bodily fluids, and a sufficient amount of mSDF-1 should be present to promote the migration of, for example, T cells to the site of injury.

Peptide Synthesis

The self-assembling and protease-resistant SDF-1 peptides of the present invention can be made by solid-phase peptide synthesis using, for example, standard N-tert-butyoxycarbonyl (t-Boc) chemistry and cycles using n-methylpyrolidone chemistry. Exemplary methods for synthesizing peptides are found, for example, in U.S. Pat. Nos. 4,192,798; 4,507,230; 4,749,742; 4,879,371; 4,965,343; 5,175,254; 5,373,053; 5,763,284; and 5,849,954, hereby incorporated by reference.

Once peptides have been synthesized, they can be purified using procedures such as, for example, high pressure liquid chromatography (HPLC) on reverse-phase columns. Purity may also be assessed by HPLC, and the presence of a correct composition can be determined by amino acid analysis. A purification procedure suitable for mSDF-1 peptides is described in, for example, U.S. Patent Application Publication No. 2008/0095758, hereby incorporated by reference.

Fusion proteins may either be chemically synthesized or made using recombinant DNA techniques. The full sequences of these proteins are described herein. Non-limiting examples of fusion protein DNA and amino acid sequences are provided below.

```
SSDF-1-6G-RAD16-I ("6G" disclosed as SEQ ID NO: 57;
sequence disclosed as SEQ ID NO: 72)
agc aag ccg gtc agc ctg agc tac cgt tgc cca tgc cgt ttc ttc gaa agc cat gtt gcc cgc gcc aac gtc aag cat ctc aaa att ctc aac act cca aac tgt gcc ctt cag att gta gcc cgt ctg aag aac aac aac cgc caa gtg tgc att gac ccg aag ctg aag tgg att cag gag tac ctg gag aaa gct tta aac aag GGA GGC GGG

GGA GGT GGG CGT GCC GAC GCT CGC GCA GAT GCG CGT

GCC GAC GCT CGG GCA GAT GCG TGA

Corresponding SSDF-1-6G-RAD16-I Amino Acid
Sequence ("6G" disclosed as SEQ ID NO: 57;
sequence disclosed as SEQ ID NO: 73)
S K P V S L S Y R C P C R F F E S H V A R A N V K

H L K I L N T P N C A L Q I V A R L K N N N R Q V

C I D P K L K W I Q E Y L E K A L N K G G G G G G

R A D A R A D A R A D A R A D A

SSDF-1(S4V)-6G-RAD16-I ("6G" disclosed as SEQ ID
NO: 57; sequence disclosed as SEQ ID NO: 74)
agc aag ccg gtc gtc ctg agc tac cgt tgc cca tgc cgt ttc ttc gaa agc cat gtt gcc cgc gcc aac gtc aag cat ctc aaa att ctc aac act cca aac tgt gcc ctt cag att gta gcc cgt ctg aag aac aac aac cgc caa gtg tgc att gac ccg aag ctg aag tgg att cag gag tac ctg gag aaa gct tta aac aag GGA GGC GGG

GGA GGT GGG CGT GCC GAC GCT CGC GCA GAT GCG CGT

GCC GAC GCT CGG GCA GAT GCG TGA

Corresponding SSDF-1(S4V)-6G-RAD16-I Amino Acid
Sequence ("6G" disclosed as SEQ ID NO: 57;
sequence disclosed as SEQ ID NO: 75)
S K P V V L S Y R C P C R F F E S H V A R A N V

K H L K I L N T P N C A L Q I V A R L K N N N R

Q V C I D P K L K W I Q E Y L E K A L N K G G G

G G G R A D A R A D A R A D A R A D A
```

Nucleic Acids

The invention also features nucleic acids with a nucleotide sequence encoding any of the protease-resistant peptides or fusion proteins described above, vectors (e.g., Champion pET Sumo vectors (Invitrogen), pET101/D-TOPO vectors (Invitrogen), or pTrcHis or pTrcHis2 vectors) in which these nucleic acids are operably linked to a promoter sequence, and host cells (e.g., cell-free expression systems, prokaryotic expression systems (e.g., *E. coli* BL21, BL21-DE3, BL21Star, or BL21pLys), yeast expression systems (e.g., *Pichia pastoris*), baculovirus expression systems, or mammalian expression systems (e.g., transient expression in HEK293E cells or a stable CHO cell line)) transformed with the vector.

Exemplary nucleotide sequences of the peptides or fusion proteins of the invention are provided below and throughout the specification. Any of the codons can be mutated without changing the protein sequence following the genetic code.

SDF-1 native (SEQ ID NO: 76)
aag ccc gtc agc ctg agc tac aga tgc cca tgc cga ttc ttc gaa agc cat gtt gcc aga gcc aac gtc aag cat ctc aaa att ctc aac act cca aac tgt gcc ctt cag att gta gcc cgg ctg aag aac aac aac aga caa gtg tgc att gac ccg aag cta aag tgg att cag gag tac ctg gag aaa gct tta aac aag tga SDF-1 codon optimized, excluding rare E. coli codons (SEQ ID NO: 77)
aag ccg gtc agc ctg agc tac cgt tgc cca tgc cgt ttc ttc gaa agc cat gtt gcc cgc gcc aac gtc aag cat ctc aaa att ctc aac act cca aac tgt gcc ctt cag att gta gcc cgt ctg aag aac aac aac cgc caa gtg tgc att gac ccg aag ctg aag tgg att cag gag tac ctg gag aaa gct tta aac aag tga SSDF-1 codon optimized, excluding rare E. coli codons (SEQ ID NO: 78)
agc aag ccg gtc agc ctg agc tac cgt tgc cca tgc cgt ttc ttc gaa agc cat gtt gcc cgc gcc aac gtc cat ctc aaa att ctc aac act cca aac tgt gcc ctt cag att gta gcc cgt ctg aag aac aac aac cgc caa gtg tgc att gac ccg aag ctg aag tgg att cag gag tac ctg gag aaa gct tta aac aag tga SDF-1(S4V) codon optimized, excluding rare E. coli codons (SEQ ID NO: 79)
aag ccg gtc gtc ctg agc tac cgt tgc cca tgc cgt ttc ttc gaa agc cat gtt gcc cgc gcc aac gtc aag cat ctc aaa att ctc aac act cca aac tgt gcc ctt cag att gta gcc cgt ctg aag aac aac aac cgc caa gtg tgc att gac ccg aag ctg aag tgg att cag gag tac ctg gag aaa gct tta aac aag tga SSDF-1(S4V) codon optimized, excluding rare E. coli codons (SEQ ID NO: 80)
agc aag ccg gtc gtc ctg agc tac cgt tgc cca tgc cgt ttc ttc gaa agc cat gtt gcc cgc gcc aac gtc aag cat ctc aaa att ctc aac act cca aac tgt gcc ctt cag att gta gcc cgt ctg aag aac aac aac cgc caa gtg tgc att gac ccg aag ctg aag tgg att cag gag tac ctg gag aaa gct tta aac aag tga Example of RADARADARADARADA (SEQ ID NO: 9) nucleic acid sequence (SEQ ID NO: 81)
cgt gcc gac gct cgc gca gat gcg cgt gcc gac gct cgg gca gat gcg Example of RARADADARARADADA (SEQ ID NO: 35) nucleic acid sequence (SEQ ID NO: 82)
cgt gcc gct gcc gac gcc gac gcc cgt gcc cgt gcc gac gcc gac gcc Pharmaceutical Compositions and Dosages Any of the peptides employed according to the present invention may be contained in any appropriate amount in any suitable carrier substance, and the protease-resistant peptides or fusion proteins of the invention are generally present in an amount of 1-95% by weight of the total weight of the composition, e.g., 5%, 10%, 20%, or 50%. The protease-resistant SDF-1 peptides or fusion proteins of the present invention may be incorporated into a pharmaceutical composition containing a carrier such as, e.g., saline, water, Ringer's solution, and other agents or excipients. The dosage form will generally be designed for implantation or injection (e.g., intravenous, intra-arterial, and/or intracoronary injection), particularly into cardiac tissue, but topical treatments will also be useful, e.g., in the treatment of wounds. Additionally, the composition may be provided in a dosage form that is suitable for the oral, parenteral, intrathecal, rectal, cutaneous, nasal, vaginal, inhalant, skin (e.g., patch), or ocular administration route. Thus, the composition may be in the form of, e.g., tablets, capsules, pills, powders, granulates, suspensions, emulsions, solutions, gels (e.g., hydrogels), pastes, ointments, creams, plasters, drenches, osmotic delivery devices, suppositories, enemas, injectables, implants, sprays, or aerosols. All dosage forms may be prepared using methods that are standard in the art (see, e.g., Remington's Pharmaceutical Sciences, 16th ed., A. Oslo. ed., Easton, Pa. (1980)).

The peptides of the invention can be delivered in a controlled-release or sustained-release system. For example, polymeric materials can be used to achieve controlled or sustained release of the peptides (see, e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); U.S. Pat. Nos. 5,679,377; 5,916,597; 5,912,015; 5,989,463; and 5,128,326; PCT Publication Nos. WO 99/15154 and WO 99/20253, hereby incorporated by reference). Examples of polymers used in sustained-release formulations include, e.g., poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), polyglutamic acid (PGA), and polyorthoesters.

It is expected that the skilled practitioner can adjust dosages on a case by case basis using methods well established in clinical medicine. The optimal dosage may be determined by methods known in the art and may be influenced by factors such as the age of the subject being treated, disease state, and other clinically relevant factors. Generally, when administered to a human, the dosage of any of the therapeutic agents (e.g., protease-resistant SDF-1 peptides) of the invention will depend on the nature of the agent and can readily be determined by one skilled in the art. Typically, such dosage is normally about 0.001 µg to 2000 mg per day, about 0.001 mg to 1000 mg per day, or about 0.5 to 500 mg per day. In various embodiments, the dosage is about 1 mg to 100 mg per day or about 5 mg to 500 mg per day. The dosages can also be expressed as mg/kg and examples of such dosages include 0.001 mg/kg per day to 100 mg/kg per day, 0.001 mg/kg per day to 50 mg/kg per day, and 0.01 mg/kg per day to 10 mg/kg per day.

The peptides of the invention may be administered once, twice, three times, four times, or five times each day; once per week, twice per week, three times per week, four times per week, five times per week, or six times per week; once per month, once every two months, once every three months, or once every six months; or once per year. Alternatively, the peptides of the invention may be administered one or two times and repeated administration may not be needed. Administration of the peptides of the invention can continue until tissue damage (e.g., tissue damage resulting from myocardial infarction or peripheral vascular disease) has healed or has been ameliorated. The duration of therapy can be, e.g., one week to one month; alternatively, the peptides of the invention can be administered for a shorter or a longer duration. Continuous daily dosing with the peptides described herein may not be required. A therapeutic regimen may require cycles, during which time a composition is not administered, or therapy may be provided on an as-needed basis.

Appropriate dosages of the peptides used in the methods and compositions described herein depend on several factors, including the administration method, the severity of the disorder, and the age, weight, and health of the subject to be treated. Additionally, pharmacogenomic information (e.g., the effect of genotype on the pharmacokinetic, pharmacodynamic, or efficacy profile of a therapeutic) about a particular subject may affect the dosage used.

Diagnosis and Treatment

The compositions of the present invention are useful for treating any subject that has been diagnosed with or has suffered from tissue damage (e.g., damage to cardiac tissue due to myocardial infarction or tissue damage resulting from peripheral vascular disease) or wounds. Tissue damage may be the result of, for example, a cardiovascular condition (e.g., myocardial infarction); peripheral vascular disease (PVD); peripheral artery disease (PAD); ulcers (e.g., ulcers of the gastrointestinal tract); surgery; or diabetes. The compositions of the present invention may be used to promote wound healing or tissue repair. One skilled in the art will understand that subjects of the invention may have been subjected to standard tests or may have been identified, without examination, as one at high risk due to the presence of one or more risk factors. Diagnosis of these disorders may be performed using any standard method known in the art.

The compositions described herein may also be used to treat any disease or condition characterized by a high concentration of protease (e.g., MMP-2, MMP-9, DPPIV, leukocyte elastase, cathepsin G, carboxypeptidase M, and/or carboxypeptidase N), where the attraction of stem cells upon the administration of a protease-resistant SDF-1 peptide may induce regeneration or healing. Exemplary disorders to be treated by compositions of the present invention include inflammatory and ischemic diseases (e.g., stroke or limb ischemia), wound healing, and diabetic ulcers.

The protease-resistant SDF-1 peptides of the present invention may be used in combination with additional therapies to promote wound healing or tissue repair. Treatment therapies that can be used in combination with the methods of the invention include, but are not limited to heparin, β-blockers (e.g., atenolol, metoprolol, nadolol, oxprenolol, pindolol, propranolol, or timolol), angiotensin-converting enzyme (ACE) inhibitors (e.g., captopril, enalapril, fosinopril, lisinopril, perindopril, quinapril, ramipril, trandolapril, or benazepril), angiotensin II receptor blockers (e.g., candesartan, eprosartan, irbesartan, losartan, olmesartan, telmisartan, or valsartan), diuretics, aspirin, cholesterol-lowering drugs (e.g., HMG-CoA reductase inhibitors (e.g., atorvastatin, cerivastatin, fluvastatin, lovastatin, mevastatin, pitavastatin, pravastatin, rosuvastatin, or simvastatin)), cell therapy, anti-platelet drugs (e.g., clopidogrel, prasugrel, ticlopidine, cilostazol, abciximab, eptifibatide, tirofiban, or dipyridamole), anti-hypertensive drugs, anti-arrhythmic drugs (e.g., quinidine, procainamide, disopyramide, lidocaine, mexiletine, tocainide, phenytoin, moricizine, flecainide, sotalol, ibutilide, amiodarone, bretylium, dofetilide, diltiazem, or verapamil), angiogenic drugs, wound dressings, PDGF, and/or negative pressure devices and therapies.

EXAMPLES

The present invention is illustrated by the following examples, which are in no way intended to be limiting of the invention.

Example 1. Initial Cleavage Rates of a FRET-Based Peptide Library

Peptides containing the first 8 amino acids of SDF-1 (KPVSLSYR (SEQ ID NO: 89)) and all possible single amino acid mutations at position 3, 4, 5, or 6 (spanning the MMP-2 cleavage site) were synthesized, 77 peptides total (Anaspec, San Jose, Calif.). All peptides were synthesized with a fluorescent 7-methoxycoumarin-3-carboxylic acid (MCA) residue at the N-terminus and a quencher lysine-dinitrophenol (Dpn) residue at the C-terminus. Purity of peptides was confirmed with HPLC and mass spectrometry. Enzymatic cleavage of these peptides separated MCA from Dpn, resulting in an increased fluorescence. Peptides (10 µM) were then incubated with activated MMP-2 (Table 1), leukocyte elastase (Table 2), or cathepsin G (Table 3) (1.4 nM) in TNCB buffer (50 mM Tris, pH 7.5, with 10 mM calcium chloride, 150 mM sodium chloride, and 0.05% BRIJ 35) or phosphate-buffered saline (PBS) at 21° C. Fluorescence was measured at 340 nm excitation and 405 nm emission wavelengths at different time points with a Victor Wallace II plate reader. Initial cleavage rates (fluorescence per unit of time) were normalized to the cleavage rate of peptides containing the first 8 amino acids of SDF-1 (100%).

The results are shown in FIGS. 9A-9C. Column headers show the site of the mutation(s) and the row title shows the mutated amino acid in that position. Mutations with an initial cleavage rate of less than 10% are indicated in italics and mutations with an initial cleavage rate between 10% and 20% of SDF-1 analogue are indicated in grey shading.

Example 2. Identification and Characterization of SDF-1 Variants Resistant to MMP-2 Cleavage The site where SDF-1 is cleaved by MMP-2, leukocyte elastase, and cathepsin G is also the receptor binding site of SDF-1. Thus, mutations that make SDF-1 resistant to proteases may also interfere with receptor binding and activation. Based on the FRET-peptide library initial cleavage rates, mutations were selected for cloning into an *E. coli* expression vector. Proteins were expressed in *E. coli* and purified with cation-exchange chromatography and reverse-phase HPLC. Activity of these proteins was tested in a Jurkat T-lymphocyte migration assay, CXCR4 (cAMP) receptor activation assay, and CXCR7 β-arrestin binding assay. For these experiments and other experiments described herein, data were analyzed with 2-tail t-tests if 2 independent samples were compared and with one-way ANOVA if more than 2 independent samples were present, followed by multiple comparisons with Bonferroni corrections. Data are presented as mean±SEM.

For the Jurkat T-lymphocyte migration assay, the activity of purified SDF-1 variants was tested by migration of Jurkat T-lymphocytic cells in a ChemoTx chemotaxis system (5 μm pore, Neuro Probe, Gaithersburg, Md.). Jurkat cells were labeled with Calcein-AM (1 μM) for 60 minutes at 37° C., washed twice and resuspended in RPMI without phenol red to a final density of 4,000,000 cells/ml. 50 μl of this cell suspension was added to upper wells, and different concentrations of SDF-1 variants were added to lower wells. Cells were allowed to migrate for 3 hours, and cells in lower wells were washed once with PBS. Fluorescence in lower wells was measured at 485 nm excitation and 535 nm emission wavelengths with a Victor Wallace II plate reader. A standard curve was constructed for each experiment to normalize fluorescence to the number of cells.

For the CXCR4 cAMP assay, CHO-K1 cells stably expressing the CXCR4 receptor (DiscoveRx, Fremont, Calif.) were seeded at a density of 10,000 cells/well in a 384-well plate and were allowed to recover overnight. A decrease in cAMP by CXCR4-induced Gαi activation was determined using the DiscoveRx HitHunter cAMP XS+assay following the manufacturer's protocol. Forskolin (an inducer of cAMP) concentration-response curves were generated to determine the $EC_{80}$ concentration for subsequent testing with SDF-1 variants. The cells were incubated in the presence of SDF-1 variants and forskolin (at $EC_{80}$ concentration) at 37° C. for 30 minutes. After the incubation period, assay signal was generated through incubation with 20 μL cAMP XS+ED/CL lysis cocktail for one hour followed by incubation with 20 μL cAMP XS+EA reagent for a three-hour incubation at 21° C. Chemiluminescence was read with a PerkinElmer ViewLux instrument.

For the CXCR4, CXCR7, CXCR3, and CXCR1 β-arrestin recruitment assays, activation of CXCR4, CXCR7, CXCR3, and CXCR1 receptors by SDF-1 variants was detected by measuring β-arrestin recruitment to the receptors. PathHunter β-arrestin assays were performed following the instructions of the manufacturer (DiscoveRx). Briefly, PathHunter cell lines stably expressing both a β-arrestin-Enzyme Acceptor of β-galactosidase fusion and one of the chemokine receptors fused with the ProLink donor peptide of β-galactosidase were employed. Upon CXCR stimulation, β-arrestin is recruited to the receptor for desensitization, bringing the two fragments (the Enzyme Acceptor and the ProLink) of β-galactosidase together. This generates an active β-galactosidase enzyme that can convert a substrate to a chemiluminescent product. Cells were seeded at a density of 5000 cells/well in a 384-well plate and were allowed to adhere overnight. Cells were incubated in the presence of different concentrations of SDF-1 variants at 37° C. for 90 minutes. After incubation, chemiluminescent signal was generated through addition of 12.5 μl (50% v/v) of PathHunter Detection reagent cocktail (DiscoveRx) followed by a 1-hour incubation at room temperature. Microplates were read with a PerkinElmer ViewLux instrument.

The results of these assays are described in Tables 1 and 2.

TABLE 1

Mutants described in Segers et at. (*Circulation* 116: 1683-1692, 2007)

| Protein | Resistance | Jurkat Chemotaxis $EC_{50}$ (nM) | CXCR4 (cAMP) $EC_{50}$ (nM) | CXCR7 β-arrestin $EC_{50}$ (nM) |
|---|---|---|---|---|
| SDF-1 | — | 1.5 | 5.4 | 22 |
| SSDF-1 | DPPIV | 1.6 | 1.2 | 20 |
| SSDF-1 (S4V) | DPPIV, MMP-2 | 5.4 | 20 | 37 |
| SSDF-1 (L5P) | DPPIV, MMP-2, elastase, cathepsin G | 120 | Inactive | 225 |
| SSDF-1 (L5E) | DPPIV, MMP-2, elastase, cathepsin G | Inactive | — | — |
| SSDF-1 (L5W) | DPPIV, MMP-2 | Inactive | — | — |

TABLE 2

Identified mutants (resistance profile based on FRET-peptide cleavage assay)

| Protein | Resistance | Jurkat Chemotaxis $EC_{50}$ (nM) | CXCR4 (cAMP) $EC_{50}$ (nM) | CXCR7 β-arrestin $EC_{50}$ (nM) |
|---|---|---|---|---|
| SSDF-1 (V3H) | DPPIV, elastase | 6.7 | 1 | 92 |
| SSDF-1 (V3C) | DPPIV, elastase | 15 | 0.6 | 14 |
| SSDF-1 (L5T) | DPPIV, MMP-2, Cathepsin G | 20 | 3.6 | 8.7 |
| SSDF-1 (L5V) | DPPIV, MMP-2, Cathepsin G | 36 | 33 | 21 |
| SSDF-1 (S6C) | DPPIV, MMP-2 | 23 | 12 | 29 |
| SSDF-1 (S6G) | DPPIV, MMP-2, Cathepsin G | 11 | 8.5 | 25 |
| SSDF-1 (V3G) | DDPIV, elastase, Cathepsin G | Inactive | — | — |
| SSDF-1 (V3P) | DPPIV, MMP-2, elastase, Cathepsin G | Inactive | — | — |
| SSDF-1 (V3D) | DPPIV, MMP-2, elastase, Cathepsin G | Inactive | — | — |
| SSDF-1 (L5C) | DPPIV, MMP-2, Cathepsin G | Inactive | — | — |
| SSDF-1 (L5K) | DPPIV, MMP-2, Elastase | Inactive | — | — |
| SSDF-1 (L5H) | DPPIV, MMP-2, Cathepsin G | Inactive | — | — |
| SSDF-1 (L5D) | DPPIV, MMP-2, Elastase, Cathepsin G | Inactive | — | — |

Mutated variants of SDF-1 identified as being inactive in the Jurkat cell migration assay included SSDF-1(V3D), SSDF-(L5C), SSDF-1(L5D), SSDF-1(L5E), SSDF-1(L5H), SSDF-1(L5K), SSDF-1(L5W), SSDF-1(V3G), and SSDF-1 (V3P). SSDF-1(S4V) was identified as the mutated variant with the highest potency in the Jurkat cell migration assay.

Example 3. SSDF-1(S4V) has the Same Receptor Specificity as Native SDF-1

The activity of SSDF-1(S4V) was evaluated in Jurkat cell migration assays (FIG. 2A) and CXCR4 and CXCR7 receptor activation assays and compared to native SDF-1 and SSDF-1, as described above. The $EC_{50}$ for CXCR4 receptor activation was 20 nM with SSDF-1(S4V) compared to 5.4 nM for SDF-1 (measured by the decrease in cAMP by Gi activation; FIG. 2B) and 28 nM for SSDF-1(S4V) compared to 3.8 nM for SDF-1 (measured by binding of β-arrestin to the CXCR4 receptor, FIG. 2C). Together, these data indicate that SSDF-1(S4V) is an agonist of CXCR4, but with nanomolar potency that is 4- to 7-fold lower than native SDF-1. Compared to SDF-1, SSDF-1(S4V) has similar potency on CXCR7 binding to β-arrestin (FIG. 2D). SSDF-1, which is different from native SDF-1 by an extra serine at the N-terminus, which provides resistance against DPPIV, had a similar profile in Jurkat cell migration experiments. To rule out a shift in CXCR receptor specificity induced by SDF-1 mutations, we examined activity of the SDF-1 variants on CXCR1 and CXCR3, which are normally not activated by SDF-1. As anticipated, the SDF-1 variants tested did not activate CXCR1 or CXCR3.

Example 4. SSDF-1(S4V) is Resistant to MMP-2 Cleavage

We determined MMP-2 cleavage rates of SDF-1, SDF-1 (S4V), Sumo-SDF-1-RAD, and Sumo-SDF-1(S4V)-RAD using a FRET-based peptide substrate cleavage assay.

Sumo-SDF-1-RAD and Sumo-SDF-1(S4V)-RAD were constructed as described previously (see, e.g., Segers et al., *Circulation* 116: 1683-1692, 2007). The DNA sequence of mature SDF-1α was cloned from human cDNA into the pET-Sumo vector (Invitrogen). Sequences coding for an additional serine at the N-terminus were incorporated to increase resistance to DPPIV cleavage (SSDF-1). Because the active site of SDF-1 is within the N-terminal domain, fusion proteins designed to lock SDF-1 into self-assembling peptide nanofibers for sustained-release applications were made by incorporating extra sequences at the C-terminus. Fusion proteins included the SDF-1 sequence and the RAD16-I or RAD16-II sequence (Segers et al., *Drug Discov Today* 12: 561-568, 2007). SDF-1 was separated from RAD by a flexible linker, containing six glycine residues. To make SDF-1 resistant to MMP-2 cleavage, mutagenesis of the amino acids at positions 3 to 6 was performed as described previously (Segers et al., *Circulation* 116: 1683-1692, 2007). All sequences were confirmed by DNA sequencing.

Sumo-SSDF-1 fusion proteins were expressed in BL21 *E. coli* cells (Sigma) and grown to an optical density of 1.5 (at 600 nm) at 37° C. Cells were induced with 0.25 mM isopropyl β-D-thiogalactoside (IPTG) overnight and harvested by centrifugation. SSDF-1 was purified using a 3-step procedure; all steps were performed at 21° C. Cells from a 6-L growth were lysed by sonication in lysis buffer (PBS, 10 μg/ml DNAse, 1 mM PMSF, 100 μg/ml lysozyme), and inclusion bodies were isolated by centrifugation and washed twice with wash buffer (PBS, 0.5% Triton-X 100). The second purification and refolding step was performed on a cation-exchange HPLC column (HiPrep 16/10SP-FF, Amersham). The inclusion bodies were dissolved in binding buffer (8 M urea, 30 mM 2-mercaptoethanol, 1 mM EDTA, 50 mM Tris, pH 8) and loaded onto the column. Refolding of Sumo-SSDF-1 was performed on the column with a 0-100% gradient of refolding buffer (50 mM Tris, pH 8, 75 mM NaCl, 0.1 mM reduced glutathione, and 0.1 mM oxidized glutathione). Sumo-SSDF-1 was eluted with a gradient of 0.1-1 M NaCl. The Sumo-SSDF-1 fusion protein was cleaved by Sumo Protease (1 U/50 μg protein, Lifesensors) in 50 mM Tris, pH 8.0, and 500 mM NaCl. The sample was adjusted to 0.1% trifluoroacetic acid (TFA) and loaded onto a C18 reverse-phase HPLC column (XTerra-Prep-MS 5 μm 7.8×150 mm, Waters) as a final purification step. The column was subjected to a linear gradient from 30-40% acetonitrile in 0.1% TFA.

Human recombinant MMP-2 (R&D Systems) was activated for 1 hour with 4-aminophenylmercuric acetate (APMA, 1 mM) at 37° C. 4 μg of Sumo-SSDF-1-RAD or Sumo-SSDF-1(S4V)-RAD was incubated for 1 hour to 48 hours at 21° C. with 50 ng of activated MMP-2 in TCNB buffer (50 mM Tris, pH 7.5, 10 mM $CaCl_2$, 150 mM NaCl, 0.05% Brij-35). Sample loading buffer (Invitrogen) and 2-mercaptoethanol (0.5 M, final concentration) were added, and samples were boiled for 5 minutes and run on a 10% Bis-Tris gel. Proteins used for this experiment were obtained after cation-exchange chromatography, but were neither cleaved by Sumo-protease nor purified by RPC-HPLC.

Synthetic peptides consisting of the first 8 amino acids of SDF-1 or SDF-1(S4V) with a fluorescent dye (MCA) at the N-terminus and a quencher (Dpn) at the C-terminus were incubated with MMP-2, and accumulation of fluorescence by peptide cleavage was measured. After 4 hours, 205±18 pmol of the SDF-1-N-terminal peptide was cleaved, whereas no significant amount (1±3 pmol) of the SDF-1 (S4V)-N-terminal peptide was cleaved (n=4; FIG. 3A). The initial cleavage rate was $2.0 \pm 0.1 \times 10^{-10}$ M $s^{-1}$ for the SDF-1-N-terminal peptide and $0.1 \pm 0.1 \times 10^{-10}$ M $s^{-1}$ for the SDF-1 (S4V)-N-terminal peptide (p<0.0001, n=4; FIG. 3B). Cleavage rates were also evaluated by incubation of complete Sumo-SDF-1-RAD or Sumo-SDF-1(S4V)-RAD proteins with MMP-2 followed by separation of cleaved fragments with SDS-PAGE (FIGS. 3C and 3D). Under identical conditions, more Sumo-SDF-1-RAD was cleaved within 1 hour than Sumo-SDF-1(S4V)-RAD in 48 hours, indicating that the rate of SDF-1(S4V) cleavage is at least 48 times lower than SDF-1.

Example 5. SDF-1 Variants are Angiogenic In Vivo

Eight week-old, female C57BL/6 mice were purchased from Charles River Laboratories. Matrigel™ Matrix High Concentration (BD Biosciences, Cat. No. 354234) was mixed with heparin at 3 ng/ml and with different SDF-1 variants at assigned concentrations and kept at 4° C. Each mouse was implanted subcutaneously bilaterally (in the right and left flanks) with 0.5 ml of Matrigel™ using a 23-gauge needle. The injection was done rapidly to ensure that the entire content was delivered in one plug. Formed plugs from each mouse were collected on Day 10. Mice were euthanized by inhalation of $CO_2$ and mouse skin was pulled back to expose the plugs. The intact plugs were removed and the two plugs from each mouse were fixed in 10% buffered formalin. Matrigel™ plugs were embedded in paraffin blocks and 4-μm thickness slides were prepared. Sections collected around the center part of each plug were processed with antigen retrieval and then immunostained with a specific antibody against CD31 (BD Biosciences, Cat. No. 550274) and counterstained with hematoxylin and eosin stain. The number of CD31-positive blood vessels in one entire section of each Matrigel™ plug was counted under a microscope. The average number of vessels for each mouse group was calculated. The experiment was performed by operators unaware of the treatment groups.

FIG. 4 illustrates the results of a Matrigel™ plug assay showing new vessel formation with different SDF-1 variants (200 ng/ml) in vivo. FIG. 5 illustrates the results of a Matrigel™ plug assay showing new vessel formation with different SDF-1 variants in vivo at different dosages (e.g., 20, 67, 200, and 600 ng/ml).

Example 6. SSDF-1-RAD Fusion Proteins Stably Incorporate into Self-Assembling Peptides To study release kinetics of nanofiber hydrogels, FITC-labeled self-assembling peptides (FITC-RAD) were incorporated into a nanofiber gel in cell culture inserts. Fusion proteins of SSDF-1 and the sequence of self-assembling peptides (called SSDF-1-RAD) for prolonged in vivo delivery were reported previously, but without detailed release kinetics (Segers et al., *Circulation* 116: 1683-1692, 2007).

The Ac-RADARADARADARADA-CONH2 (RAD16-I) peptide (SEQ ID NO: 9) in 1% solution was obtained from PuraMatrix™ (BD BioSciences) and Ac-RARADADARA-RADADA-CONH2 (RAD16-II) (SEQ ID NO: 35) and FITC-Ahx-RARADADARARADADA (FITC-RAD16-11) (SEQ ID NO: 90) from Celtek Bioscience. SSDF-1 and SSDF-1-RAD were labeled using the Alexa Fluor-488 microscale protein-labeling kit (Invitrogen) with minor modifications. Proteins were labeled with Alexa-488-sulfo-dichlorophenol ester, and unreacted dye molecules were removed by gel filtration (Bio-Gel P-4, Bio-Rad). For the in vitro binding experiment, self-assembling peptides (RAD16-II) were dissolved in 295 mM sucrose in water. The peptide solution was mixed with 100 nM of Alexa-488 labeled SSDF-1, Alexa-488 labeled SSDF-1-RAD proteins, or unreacted Alexa-488 as a control. 100 µl of this self-assembling peptide solution was added to a 0.4-µm pore size culture plate insert (Millicell-CM, Millipore) and left overnight at 4° C. to allow formation of nanofibers. Inserts were transferred to a well containing 300 µl of fresh PBS every 15 minutes. Fluorescence in PBS wash fractions and fluorescence remaining in self-assembling peptides at the end of a 24-hour experiment were measured with a Victor Wallace plate reader. The same experiment was performed with FITC-labeled RAD16-II peptides instead of Alexa-488-labeled SSDF-1 and SSDF-1-RAD, with a final concentration of 100 to 1000 nM of FITC-RAD in a hydrogel of unlabeled self-assembling peptides.

Figures 6A, 6B, 6C, 6D:
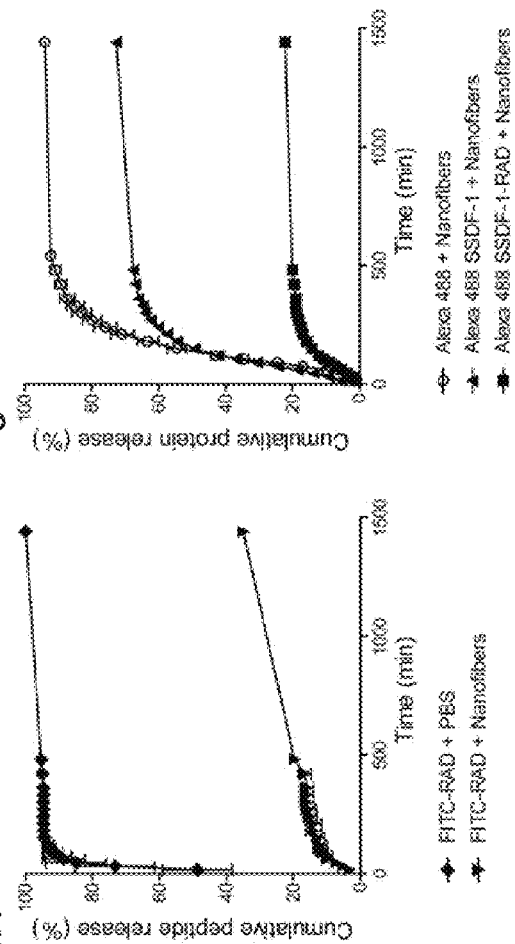
FIGS. 6A-6D are graphs and images showing SSDF-1-RAD stably incorporated into nanofibers.

For the FITC-RAD experiment, the starting concentration was 100 nM of FITC-RAD in a hydrogel of 1% (w/v) nanofibers. 100 nM of FITC-RAD in PBS was included as a control group. Cumulative release of FITC-RAD was measured over a period of 24 hours. Without nanofibers, 100 nM of FITC-RAD diffused through the insert membranes in the first 3 to 4 wash fractions (FIG. 6A). When incorporated into the nanofibers, 19.7±1.3% of FITC-RAD diffused out in the first 8 hours and 35±1.2% in the first 24 hours. 65% of the initial amount of FITC-RAD was still incorporated in the nanofibers after 24 hours.

SSDF-1 and SSDF-1-RAD were labeled with Alexa-488 and 100 nM of each protein was mixed with a hydrogel of nanofibers. Non-protein-bound Alexa-488 in nanofibers was included as a control group. Cumulative protein release was measured in the same manner as described for the experiment with FITC-RAD. Within 8 hours, almost all of the small molecule Alexa-488 was released from the nanofibers (FIG. 6B). 73±0.8% of SSDF-1, compared to only 22±1.4% of SSDF-1-RAD fusion protein, was released over 24 hours; most of the released protein diffused out in the first 4 hours with little release thereafter. 78% of the SSDF-1-RAD fusion protein was stably incorporated into the nanofibers (FIG. 6B).

To evaluate if nanofibers allow for prolonged delivery of proteins in vivo, 50 µl of a 1% nanofiber hydrogel with 0.01% biotin-RAD (1% of the peptides were biotinylated) was injected into the calf muscle of 35 mice after excision of the femoral artery. Tissue sections were made at seven different time points and nanofibers were identified with Alexa-labeled streptavidin. The amount of nanofibers remaining at different time points was measured by determining the total surface of biotin-RAD normalized to d0 (FIG. 6C). The nanofiber content found in the calf muscle did not decrease significantly over the first 7 days (FIG. 6D), but decreased significantly between 7 and 14 days and had mostly disappeared at 3 weeks post surgery. Collectively, these data indicate that nanofiber hydrogels can be used for delivery of proteins or peptides for 14 days in ischemic hindlimbs.

Example 7. SSDF-1(S4V)-RAD Increases Blood Flow in a Hindlimb Ischemia Model

We tested protease-resistant SSDF-1(S4V)-RAD fusion protein delivered with nanofibers in a mouse model of hindlimb ischemia.

All animal protocols were approved by the institutional IACUC and performed in an AAALAC certified facility. Studies were performed blinded and randomized. Hindlimb ischemia was produced in male C57BL/6 mice (305 mice total), 8 to 12 weeks old (Jackson Laboratories and Charles River Laboratories). Mice were anesthetized with isoflurane (2-3% in 100% oxygen) and buprenorphin (0.05 mg/kg). Femoral artery was ligated and excised below the inguinal ligament and above the bifurcation of the popliteal artery. Protein and self-assembling peptide nanofibers were injected in the lower hindlimb after excision of the artery. Peptides were dissolved in isotonic sucrose (10%). Post-operative analgesia was provided with buprenorphin (0.05 mg/kg every 6 to 12 hours for 72 hours). The surgeon was blinded to the treatment groups in all studies performed. The first study included 35 animals total (5 animals per group), which received an intramuscular injection in the lower hindlimb with biotin-labeled nanofibers (biotin-RAD, 0.01% in 1% nanofibers hydrogel). Tissues were harvested at seven different time points and nanofibers were stained with Alexa fluor-labeled streptavidin. The second study included 40 animals (10 per group) with four groups: control without injection, nanofibers only, nanofibers+100 nM SSDF-1-RAD, and nanofibers+100 nM SSDF-1(S4V)-RAD. Laser Doppler blood flow measurements were performed with a Moor LDI2-IR (Moor Instruments) 2, 4, and 6 weeks after surgery. At each time point, five measurements (on average) per animal were made, and blood flow in the ischemic limb was normalized to blood flow in normal limb. The third study included 50 animals with four different dosages of SSDF-1(S4V)-RAD; all groups contained nanofibers. All laser Doppler measurements and histology quantifications were made by an operator blinded to the treatment groups.

We tested the activity of protease resistant SSDF-1(S4V)-RAD fusion protein delivered with nanofibers in a randomized, blinded experiment in mice with hindlimb ischemia. SSDF-1(S4V)-RAD (100 nM in 50 11 of nanofibers) was compared to SSDF-1-RAD, nanofibers only and a control group without injection (10 mice/group, 40 mice total). Four weeks after excision of the femoral artery, SSDF-1(S4V)-RAD delivered with nanofibers significantly increased blood flow as measured by laser Doppler from 29.6±3.4% (ratio of ischemic to control limb) to 45.9±5.4% (p<0.05, FIG. 7B). After 6 weeks, SSDF-1(S4V)-RAD delivered with self-assembling peptides increased blood flow to 55.1±5.7%, which was significantly higher than blood flow in the control group (23.1±1.9%, p<0.001), in the group with nanofibers only (30.5±3.4%, p<0.01), and in the group with SSDF-1-RAD fusion protein without the S4V mutation (36.4±4.7%, p<0.05) (FIGS. 7A and 7B). A second experiment in 50 mice was performed in which four different concentrations of SSDF-1(S4V)-RAD incorporated into nanofibers (10 nM, 30 nM, 100 nM, and 300 nM) were injected in ischemic hindlimbs (10 mice/group). Four weeks after excision of the femoral artery, SSDF-1(S4V)-RAD increased blood flow from 17.8±2.1% in the nanofiber only group to 51±8.5% (p<0.001) in the 100 nM group (FIG. 7C). The other tested concentrations did not significantly differ from the group with nanofibers only. Six weeks after excision, three concentrations of SSDF-1(S4V)-RAD induced a significant increase in blood flow compared to nanofibers only (22.1±2.3%, ischemic vs. control limb): 10 nM (52.0±10.3%, p<0.01 vs. 0 nM), 30 nM (54.8±6.8%, p<0.01 vs. 0 nM), and 100 nM (50.7±4.6%, p<0.01 vs. 0 nM) (FIG. 7C).

We performed another study in 60 mice (10 mice/group, 20 mice in PBS control group) to investigate if delivery of protease resistant SSDF-1(S4V) without nanofibers can improve blood flow in ischemic hindlimb. Mice were injected 4 times (d0, d1, d3, and d5 after ligation of the femoral artery) with either 0.1 mg/kg or 1 mg/kg SSDF-1, SSDF-1(S4V) or PBS. Four weeks after surgery, average blood flow in PBS control mice was 25.2±1.7% (ratio of ischemic to control limb) and 27.1±2.5% in mice that received 4 administrations of 1 mg/kg SSDF-1(S4V). The average of the other groups ranged from 25.1 to 30.3% with no significant differences between groups. This result was confirmed in a similar but separate study in 50 mice (10 mice/group) which included the same doses and administration schedule of SSDF-1 and SSDF-1(S4V). This study also did not show significant differences between groups. To evaluate if the negative results of these 2 studies without self-assembling peptides could be attributed to the doses selected, we performed a third study without self-assembling peptides in 40 mice. Four different doses of SSDF-1 (S4V) (0.1 mg/kg, 0.3 mg/kg, 1 mg/kg, and 3 mg/kg) were administered with the same administration schedule as the previous 2 studies (at d0, d1, d3, and d5). No significant differences in blood flow measured with laser Doppler were present between different groups of animals. To evaluate if the negative results of these studies without self-assembling peptides could be attributed to the administration schedule used, we performed a fourth study without self-assembling peptides in 30 mice. A single dose of SSDF-1 or SSDF-1 (S4V) (1 mg/kg) was administered daily IM for the first 7 days after ligation and excision of the femoral artery. No significant differences in blood flow measured with laser Doppler were present between different groups of animals at different time points after surgery. Collectively, these results indicate that delivery of SSDF-1 or SSDF-1(S4V) without nanofibers is insufficient to improve blood flow in ischemic hindlimbs, and improvements in blood flow may be dependent on methods of delivery of a protease-resistant SDF-1 peptide.

Example 8. SSDF-1(S4V)-RAD Increases the Density of Arterioles

Sections of hindlimb tissue were deparaffinized, rehydrated, and pretreated with boiling 10 mM sodium citrate (pH 7.2) for 30 minutes, followed by incubation with antibodies against α-smooth muscle actin (Sigma, Cat. No. A5228), dystrophin (Abcam, Cat. No. ab5277) at 21° C. for 2 hours, Alexa-Fluor-conjugated secondary antibodies, isolectin, or streptavidin (Invitrogen). After counterstaining with DAPI (0.5 μg/ml), sections were observed under fluorescence microscopy. All quantitative analyses were performed by an observer blinded to the treatment groups.

Figures 8A, 8B:
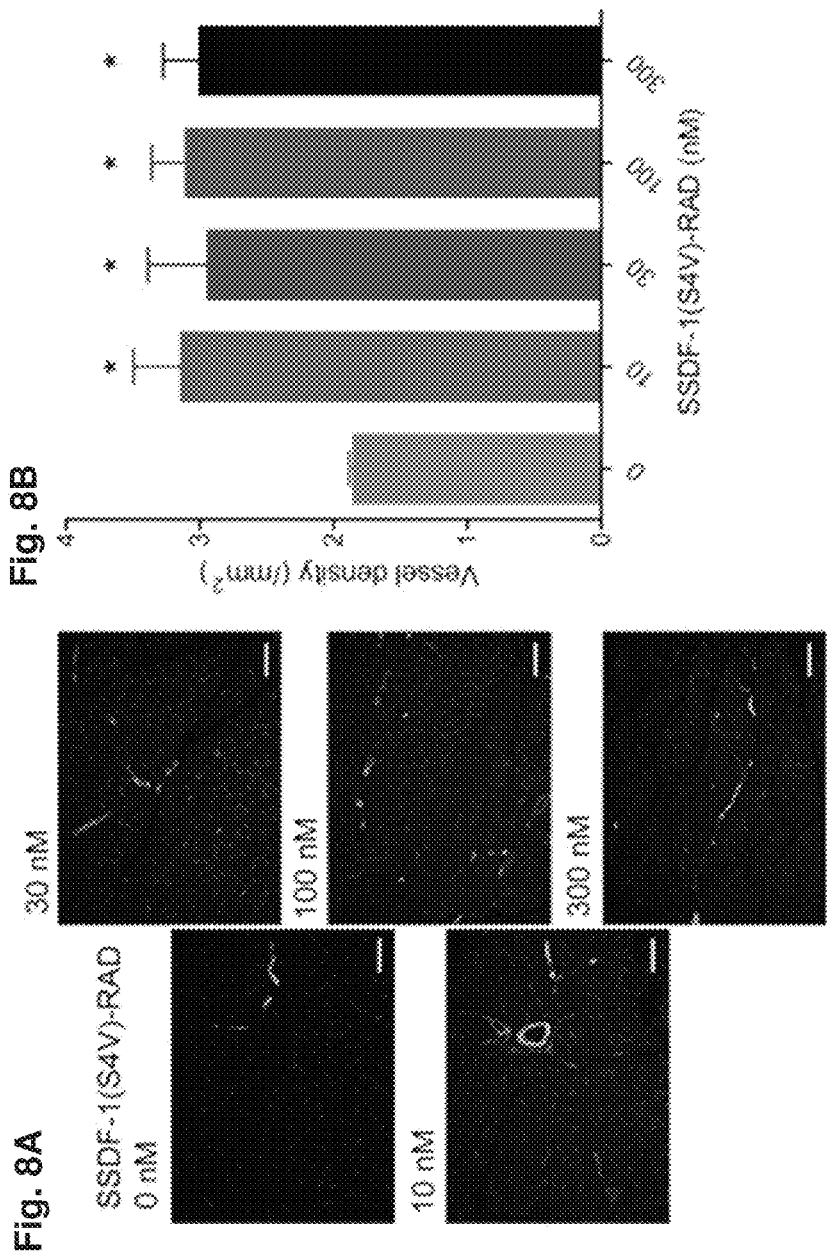
FIGS. 8A-8B are images and graphs showing that SSDF-1(S4V) increases arteriolar density.

Six weeks after excision of the femoral artery, smooth muscle cells and pericytes in the upper hindlimb were stained with an antibody specific for alpha-smooth muscle actin. The density of arterioles/mm$^2$ was significantly increased with the four different dosages of SSDF-1(S4V)-RAD compared to the group with self-assembling peptides only (FIGS. 8A and 8B). Capillaries were stained with Alexa fluor-isolectin, and the number of capillaries was normalized to the number of myocytes (stained with dystrophin). No significant differences were observed in capillary density between different groups. These results indicate that protease resistant SDF-1 induces formation of new arterioles in the ischemic hindlimb.

Example 9. C-Terminal SDF-1 Variants

Carboxypeptidase M and N cleave SDF-1 at the C-terminus (i.e., between the C-terminal asparagine and lysine). We have shown using Jurkat T-lymphocyte migration assays, CXCR4 (cAMP) receptor activation assays, and CXCR4, CXCR7, CXCR1, and CXCR3 β-arrestin binding assays (described above) that the activity of SDF-1 lacking the C-terminal lysine (SSDF-1(−68K)) is unchanged relative to SDF-1 and SSDF-1 (Tables 3 and 4). The addition of amino acid residues to the C-terminal end of SDF-1 (e.g., SSDF-1(+69S)) results in a variant that retains significant activity. We have additionally shown that other C-terminal modifications (e.g., the addition of self-assembling peptide sequences) do not affect SDF-1 activity in vivo. The addition of amino acid residues to the C-terminus of SDF-1 blocks cleavage by carboxypeptidase M and N and may increase the stability of the molecule in vivo. Furthermore, it is expected that C-terminal Fc fusions of SSDF-1 and SSDF-1(S4V) also retain activity.

TABLE 3

Activity of C-terminal SDF-1 variants

| | Chemotaxis (Jurkat) $EC_{50}$ (nM) | CXCR4 (cAMP) $EC_{50}$ (nM) | CXCR4 (β-arrestin) $EC_{50}$ (nM) | CXCR7 (β-arrestin) $EC_{50}$ (nM) |
|---|---|---|---|---|
| SDF-1 | 1.8 | 5.4 | 3.8 | 22 |
| SSDF-1 | 1.6 | 1.2 | 1.5 | 20.0 |
| SSDF-1 (−68K) | 2.2 | 5.6 | ND | 42.2 |
| SSDF-1 (+69S) | 12.0 | 0.35 | ND | 10 |

Other C-terminal variants of SDF-1 and SDF-1(S4V) were made wherein extra amino acid residues were added at the C-terminus. With the exception of the SDF-1γ versions, no significant differences in chemotaxis were observed by the deletion of, for example, one amino acid residue or the addition of 22 amino acid residues (Table 4).

TABLE 4

Activity of C-terminal SDF-1 variants

| Protein | Chemotaxis $EC_{50}$ (nM) | Protein | Chemotaxis $EC_{50}$ (nM) |
|---|---|---|---|
| SSDF-1(−68K) | 1.3 | SSDF-1(S4V)(−68K) | 10 |
| SSDF-1(+69S) | 2 | SSDF-1(S4V)-RADI | 18 |
| SSDF-1(+69C) | 1.5 | SSDF-1(S4V)-RADII | 17 |
| SSDF-1-RADI | 10 | SSDF-1(S4V)γ | 47 |
| SSDF-1-RADII | 3 | SSDF-1γ | 58 |

Other Embodiments

From the foregoing description, it is apparent that variations and modifications may be made to the invention described herein to adopt it to various usages and conditions. Such embodiments are also within the scope of the following claims.

All publications, patent applications, and patents, including, for example, U.S. Patent Application Publication No. 2008/0095758, mentioned in this specification are herein incorporated by reference to the same extent as if each independent publication or patent application was specifically and individually indicated to be incorporated by reference.

What is claimed is:

1. A method of treating or ameliorating tissue damage by stimulating angiogenesis in a subject in need thereof, wherein the tissue damage results from a disease or condition, said method comprising administering to said damaged tissue an isolated mutant form of stromal cell derived factor-1 (SDF-1) peptide comprising the formula of a mutant SDF-1 (mSDF-1) or $X_p$-mSDF-1 peptide in an amount sufficient to stimulate angiogenesis and thereby treat or ameliorate said tissue damage in said subject, wherein said mSDF-1 or $X_p$-mSDF-1 is a peptide comprising the amino acid sequence of at least amino acids 1-8 of SEQ ID NO: 53 and which is optionally extended at the C-terminus by all or any portion of the remaining sequence of SEQ ID NO: 53, said SEQ ID NO: 53 comprising the amino acid sequence:

(SEQ ID NO: 53)
K P X$_3$ X$_4$ X$_5$ X$_6$ Y R C P C R F F E S H V A R A N V K

H L K I L N T P N C A L Q I V A R L K N N R Q V

C I D P K L K W I Q E Y L E K A L N K, wherein
 $X_3$ is any amino acid;
 $X_4$ is serine or valine;
 $X_5$ is leucine, praline, threonine, or valine; and
 $X_6$ is any amino acid residue,
and wherein
(a) $X_p$ is a proteinogenic amino acid(s) or a protease protective organic group and p is any integer from 1 to 4;
(b) said mSDF-1 maintains chemoattractant activity for T cells and is inactivated by matrix metalloproteinase-2 (MMP-2), matrix metalloproteinase-9 (MMP-9), leukocyte elastase, and/or cathepsin G at a rate that is at least 50% less than the rate of inactivation of native SDF-1;
(c) said $X_p$-mSDF-1 maintains chemoattractant activity for T cells, is inactivated by dipeptidyl peptidase IV (DPPIV) at a rate that is at least 50% less than the rate at which native SDF-1 is inactivated, and is inactivated by MMP-2, MMP-9, leukocyte elastase, and/or cathepsin G at a rate that is at least 50% less than the rate of inactivation of native SDF-1; and
(d) said mSDF-1 or $X_p$-mSDF-1 peptide does not comprise the amino acid sequence of at least amino acids 1-8 of SEQ ID NO: 52, SEQ ID NO: 56, SEQ ID NO: 60, or SEQ ID NOs: 65-67.

2. The method of claim 1, wherein said isolated mSDF-1 or $X_p$-mSDF-1 peptide is attached to a biologically compatible membrane or is attached to a self-assembling peptide that forms a biologically compatible membrane after administration to said damaged tissue.

3. The method of claim 1, wherein said disease or condition is selected from the group consisting of stroke, limb ischemia, tissue damage due to trauma, myocardial infarction, peripheral vascular disease, and diabetic ulcers.

4. The method of claim 3, wherein said disease or condition is myocardial infarction.

5. The method of claim 3, wherein said disease is peripheral vascular disease.

6. The method of claim 1, wherein said subject is treated for damage to cardiac tissue.

7. The method of claim 1, wherein said administration comprises injecting or implanting said isolated mSDF-1 or $X_p$-mSDF-1 peptide into cardiac tissue of said subject.

8. The method of claim 1, wherein said mSDF-1 peptide is SDF(V3H), consisting of SEQ ID NO: 54.

9. The method of claim 8, wherein said peptide is an $X_p$-mSDF-1 peptide and wherein X is a serine and p is 1.

10. The method of claim 1, wherein said mSDF-1 peptide is SDF(V3C), consisting of SEQ ID NO: 55.

11. The method of claim 10, wherein said peptide is an $X_p$-mSDF-1 peptide and wherein X is a serine and p is 1.

12. The method of claim 1, wherein said mSDF-1 peptide is SDF(L5T), consisting of SEQ ID NO: 56.

13. The method of claim 12, wherein said peptide is an $X_p$-mSDF-1 peptide and wherein X is a serine and p is 1.

14. The method of claim 1, wherein said mSDF-1 peptide is SDF(L5V), consisting of SEQ ID NO: 60.

15. The method of claim 14, wherein said peptide is an $X_p$-mSDF-1 peptide and wherein X is a serine and p is 1.

16. The method of claim 1, wherein said mSDF-1 peptide is SDF(S6C), consisting of SEQ ID NO: 61.

17. The method of claim 16, wherein said peptide is an $X_p$-mSDF-1 peptide and wherein X is a serine and p is 1.

18. The method of claim 1, wherein said mSDF-1 peptide is SDF(S6G), consisting of SEQ ID NO: 62.

19. The method of claim 18, wherein said peptide is an $X_p$-mSDF-1 peptide and wherein X is a serine and p is 1.

20. The method of claim 2, wherein the biologically compatible peptide membrane comprises one or more self-assembling peptides having an amino acid sequence selected from the group consisting of SEQ ID NO: 1-SEQ ID NO: 51, and wherein between 0.1-10% of said one or more self-assembling peptides are bound to the isolated mSDF-1 or $X_p$-mSDF-1 peptide.

21. A method of treating or ameliorating cardiac tissue damage by stimulating angiogenesis in a subject in need thereof, wherein the cardiac tissue damage results from myocardial infarction, said method comprising administering to said damaged cardiac tissue an isolated mutant form of stromal cell derived factor-1 (SDF-1) peptide comprising the formula of a mutant SDF-1 (mSDF-1) or $X_p$-mSDF-1 peptide in an amount sufficient to stimulate angiogenesis and thereby treat or ameliorate said cardiac tissue damage in said subject, wherein said mSDF-1 or $X_p$-mSDF-1 is a peptide comprising the amino acid sequence of at least amino acids 1-8 of SEQ ID NO: 53 and which is optionally extended at the C-terminus by all or any portion of the remaining sequence of SEQ ID NO: 53, said SEQ ID NO: 53 comprising the amino acid sequence:

```
                                              (SEQ ID NO: 53)
K P X3 X4 X5 X6 Y R C P C R F F E S H V A R A N V K
H L K I L N T P N C A L Q I V A R L K N N N R Q V
C I D P K L K W I Q E Y L E K A L N K,
``` wherein
 $X_3$ is any amino acid;
 $X_4$ is serine or valine;
 $X_5$ is leucine, praline, threonine, or valine; and
 $X_6$ is any amino acid residue, and wherein
(a) $X_p$ is a proteinogenic amino acid(s) or a protease protective organic group and p is any integer from 1 to 4;
(b) said mSDF-1 maintains chemoattractant activity for T cells and is inactivated by matrix metalloproteinase-2 (MMP-2), matrix metalloproteinase-9 (MMP-9), leukocyte elastase, and/or cathepsin G at a rate that is at least 50% less than the rate of inactivation of native SDF-1;
(c) said $X_p$-mSDF-1 maintains chemoattractant activity for T cells, is inactivated by dipeptidyl peptidase IV (DPPIV) at a rate that is at least 50% less than the rate at which native SDF-1 is inactivated, and is inactivated by MMP-2, MMP-9, leukocyte elastase, and/or cathepsin G at a rate that is at least 50% less than the rate of inactivation of native SDF-1; and
(d) said mSDF-1 or $X_p$-mSDF-1 peptide does not comprise the amino acid sequence of at least amino acids 1-8 of SEQ ID NO: 52, SEQ ID NO: 56, SEQ ID NO: 60, or SEQ ID NOs: 65-67.

* * * * *